United States Patent
Weng

(10) Patent No.: US 10,202,656 B2
(45) Date of Patent: Feb. 12, 2019

(54) DIVIDING OF REPORTER PROTEINS BY DNA SEQUENCES AND ITS APPLICATION IN SITE SPECIFIC RECOMBINATION

(71) Applicant: Wei Weng, Sayville, NY (US)

(72) Inventor: Wei Weng, Sayville, NY (US)

(73) Assignee: INGENIOUS TARGETING LABORATORIES, Ronkonkoma, NY (US)

(*) Notice: Subject to any disclaimer, the term of this patent is extended or adjusted under 35 U.S.C. 154(b) by 0 days.

(21) Appl. No.: 15/445,799

(22) Filed: Feb. 28, 2017

(65) Prior Publication Data

US 2017/0253938 A1    Sep. 7, 2017

Related U.S. Application Data

(60) Provisional application No. 62/300,966, filed on Feb. 29, 2016.

(51) Int. Cl.
| | | |
|---|---|---|
| C12N 15/63 | (2006.01) |
| C12Q 1/6897 | (2018.01) |
| C22C 38/00 | (2006.01) |
| E04C 5/02 | (2006.01) |
| B21J 5/08 | (2006.01) |
| E04C 5/03 | (2006.01) |

(52) U.S. Cl.
CPC ............ *C12Q 1/6897* (2013.01); *C22C 38/00* (2013.01); *E04C 5/02* (2013.01); *B21J 5/08* (2013.01); *E04C 5/03* (2013.01)

(58) Field of Classification Search
None
See application file for complete search history.

(56) References Cited

U.S. PATENT DOCUMENTS

| | | |
|---|---|---|
| 2004/0045043 A1 | 3/2004 | Finney et al. |
| 2004/0077089 A1 | 4/2004 | Xin et al. |
| 2005/0221343 A1 | 10/2005 | Waldo et al. |
| 2007/0101452 A1 | 5/2007 | Fraser et al. |
| 2009/0113561 A1 | 4/2009 | Von Melchner et al. |
| 2011/0035815 A1 | 2/2011 | Zong et al. |

OTHER PUBLICATIONS

Written Opinion issued in corresponding International Application No. PCT/US2017/020025 (4 pages).
International Search Report issued in corresponding International Application No. PCT/US2017/020025 (3 pages).

*Primary Examiner* — Celine X Qian
(74) *Attorney, Agent, or Firm* — Venable LLP

(57) ABSTRACT

Methods and constructs for inserting an intron into a reporter protein coding sequence in a eukaryotic cell and their application of monitoring and reporting genomic modifications are provided. Various related compositions, cells and kits are also provided.

19 Claims, 21 Drawing Sheets
Specification includes a Sequence Listing.

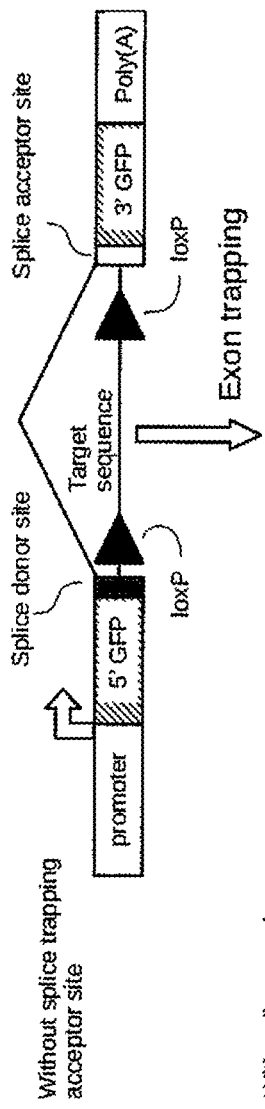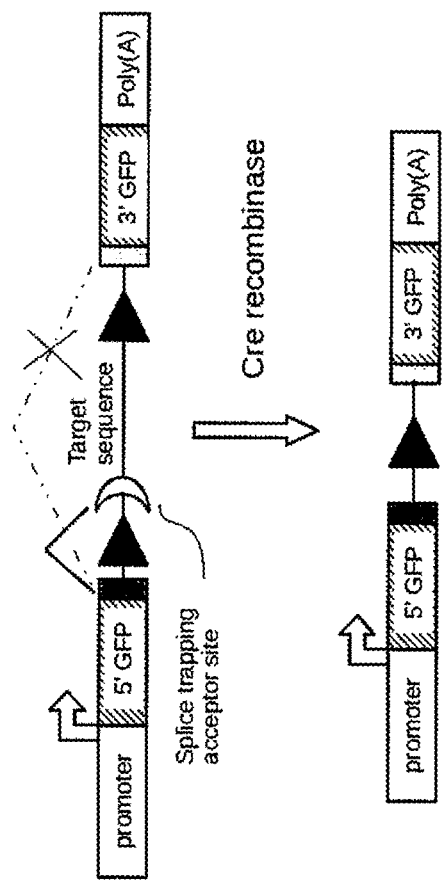
FIG. 4

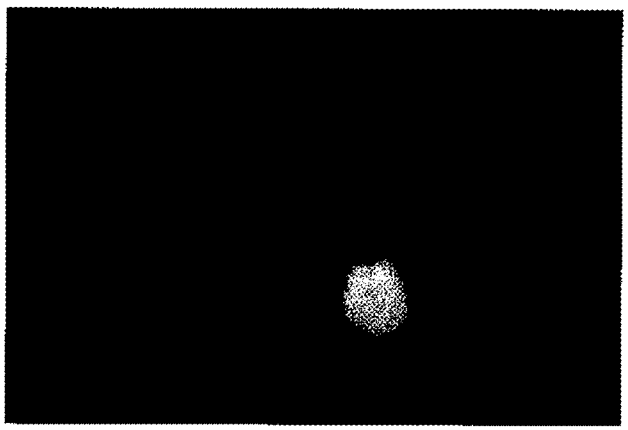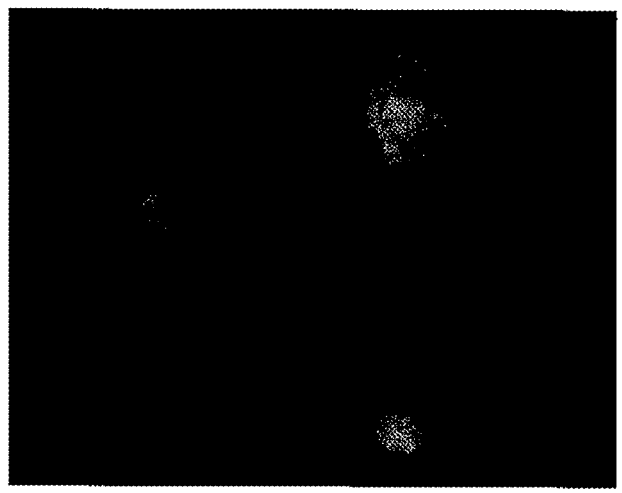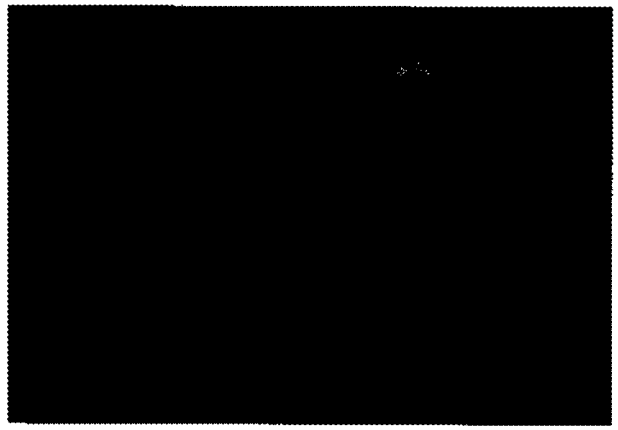
FIG. 11

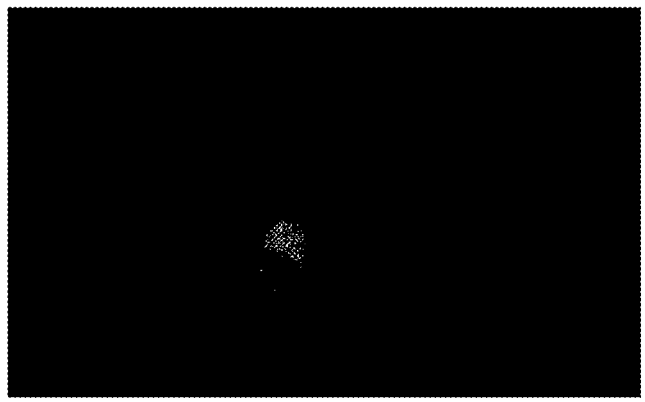
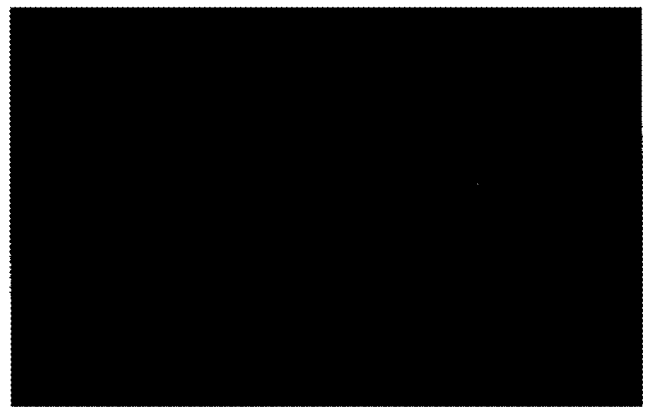
FIG. 12

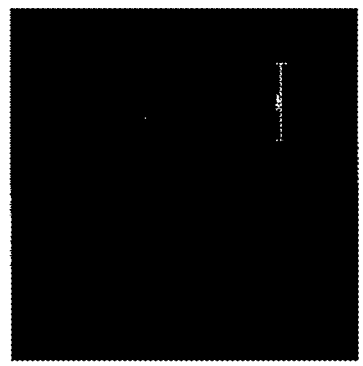
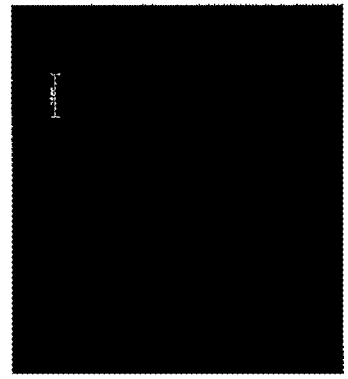
FIG. 13

PB1/2 Probe Sequence (527 bps)

GGTCAACAGAGCCAACTTTCAGGACAGGCAGGGCTACACATAGAAACCCAGTCTGAAAAACA
AAACAAAACAACAAAATAATAATTAATAAATAAATAAGTTGATGTTTATCTGTAAACCCTCAAACACTCA
TCCATGGTCCCTTCTCCCCTTAGAGGTGTGGTGGCTCTCTGTCTCTGAGTGTTGCTCTAGCAAGGTCG
GTAAAGCCTAAATGTACAGAAGGAAGTGGCCAGTTGGGCCTCAGCCACCGGCCTAAACACGCACAGCC
ACCAGCTGGCTGGACTTCCTCACAGCTCTCAGGCCAGGGTTCTGGAGCAGCTTCAACTGGA
CACAGATCAGAGGTGCCAGGCCTGTGAGGCAAGTGTTTTACTGCTGCTGTCGAAGCCTCCTC
AGCTGTTGCTTCCTTCTAGTAGCAGTCCCACCCATCCCATGAGGAGTAGGAGTTCAAAGGCCGACCA
AAGACAGGACCGGATGGAGCCTACCTTAGCAGATAAGCAGCAATATGGAGCTCGGAGTTCCTG (SEQ ID NO: 34)

Results: EcoRV restriction cut. Wildtype 15.3KB; targeted: 18.6KB

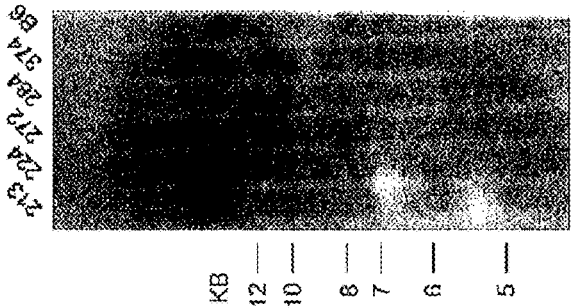

FIG. 16a

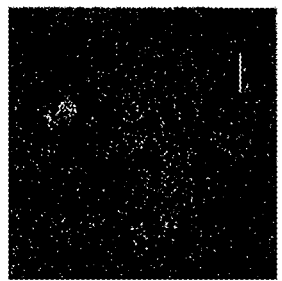
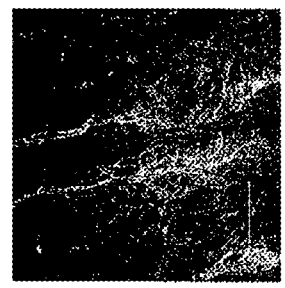
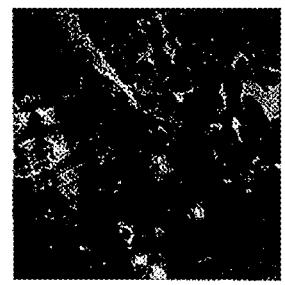
FIG. 17

PB7/8 Probe Sequence (459 bps)

GCATGCTGAGCCCTCTGGAGACTGAAGCGGGAGAAGCCAGCACCTGAAGCTGAA
GTACCCCTTCATATCTCTTAAGACTCAGAGCAAACCCTCTGGTTCGCTTTCCCATCAGA
CCTTGCTGCTGAAACTTGGTGGTCATAAAGGAAAAGAGTACACTGAAGCCGGCTCACAGT
GATGTCGTCAGAATAGAACATAGGGCCCAGACTCAAACAAGCCTGAACACTGTGTACTTA
CTATCTGAGAGCTAAGTACATCTGTTGCATGGGAAGTTGTGGCCTGTGTTGTAGCAGTTTG
TGTGGAGTTGGGAGAGATTATAGGGAGGAGGGTTTAGATGTATTCAACTGTGAAGAG
GTCCTTCATATGATTGGCCAACAGTTGCCAAAGCATCCCAGGAGGAGGAGTAGGCA
GGCAGAAGGACAGCTCTGAAAGTAGACATGTTGACTAATGCTGTGTAACCAT (SEQ ID NO: 36)

Results: EcoRV restriction cut. Wildtype 15.9KB; targeted: 18.7KB

FIG. 18a

PB5/6 Probe Sequence (528 bps)

GTACCTGTCAGTGTAATGAAGTAGTTGTTAGACCCAGATAAAAGGAAATAGGATAACAGC
TATATCTAGTGGGCCCAGTTAAACTGCCATGTTTGTCATTTACTCTGGGGTAAATATTGCCATTTCAT
TTTCAGATGAAGGGTCTCAACAAATGCCTTTCAATGTCACATACTTGAAAATACTACATAGAGGTA
GGCTTTGCCTCTACAGCATGTGCTGTAAAAAATGATTCTTAACTGCCATTTCAGCATAAGCTGGT
AGGAGAAATAGAAAGCAGTCAGGCCGTTGCGGCAAATCCTGACTAATTTAAAAACCATCTTGAATAAT
ACAACAGCACAGATCTCTAGCTTGTAGTGTTCTTCAGGATGTCTGCCCCCAAAACATTAGCATTAGC
TGGGTAGGAGAGTTAACAGAAGTGCTGAGCATGAAATGGCCTAAGCCTGCCAACTGCTACTACAGT
CCTGCTGAAACAGGACGTGTCCTGCCTTGCTGTGTCTTGAGAACATCTGCCTGCACTG (SEQ ID NO: 37)

Results: BcII restriction cut. Wildtype 12.3KB; targeted: 8.4KB

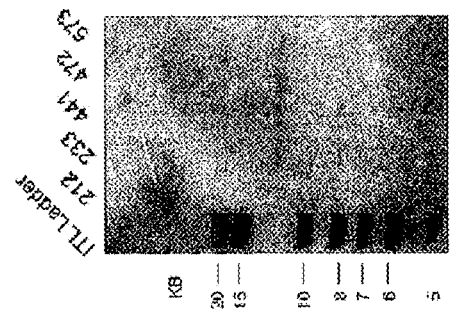

Clones 233, 441, and 573 were confirmed as correctly targeted.

FIG. 18b

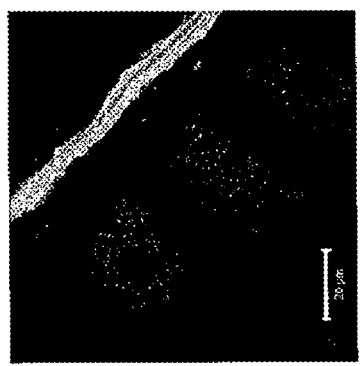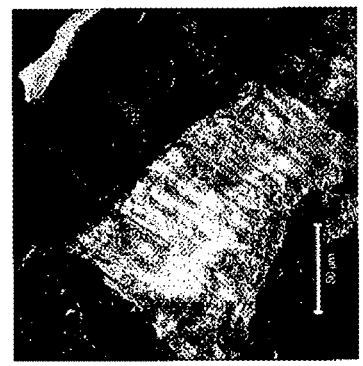
FIG. 19

SEQUENCE LISTING

```
<160> NUMBER OF SEQ ID NOS: 37

<210> SEQ ID NO 1
<211> LENGTH: 1751
<212> TYPE: DNA
<213> ORGANISM: artificial sequence
<220> FEATURE:
<223> OTHER INFORMATION: promoter

<400> SEQUENCE: 1
ctagttatta atagtaatca attacggggt cattagttca tagcccatat atggagttcc     60
gcgttacata acttacggta aatggcccgc ctggctgacc gcccaacgac ccccgcccat    120
tgacgtcaat aatgacgtat gttcccatag taacgccaat agggactttc cattgacgtc    180
aatgggtgga gtatttacgg taaactgccc acttggcagt acatcaagtg tatcatatgc    240
caagtacgcc ccctattgac gtcaatgacg gtaaatggcc cgcctggcat tatgcccagt    300
acatgacctt atgggacttt cctacttggc agtacatcta cgtattagtc atcgctatta    360
ccatggtcga ggtgagcccc acgttctgct tcactctccc catctccccc cctccccac    420 ccccaatttt gtatttattt attttttaat tattttgtgc agcgatgggg gcggggggg    480 ggggggggcg cgcgccaggc ggggcgggc ggggcgaggg gcggggcggg gcgaggcgga    540
gaggtgcggc ggcagccaat cagagcggcg cgctccgaaa gtttcctttt atggcgaggc    600
ggcggcggcg gcggccctat aaaaagcgaa gcgcgcggcg ggcgggagtc gctgcgttgc    660
cttcgccccg tgccccgctc cgcgccgcct cgcgccgccc gccccggctc tgactgaccg    720
cgttactccc acaggtgagc gggcgggacg gcccttctcc tccgggctgt aattagcgct    780
tggtttaatg acggctcgtt tcttttctgt ggctgcgtga aagccttaaa gggctccggg    840
agggcccttt gtgcgggggg gagcggctcg gggggtgcgt gcgtgtgtgt gtgcgtgggg    900
```

```
agcgccgcgt gcggcccgcg ctgcccggcg gctgtgagcg ctgcgggcgc ggcgcggggc      960
tttgtgcgct ccgcgtgtgc gcgagtggggag cgcggccggg ggcggtgccc cgcggtgcgg     1020
gggggctgcg aggggaacaa aggctgcgtg cggggtgtgt gcgtgggggg gtgagcaggg     1080
ggtgtgggcg cggcggtcgg gctgtaaccc ccccctgcac ccccctcccc gagttgctga     1140
gcacggcccg gcttcgggtg cggggctccg tgcggggcgt ggcgcggggc tcgccgtgcc     1200 gggcggggg tggcggcagg tgggggtgcc gggcggggcg gggccgcctc gggccgggga     1260
gggctcgggg gaggggcgcg gcggcccgg agcgccggcg gctgtcgagg cgcggcgagc     1320
cgcagccatt gccttttatg gtaatcgtgc gagagggcgc agggacttcc tttgtcccaa     1380
atctggcgga gccgaaatct gggaggcgcc gccgcacccc ctctagcggg cgcgggcgaa     1440
gcggtgcggc gccggcagga aggaaatggg cgggagggc cttcgtgcgt cgccgcgccg     1500 ccgtccccctt ctccatctcc agcctcgggg ctgccgcagg gggacggctg ccttcggggg     1560
ggacggggca gggcggggtt cggcttctgg cgtgtgaccg gcggctctag agcctctgct     1620
aaccatgttc atgccttctt cttttttccta cagctcctgg gcaacgtgct ggttattgtg     1680
ctgtctcatc attttggcaa agaattctgc agtcgacggt accgcgggcc cgggatccac     1740
cggtcgccac c                                                         1751

<210> SEQ ID NO 2
<211> LENGTH: 720
<212> TYPE: DNA
<213> ORGANISM: artificial sequence
<220> FEATURE:
<223> OTHER INFORMATION: EGFP

<400> SEQUENCE: 2
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga cccctgaagtt catctgcacc accggcaagc tgcccgtgcc ctggcccacc     180
ctcgtgacca cccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctttagcaaa gaccccaacg agaagcgcga tcacatggtc     660
ctgctggagt tcgtgaccgc cgccgggatc actctcggca tggacgagct ttacaagtag     720

<210> SEQ ID NO 3
<211> LENGTH: 678
<212> TYPE: DNA
<213> ORGANISM: artificial sequence
<220> FEATURE:
<223> OTHER INFORMATION: DsRed

<400> SEQUENCE: 3
atggatagca ctgagaacgt catcaagccc ttcatgcgct tcaaggtgca catggagggc      60
tccgtgaacg gccacgagtt cgagatcgag ggcgagggcg agggcaagcc ctacgagggc     120
```

```
acccagaccg ccaagctgca ggtgaccaag ggcggccccc tgcccttcgc ctgggacatc    180
ctgtcccccc agttccagta cggctccaag gtgtacgtga agcacccccgc cgacatcccc    240 gactacaaga agctgtcctt ccccgagggc ttcaagtggg agcgcgtgat gaacttcgag    300
gacggcggcg tggtgaccgt gacccaggac tcctccctgc aggacggcac cttcatctac    360
cacgtgaagt tcatcggcgt gaacttcccc tccgacggcc ccgtaatgca gaagaagact    420
ctgggctggg agccctccac cgagcgcctg taccccccgcg acggcgtgct gaagggcgag    480
atccacaagg cgctgaagct gaagggcggc ggccactacc tggtggagtt caagtcaatc    540
tacatggcca agaagcccgt gaagctgccc ggctactact acgtggactc caagctggac    600
atcacctccc acaacgagga ctacaccgtg gtggagcagt acgagcgcgc cgaggcccgc    660
caccacctgt tccagtag                                                  678
```

```
<210> SEQ ID NO 4
<211> LENGTH: 40
<212> TYPE: DNA
<213> ORGANISM: Bacteriophage P1

<400> SEQUENCE: 4
acgcgtataa cttcgtataa tgtatgctat acgaagttat                          40

<210> SEQ ID NO 5
<211> LENGTH: 34
<212> TYPE: DNA
<213> ORGANISM: Saccharomyces cerevisiae

<400> SEQUENCE: 5
gaagttccta ttctctagaa agtataggaa cttc                                34

<210> SEQ ID NO 6
<211> LENGTH: 31
<212> TYPE: DNA
<213> ORGANISM: unknown
<220> FEATURE:
<223> OTHER INFORMATION: bacteria P1 like phage

<400> SEQUENCE: 6
taacttaaat aatgccaatt atttaaagtt a                                   31

<210> SEQ ID NO 7
<211> LENGTH: 204
<212> TYPE: DNA
<213> ORGANISM: mouse

<400> SEQUENCE: 7
tacaatgttg gtctgaaact cagccttgag cctctggagc tgctcagcag tgaaggctgt    60
gcgaggccgc ttgtcctctt tgttagggtt cttcttcttt ggttttcggg acctgggacc    120
tggttgtcat ggaggagaaa gggcagaggt tactggttgc tggagtctag ctacttatcc    180
acaaccaacg cacccaagct agct                                           204

<210> SEQ ID NO 8
<211> LENGTH: 52
<212> TYPE: DNA
<213> ORGANISM: mouse

<400> SEQUENCE: 8
gtaattccgt actgctgccc tcaagccctc ggggccacat tctctctggc cg            52
```

<210> SEQ ID NO 9
<211> LENGTH: 52
<212> TYPE: DNA
<213> ORGANISM: mouse

<400> SEQUENCE: 9

```
gggaccaaga aattgatcat ggctacgaaa ctgaaacctt tttctttct ag           52
```

<210> SEQ ID NO 10
<211> LENGTH: 381
<212> TYPE: DNA
<213> ORGANISM: artificial sequence
<220> FEATURE:
<223> OTHER INFORMATION: GFP

<400> SEQUENCE: 10

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa g                                             381
```

<210> SEQ ID NO 11
<211> LENGTH: 339
<212> TYPE: DNA
<213> ORGANISM: artificial sequence
<220> FEATURE:
<223> OTHER INFORMATION: GFP

<400> SEQUENCE: 11

```
ggcatcgact tcaaggagga cggcaacatc ctggggcaca agctggagta caactacaac    60
agccacaacg tctatatcat ggccgacaag cagaagaacg gcatcaaggt gaacttcaag   120
atccgccaca acatcgagga cggcagcgtg cagctcgccg accactacca gcagaacacc   180
cccatcggcg acggccccgt gctgctgccc gacaaccact acctgagcac ccagtccgcc   240
cttagcaaag accccaacga gaagcgcgat cacatggtcc tgctggagtt cgtgaccgcc   300
gccgggatca ctctcggcat ggacgagctt tacaagtag                          339
```

<210> SEQ ID NO 12
<211> LENGTH: 568
<212> TYPE: DNA
<213> ORGANISM: artificial sequence
<220> FEATURE:
<223> OTHER INFORMATION: GFP

<400> SEQUENCE: 12

```
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctgggggcac  420
```

```
aagctggagt acaactacaa cagccacaac gtctatatca tggccgacaa gcagaagaac      480
ggcatcaagg tgaacttcaa gatccgccac aacatcgagg acggcagcgt gcagctcgcc      540
gaccactacc agcagaacac ccccatcg                                         568
```

<210> SEQ ID NO 13
<211> LENGTH: 152
<212> TYPE: DNA
<213> ORGANISM: artificial sequence
<220> FEATURE:
<223> OTHER INFORMATION: GFP

<400> SEQUENCE: 13

```
gcgacggccc cgtgctgctg cccgacaacc actacctgag cacccagtcc gcccttagca      60
aagaccccaa cgagaagcgc gatcacatgg tcctgctgga gttcgtgacc gccgccggga      120
tcactctcgg catggacgag ctttacaagt ag                                    152
```

<210> SEQ ID NO 14
<211> LENGTH: 38
<212> TYPE: DNA
<213> ORGANISM: mouse

<400> SEQUENCE: 14

```
gtaggtttcc atgagccaag aacacctaca gtgtggat                              38
```

<210> SEQ ID NO 15
<211> LENGTH: 49
<212> TYPE: DNA
<213> ORGANISM: mouse

<400> SEQUENCE: 15

```
ttgggctttc aggaagggggg gctgtaaaca caattctttt attttgcag                 49
```

<210> SEQ ID NO 16
<211> LENGTH: 135
<212> TYPE: DNA
<213> ORGANISM: artificial sequence
<220> FEATURE:
<223> OTHER INFORMATION: DsRed

<400> SEQUENCE: 16

```
atggatagca ctgagaacgt catcaagccc ttcatgcgct tcaaggtgca catggagggc      60
tccgtgaacg gccacgagtt cgagatcgag ggcgagggcg agggcaagcc ctacgagggc      120
acccagaccg ccaag                                                       135
```

<210> SEQ ID NO 17
<211> LENGTH: 543
<212> TYPE: DNA
<213> ORGANISM: artificial sequence
<220> FEATURE:
<223> OTHER INFORMATION: DsRed

<400> SEQUENCE: 17

```
ctgcaggtga ccaagggcgg ccccctgccc ttcgcctggg acatcctgtc ccccagttc       60 cagtacggct ccaaggtgta cgtgaagcac cccgccgaca tccccgacta caagaagctg      120
tccttccccg agggcttcaa gtgggagcgc gtgatgaact tcgaggacgg cggcgtggtg      180
accgtgaccc aggactcctc cctgcaggac ggcaccttca tctaccacgt gaagttcatc      240
ggcgtgaact cccctccga cggccccgta atgcagaaga agactctggg ctgggagccc       300
tccaccgagc gcctgtaccc ccgcgacggc gtgctgaagg gcgagatcca caaggcgctg      360
```
aagctgaagg gcggcggcca ctacctggtg gagttcaagt caatctacat ggccaagaag  420
cccgtgaagc tgcccggcta ctactacgtg gactccaagc tggacatcac ctcccacaac  480
gaggactaca ccgtggtgga gcagtacgag cgcgccgagg cccgccacca cctgttccag  540
tag                                                                543

<210> SEQ ID NO 18
<211> LENGTH: 2035
<212> TYPE: DNA
<213> ORGANISM: artificial sequence
<220> FEATURE:
<223> OTHER INFORMATION: neomycin resistance gene having PGK-1 promotor,
      G418 resistance selection cassette (Neo)

<400> SEQUENCE: 18
gctagctgat catctagcca tgggcccgta cgccggctta agtgtaccaa cgaagttcct   60
attctctaga aagtatagga acttcattct accgtgtagg ggaggcgctt ttcccaaggc  120
agtctggagc atgcgcttta gcagccccgc tgggcacttg gcgctacaca agtggcctct  180
ggcctcgcac acattccaca tccaccggta ggcgccaacc ggctccgttc tttggtggcc  240
ccttcgcgcc accttccact cctccccctag tcaggaagtt ccccccccgcc ccgcagctcg  300 cgtcgtgcag gacgtgacaa atggaagtag cacgtctcac tagtctcgtg cagatggaca  360
gcaccgctga gcaatggaag cgggtaggcc tttgggcag cggccaatag cagctttgct   420
ccttcgcttt ctgggctcag aggctgggaa ggggtgggtc cggggcggg ctcaggggcg   480 ggctcagggg cggggcgggc gcccgaaggt cctccggagg cccggcattc tgcacgcttc   540
aaaagcgcac gtctgccgcg ctgttctcct cttcctcatc tccgagcctt tcgacctgca   600
gcagcacgtg ttgacaatta atcatcggca tagtatatcg gcatagtata atacgacaag   660
gtgaggaact aaaccatggg atcggccatt gaacaagatg gattgcacgc aggttctccg   720
gccgcttggg tggagaggct attcggctat gactgggcac aacagacgat cggctgctct   780
gatgccgccg tgttccggct gtcagcgcag gggcgcccgg ttcttttttgt caagaccgac   840 ctgtccggtg ccctgaatga actgcaggac gaggcagcgc ggctatcgtg gctggccacg   900
acgggcgttc cttgcgcagc tgtgctcgac gttgtcactg aagcgggaag ggactggctg   960
ctattgggcg aagtgccggg gcaggatctc ctgtcatctc accttgctcc tgccgagaaa  1020
gtatccatca tggctgatgc aatgcggcgg ctgcatacgc ttgatccggc tacctgccca  1080
ttcgaccacc aagcgaaaca tcgcatcgag cgagcacgta ctcggatgga agccggtctt  1140
gtcgatcagg atgatctgga cgaagagcat caggggctcg cgccagccga actgttcgcc  1200
aggctcaagg cgcgcatgcc cgacggcgag gatctcgtcg tgacccatgg cgatgcctgc  1260
ttgccgaata tcatggtgga aaatggccgc ttttctggat tcatcgactg tggccggctg  1320
ggtgtggcgg accgctatca ggacatagcg ttggctaccc gtgatattgc tgaagagctt  1380
ggcggcgaat gggctgaccg cttcctcgtg ctttacggta tcgccgctcc cgattcgcag  1440
cgcatcgcct tctatcgcct tcttgacgag ttcttctgag cgggactctg gggttcgaat  1500
aaagaccgac caagcgacgt ctgagagctc cctgatatca gatcctcatg cctcctgacg  1560
gccacttcag tttggtcaaa tgattgctat ggcatcgtc ctcaagaaac agctctgttt  1620
tgctgagtca gctttcccca cttgctccca ggatttcttc tgaggaaact attccttagc  1680
aaatccattt attccattag aatcacttca cacccgggcc agtgaaagct cacttctcac  1740
atggttaggg gaaggccgtt tgacatctgc ttcttgtagc aactgaagat cccgactaat  1800

```
gacgttcctg gagagtatgg ctttccttcc cgatggtcct ttctgctgta attaattggt    1860
cactggattg cagaaggtct cttcctggat cacctgacaa ctcactccca tgtcttccag    1920
acttctgtct tactctagat ctggagaact tacaaccgcg ggaagttcct attctctaga    1980
aagtatagga acttcgcgac acggacacaa tcccacgaac gtacccgggg atcct         2035
```

<210> SEQ ID NO 19
<211> LENGTH: 1028
<212> TYPE: DNA
<213> ORGANISM: artificial sequence
<220> FEATURE:
<223> OTHER INFORMATION: Cre recombinase

<400> SEQUENCE: 19

```
atgtccaatt tactgaccgt acaccaaaat ttgcctgcat taccggtcga tgcaacgagt     60
gatgaggttc gcaagaacct gatggacatg ttcagggatc gccaggcgtt ttctgagcat    120
acctggaaaa tgcttctgtc cgtttgccgg tcgtgggcgg catggtgcaa gttgaataac    180
cggaaatggt ttcccgcaga acctgaagat gttcgcgatt atcttctata tcttcaggcg    240
cgcggtctgg cagtaaaaac tatccagcaa catttgggcc agctaaacat gcttcatcgt    300
cggtccgggc tgccacgacc aagtgacagc aatgctgttt cactggttat gcggcggatc    360
cgaaaagaaa acgttgatgc cggtgaacgt gcaaaacagg ctctagcgtt cgaacgcact    420
gatttcgacc aggttcgttc actcatggaa atagcgatc gctgccagga tatacgtaat    480
ctggcatttc tggggattgc ttataacacc ctgttacgta tagccgaaat tgccaggatc    540
agggttaaag atatctcacg tactgacggt gggagaatgt taatccatat tggcagaacg    600
aaaacgctgg ttagcaccgc aggtgtgagag aaggcactta gcctgggggt aactaaactg    660
gtcgagcgat ggatttccgt ctctggtgta gctgatgatc gaataacta cctgttttgc    720 cgggtcagaa aaaatggtgt tgccgcgcca tctgccacca gccagctatc aactcgcgcc    780
ctggaaggga ttttttgaagc aactcatcga ttgatttacg gcgctaagga tgactctggt    840
cagagatacc tggcctggtc tggacacagt gcccgtgtcg gagccgcgcg agatatggcc    900
cgcgctggag tttcaatacc ggagatcatg caagctggtg gctggaccaa tgtaaatatt    960
gtcatgaact atatccgtaa cctggatagt gaaacagggg caatggtgcg cctgctggaa   1020
gatggcga                                                             1028
```

<210> SEQ ID NO 20
<211> LENGTH: 49
<212> TYPE: DNA
<213> ORGANISM: artificial sequence
<220> FEATURE:
<223> OTHER INFORMATION: poly(A)

<400> SEQUENCE: 20

```
gcgggactct ggggttcgaa taaagaccga ccaagcgacg tctgagctc               49
```

<210> SEQ ID NO 21
<211> LENGTH: 7611
<212> TYPE: DNA
<213> ORGANISM: mouse

<400> SEQUENCE: 21

```
ccggcccatc actatcaaag acgacaaggg caatctcaac cgctgcattg cagatgttgt     60
ttcggtgtgt cccacagctc ctgggagggt cctgtgggga ttagagggaa gggactactg    120
```

```
gcctaggtca gtcataaatg tgtattcttg gggtttctgg tcctaagcag tactctggga    180
gggctcacct cagctgtgag gaggatgaga agcagccaag gagcctaagg cccacctgac    240
tgagttcctt cttgtgaaag ggaccaggac ctactcgggc aggaccctgg cttgagggg     300 ttgtgtagga gtacttccca gattcccaga attcctctca gagttgtgat cccaaatgtc    360
cgtaggccca gacagttagc agacaggtct taagtgtagc ccccaagcag gaaggagccc    420
cagtgtgggg tgtcgggagg aacatgggtg ggggcctggt ccctataatt ggcctacaag    480
ctatccccac tgagtaagag atgcctaatg tacatgctcc ccacagctct tcattacagt    540
catggacaag ctgcgtctgg agatccgtgc catggacgag gtgcagaagt tgggcaggga    600
gccccgggcc tggatggagg ggaacagagc aaggtacaga gggtctcacg agggtagcgc    660
ttgtgtctgt agattcagcc agacctgcgg gagctgatgg agacaatgca cagaatgagc    720
cacctgcctc cagacttcga gggccgccag acagtcagcc agtggtgagt tgctctcccg    780
cgcaggcgca gggagcctcg tggtggtgag tgggtctccc gcaggaagcc tcgtggtgat    840
gtcacagccc ctctgctcag acacacttgt gcctgtgccc ctaggctgca gaccctgagt    900
ggtatgtcgg cctctgacga gctggatgac tctcaagttc gccagatgct cttcgatctg    960
gagtccgctt acaacgcctt taaccgcttc ctacacgcct aagcctcacc gagacaggaa   1020
tgagagtggt agagatgtga cgactcagcc ccccagtgtg tctacatccg tcctagatgc   1080
ctatattgtc aggatatcac ccacaataaa tatttgtcta accttcctgc gtgggcagc    1140 tatactgagc ccccgccctg tgtgatctct ctctctctct ctctctctct ctctatatat   1200
atatatatat acatatatat atatatatat ttctgacctt gagtcagtgc cctgtctcct   1260
ggggcggggg ggggggcac agagcccctg ttgctcattg cacacataga acaacctctg    1320
tgagagatga taactgggca gttatacagc aaagacctgc ttcagcacca gagtaaactg   1380
agtcagcggg ggccggtgct gatggtacct ggcagtggct gctactgatg gtagccagta   1440
agtagacaaa agggaagaat taaaaaatac acacatacac atttatttgg tgggtgaagc   1500
aagacaagct ccacaagcaa gctccaccaa cttcacacat agacagacag acagacatag   1560
acatatatac atatacactt tggttggatg gggcagagct ccaaccactt tgtgtgtgtg   1620
tgtgtgtgta tgtgtgtata cagacaggca tgcatgtaca cgtacatctg gtggatggag   1680
caaactccac atatatacat ataaattcta catatttagt ggatggaaag aaataccaac   1740
aaccttttct cccacagctt atatatccca gcaaaatctt tcgcagtaca gaagtcacaa   1800
tgccgttaca ttctattttt ctctaagtaa atgattacaa taagtataca ggcacacaca   1860
cacacacaca cacacacaca cacacacaca cacacaaatg tttcctgaat accctcacat   1920
gatcaaatgt ttaagtatta tgggtgaaaa acaaacatga aaaacattcc caagaaccga   1980
catacactgg taactaaaca actcgttaca gattaacaaa gtgtaagcaa gcaaggtagt   2040
tttctcaccc agtttctctt aactgacagg cagcaatttg tggttacaaa ggaaaaaaaa   2100
atcagttatc ttgttattta tcttaaaaag aaatcttata aaaattttaa aagaatcaca   2160
aatctaaact tttgtataaa aaccaaccag ccagagctgg agagaaggct cagcggttga   2220
gagcactgac tgatcttcca gaggtcctga gttcaaatcc cagcaactat atgatggctt   2280
acaaccatct gtaatgagat ctgacgccct cttctggtgc atctacagtg tgcttagata   2340
taataataaa taaattttag gctggactga gtggggccga ccagtgcaag caaccttcat   2400
ttccagcaac cacatgatag ctcacaacca tcagtacagc tacagtgtac ccacggatac   2460
ataaaataaa taaataaatc ttttaaaaaa aacaaaacaa aacagccatt tctattttaa   2520
```

```
atcctcaagt tgcatagtta cccattagca aattttatca ggaagttgag gggggaaaaa    2580
tgggtaccag aaattaatca acaccttgat gaccagccca atgttagcaa gggagtcaca    2640
ttagccagtg ccagccaggc taccattgtt cttgtttcca gaccataaaa aaccctctag    2700
ctcggctatt agtagtgtgc atttctgaag tacaaactgt ccccaaagat aagagccact    2760
aacaaaaaca tctattctcc aaattccttt gtttgttttc caagacaggg tttctctgtg    2820
tagccctggc tgacctggag ctcaccctat agaccaggcc ggcctcgaac tcagaaatct    2880
gcttgcttct gcctcccaag tgctgggact aaaggcgtgg gccaccactg cctggctcca    2940 aattcttttct aaaagtggtg atcattgcta acaatctaca tctctaagtt ctttctcagg    3000
gtggtggatg aatcattaat ctctccagca gcagtgcctg aaaaagacca agcactaata    3060
ctgtaagcgc cagtgatgca gcccggtgtg gggctagaag cccccacgga gttttcacgc    3120
aagtcattga ctgtacgggg tatggtggct ggaaagacaa gttgaacaga actctacaat    3180
agcatacatg aaggtctgag gaagtcctca ggatgacaca gagggctctg cttcttggag    3240
gcacgcccat tgtgggtggg ccggattccg agagagttct aaagcctttc acatgcctcc    3300
taaacaagcc tcaaggacta tagggaccag gtgagtcctc acagccactg gaatggctgg    3360
catctggcaa cctacgtggc tgcctccttg cctactggga acaccttcct agcagcccct    3420
gagagctcta ggcagttgac aggctctgtg aattcagtcc agagcacctc ccctgctgtc    3480
ctgtgctgag ttagacacca tgactctgtc atgcgacatt caaccctaca aggttactca    3540
acccaaggcc tgtgcgggtt gctagacaaa cgctttgcca ctgagcgacc ttcaaagctc    3600
ttgcttattt ttgtttttttt ttttaaatca tgcatatggt ccaggcagtg gtggcgcatg    3660
cctttaatcc cagcacttgg gaggcagagg caggcagatt tctgagttca aggccagcct    3720
ggtctacacg agtgagttcc aggaagccaa ggctatacag agaaaccctg tctccctgtc    3780
tcgaaaaaca aaacaaaaca aaaaaaaaca aaaaaaaaaa aaacaaaaaa aaaaaaaaaa    3840
aagaaaaaca aaacaaaaca aaagaaactg taaaaaaaaa atcatgcata tgaatatttt    3900
gcctccatgt atatctatct gcctaccaca cgcatgattg gtgacataga aaccagagaa    3960
ggccttggat cccctgaaat tatagttaca ggtaggtttt tttttttcttc gagacagggt    4020 ttttctgtgt agccccggct gtcctggaac tcactctgta gaccaggctg gccttgaact    4080
cagaaatccg cctgcctttg cctccaacag gtagttttga gctattatat ggatgctcag    4140
aacccaggtc tctagaaga agagtcagcc cttgtaactg ctgagccatc tctccagccc    4200
ctttggattt tttgagatgg tctcactatg tcacccacac tggcctcaaa cccaatcctg    4260
attctgcttc tccagtgatg gagtcacagg tgtttgccac cacgcccaga acaggcctgc    4320
tccaaccaac ctcacttttg ttttctaaga taggatctgc ctagccccaa acttgcttat    4380
agggaccagg ctgacctcta actcaaagag ataaatatgc ctgcctctga ctccggagtg    4440
ctgggattag gggtattcac cgtgatacct ggattctact tctttctta ttatctgtag     4500 ccactgaatt aagtcttgca ggagtcctag ggaatcacta accagggagc actgttttgc    4560 tctatttaa ttttgtactg tgataacaca cagaagttgc cacttggacc acatttcagt    4620
ggcactgagt tcagccattg tattgtcctt tccacacctt catctaccca agcgaaacct    4680
tcacaagtag taactccagt tcccgggtgc tgaagttcac catttgactt ttttttttt     4740 ttttttttt tggcccgagg gaacaattgt tgcggcatac aatagaggtg aaagaacagc    4800
tttctggagc tgcattttt ccttctacca ccgtgaatcc ttggcaagct tctttacaca    4860
```

```
cacacacaca caccacacca cacacacaca cacacacaca cacacacaca cacacacact   4920
cacctatgca gtgagctggc tgggaatgag caggagaggc agtgttagct gcacgagggc   4980
tggctgttct gcctttccga gctcaggcag gtccctcctt tgagggagag atctagggaa   5040
gccagaacag ccaggcctac acaaagactt ctccctaggg gatacaggga agaaaatca    5100
acctagtctt agctctcagc tgcccagcaa tgaaagaaa taagaaaggc agtttgggta    5160
tatggcatct tcagagctcc atgtagggaa tgctctcagg ttggctctcc cagttcccag   5220
tcatagttct tccataggac cagcaaggat gctgcattgc aaggatgcta gccataagaa   5280
acattgacat gtgtatgttc ggaacaggtc tgaagcagtt gacccgtgag ctcaaggata   5340
ctcagctaga ttctttctcc accctgccct accctccaga atactagggg acagagttcg   5400
ttaggcatta ggttcatact cagccacacc ccagagggct agggtcagga ctggtgtgaa   5460
cttgagtgga agaaggccac agtgcctctg gggctaccca aagccctctt ccagaaggcc   5520
aaaatgcctt gtgacccggg aattgtcagt tcctggagat tccaacccct ccttcagcct   5580
gccacctgga tagagataag gctcagggt caaaggctgg aaggctcaat ggggagggg    5640
cacagctggg ggcccagcc ctacctcctt cttcttatgc tcaggcttta gcgctcacaa   5700
cagggcctca aactcctact gctcaactcg aactcttcca agcccaaaa gttggctagg    5760
accaaagtca catctttgtt tcctgtttgt ctaggttggg gctttagcca tttcctgggg   5820
attttccccg agggctgggg gtgggggagc atgacgcagc aagtaccctg cagaaatctc   5880
ccattgtagc ccatattgga cccagcggcc ttagctcagg agccaagagc agcaccccca   5940
ccctcaccca ggctacaaga tttgaatttt gtctaagctg cttgggctga gaggcagctg   6000
gtgaagggtg gagggaagcc taagagctct cctgaaaatg tcaaatagaa cgcccatgtt   6060
tgacttgata acatctacgc gctcaaacct ttaatccccc tagcttctgg tccagtggca   6120
aggtaacagg cgagggtgat ctgggctctt cagggaacag aggaagccct gactggcagt   6180
tcagggtgtg acaggttcaa gccgccacc taaggacagg gacccacctt tagctccagc    6240
cccaggaggc accagctctt tctccccagg cttcggggga ggatctgcca ctggaatggc   6300
taacccagca gccaatcaca gagccctgta ggaaatatct gggagaggtc ttggagctag   6360
ggccaaggca agttgaaccc agctccagtc tggccccgga cagtcccagc tgtctccagc   6420
tagcccagaa gtcagcacct ctacaaggaa cgcttttggg ggcctgaggc gtgatgctcc   6480
caaagtcggt cacacaggga cttgtgttgg ctctgctggt gggcacagtg gcagtggccc   6540
ggcccaggaa cctgctcagc ctgctcgcct tgggccaggg tgctctggat cgcctggaac   6600
tggacggcct gttaaatacg ctggtggccc gtgtgcactg caccgacggg ccgtgtgaaa   6660
aggtaacacc cccacccgat gggtccccca gccccggccc cttcctgccc gctccaccct   6720
gtggcaggca ctaaagagat ctgggcaaac tccaggaggc gggtctggag ctggtgtct    6780
gcacctgctg gcaggctgga gcctcccttc cgtttctggg gggcttatac aggcctgggc   6840
ctccatcctg ggacacacag ctccattccc ccaggctatc aaatttgtgg tgactcacag   6900
tgaccactct caccttcagg atgggggagt aattgctggg gaccccttg tgtaggctcc    6960
tagtcaagct aactacaagg ggcagaacat gacataagat agctgataga atccatgcct   7020
gtaggctatg cctggtaggc ttagtctagc tcagatcctg tctgtttgcc cacagtgtct   7080
gtctgtggag aatgtcttgg ctctaggcaa acctgacaag ccacagcctg ccccagaatc   7140
agtcctggag tccagacaca ttatttacct tagtgctgct gctgccctct accttaacaa   7200
cccagagaaa acatgcaagg acatccaagc tggcctcttg gcctcccatg tggacgatta   7260
```

| | | | | |
|---|---|---|---|---|
| cctggccaca | ctggagagtc | cagaggccat | gaccctgggt | ctgagccagc tactgcagaa | 7320 |
| gattgaggcc | catgctgcca | gccaacccac | cggggagaag | gtgagggccc agacagcttt | 7380 |
| tggggataa | tgacaaggac | cttagtgcca | tggaagggag | gctgcccca caagggagat | 7440 |
| gtcccacgtg | cagcctcatt | ggaggtactt | aggtgggaat | cagtcttgtg cacagttggt | 7500 |
| agaacggggt | ctgcgggagt | ctgggggaac | cctttgggg | aaatgacagt caggagagct | 7560 |
| ctggggccaa | ggtcataggc | cacagtgaag | ggtgtgacta | gctggggcag c | 7611 |

<210> SEQ ID NO 22
<211> LENGTH: 3395
<212> TYPE: DNA
<213> ORGANISM: mouse

<400> SEQUENCE: 22

| | | | | |
|---|---|---|---|---|
| ctaggtttat | ggtataggta | gctggtttag | ggacataggc | tgatgtcttc tgtgaaatct | 60 |
| gggaagtaac | ttgaggaggt | tggagccggg | cagtggtgga | acacgccttt aatcccagca | 120 |
| ctggggaggc | agaggcagat | ggatttctga | gttcaaggcc | agcctggtct acaaagtgag | 180 |
| ttcaggacag | ccagggctat | acagagaaac | cctgtctcga | agaaagaaa gaaagagaga | 240 |
| gagagagaga | gagagagaga | gagagagaga | gagagagaga | gagaatgaac ttgaggaggt | 300 |
| tgggagttga | tgggagaccc | aggcagtgag | gtggactcct | gaagccaata ctgagggcag | 360 |
| agttgaagac | aatctctttt | acagacctgt | gtagatcttc | cccaactgct ggaggaggct | 420 |
| gaggcagcag | gggtttccaa | aagcgccggc | ctggtcttga | ctgccttgct ggatcatgtc | 480 |
| attaatgggt | cctgcttcca | aggcctgcct | agccctcagt | actttgtgga ctttgtgttc | 540 |
| aggctacaca | gtagtgaccc | tcccaatatc | acgctgcatg | gtgaggccta ggctacgatc | 600 |
| gtcagccgct | actcttgggg | aatgggggga | caaggctgga | gctgagcgca ctgactgcac | 660 |
| tgttttttgtt | tttgtttttt | tgtttttttgc | tttttgtttt | ttcttgctag aactggagaa | 720 |
| tttgatgcat | caccttgggg | tgggtggaga | ggaccacagt | gaccatgatg accacggtga | 780 |
| tcatgctgac | cacagtcatc | cggacaggaa | agccagccac | caagactctg agctccatac | 840 |
| tccccacaac | agcaactcta | gtgtatggga | cacggtacgc | cactcatgcc attctggaga | 900 |
| aagaagacaa | ccttccatgg | gtctgttcag | acacctgact | cctgtcctgt tctctttgcc | 960 |
| tccagctgtg | cctgagtgcc | aaagatataa | tggctgtgta | tgggctatct gaagaggctg | 1020 |
| gggtgagccc | tcaggcctgg | gcccaactga | cccctgcctt | ggtccagcag cagctaagtg | 1080 |
| gagcctgcag | cccctacccc | actatccgta | ttcaggacca | gctcagtcaa acagagagtg | 1140 |
| agtcccccgc | cctgggtgct | agcctcaggt | tattgggctc | tagaagggg catgagttgg | 1200 |
| cattgaggaa | tgaggaacca | ctaaaggagg | aagagtagtg | gatttcaagg ctagagggcc | 1260 |
| agagtaaata | gattcctggc | acctgctgac | ggcatctctg | tagagatctt gcccactaca | 1320 |
| tcctgcttgg | ctggacttgt | ggggattgc | ctgtctagga | agcaggggaa atctcagtgt | 1380 |
| agactcaccc | acagggtatc | tctatggctc | gctggccacc | ctgctcatct gcctctgtgc | 1440 |
| tgtgttcggt | cttctgctgc | tgacctgtgc | caaatgcagc | acagccaccc actacatcat | 1500 |
| gcagaccttc | ctaagcttgg | ctgtgggcgc | acttaccggc | gatgctcttc tgcacctgat | 1560 |
| acccaaggtc | agccgtcact | caacagggcc | cccccccc | cacactgccc ttttcccagc | 1620 |
| ctcaatcaag | cctcttgtag | ccctgaagtt | cccccagtcag | tactcgcccc cttctcaggt | 1680 |
| gctgggactg | cacacacatg | gtggagaggg | tcacacccat | gaggaggagg tgggcgttgg | 1740 |

| | | | | |
|---|---|---|---|---|
| tgggcaggcc | acctggcgcc | tgctggctgt | acttggaggc | ttctacatct | tcttcctgtt | 1800 |
| tgagagcttc | ttcaacctct | tgttgcccag | ggaccaggtc | aggctctggg | gaaccactag | 1860 |
| gtgggatggg | taaggtcttc | acaggctctg | accagttttt | ccacaggatt | ctgagaaaga | 1920 |
| tgggccttgt | agccatggtg | ggcacagcca | tggaatatct | ctgcagctgg | caccaagcaa | 1980 |
| tctccgacag | tccaaacaga | cccatgaaag | ctctcgttca | gacttggtaa | gaggcaagtc | 2040 |
| ctatcccaca | ttgagccctt | tagttatgta | tttgcctggg | ttcattcttg | ctcccgcccc | 2100 |
| ggcgccccc | aggtggcaga | ggagacccg | gaactactga | acccagagac | ccggcgactg | 2160 |
| agagcaggtg | agccccaggg | agttcctggg | ggcactgcag | atctggggtt | tgcccttagg | 2220 |
| cgcgtgcaga | acctggccta | caagacccac | gcttgctatg | cccacagagc | tgagactgtt | 2280 |
| gccctatctg | atcacactgg | gcgacgcggt | acacaacttc | gctgacgggc | tcgctgtggg | 2340 |
| cgccgccttc | tcatcctcgt | ggaagactgg | gctggccact | tcattggcgg | tgttctgtca | 2400 |
| tgagctgccc | catgaactcg | gtgagctctg | ggacgtggct | tgaaagggtg | gggcttagtg | 2460 |
| agaagagcaa | tctattctgg | aggtgaccaa | ggccagagaa | aaagggacaa | ggccttctta | 2520 |
| tgagagaggc | atgtgatggg | atggggtgg | agggcgtggc | tagatgtagg | atggattgcc | 2580 |
| ggactgcctt | tgggtgtgtc | tgtctgggat | gtgggtgtga | caggcatggt | gggctgtacc | 2640 |
| tgacctgtgg | gcagagttct | cgctgacttg | ttccgttcta | ggggacttcg | ctgctctgct | 2700 |
| gcatgccggg | ctgagtgtga | agcgtgcgct | tttgctgaat | ctggcctcag | cgctcacagc | 2760 |
| attcgcaggc | ctctacgtgg | ctctagcagt | cggagtaggc | gaggagggcg | aggcttggat | 2820 |
| tctggcggta | gcaaccggcc | tcttcctta | cgtggcgctt | tgtgacatgg | ttagaaaggg | 2880 |
| gaagagcctt | atgtaggggt | ggggagctaa | ccaggggctc | caaccaactg | gcagctgaat | 2940 |
| tggtgccatc | ttttcctcag | ctcccagcca | tgatgaatgt | gcgcgaccag | cggccctggc | 3000 |
| ttcttttcct | gctccacaac | gtgggtctgc | tgggcggctg | gaccgtcctg | ctgctgctgt | 3060 |
| cattgtacga | agacaacatc | accttctgac | agctctatcc | catcccagtc | cttgtccctg | 3120 |
| tctgttgact | ctgctttacc | ttcttaagcc | acctaattgt | tggccccact | acgggtagcc | 3180 |
| agaggctttg | agcctcattt | ccttgctctg | acttcaataa | agacttttca | atcaaaccca | 3240 |
| actacactgt | cttcttgtag | agtttcctgg | tgaaagctct | ggggcaggcc | actacctcca | 3300 |
| tcttcagcgt | ttgctatgga | cggctccact | gggggtcctg | tggacagcca | gattgtcttt | 3360 |
| cctataatca | aacctgggga | acggtcagag | ttctc | | | 3395 |

<210> SEQ ID NO 23
<211> LENGTH: 6209
<212> TYPE: DNA
<213> ORGANISM: mouse

<400> SEQUENCE: 23

| | | | | | | |
|---|---|---|---|---|---|---|
| caggatctga | tggggtcctt | gtctcgagtc | aaaacattac | caacgttgct | tacaaatatg | 60 |
| agggagggct | catttctgcc | atgaagagaa | gcctagaaat | gatcaaacca | aaggacaacc | 120 |
| tgttaatgtg | gagctctcgg | cagaatcggc | tattccaaat | ccccttgcat | tagcctttgg | 180 |
| aggttgacat | aattgtctac | cctagactag | gtgccgaaag | agcagaactt | tattctctca | 240 |
| gttctggagg | ctagaaaacc | aaaggcaagt | tttcaatcag | gcaaaagcaa | tgaatctggg | 300 |
| gggctggaga | gatggttcag | tagttagaag | cactgactgc | tctttctggg | gtcctgggtt | 360 |
| caatttccag | caaccacatg | gtggctcaca | accatctggg | atctgatgcc | ctcttctggt | 420 |
| gtgtctgaag | actgtactca | catatgtaaa | ataaataaat | ctttaaaagg | aaaaaaaaaa | 480 |

```
aaaaaaggtc tgggttccca aaacatttca gcaggaccaa cagtttttact tttgcaagaa    540
gggtgtgcag ctgtgctaaa ttaagcaagc aagtgagcat gttcatagaa ggtattgatg    600
ggttttaca atacttaatt aaaagggtc cagtctcaat gtgtggttaa agcttagcct    660
catattcctg catggttgac tggcaaatgc agaacagggc aggtgctagg gagaggtaga    720
cttgaactgt gctaacggtt aggccaggca tggaggtaca tgcctgtaat accagcactc    780
aggaaggata gaggcaggtg gatttctgcc aattcaggcc tgcatgcttt ataacatgag    840
ttccaagcca gttgaagcta catagcatga gtctgtgtca aaataaataa aaatttaaaa    900
ataaaatttt tcagggtagc tggagctatg ttgagagata ggacgttgaa tttaccaagt    960
ggttgcttta tttgcaatgt ttgttgtctc tgtttacatt ttgagatgta tgtcttactc   1020
tgttttgttt ctttggttgg cttctctaga cagggtttct ctgtgtaact cctgctgttc   1080
tggaactata tagaccaggc ttgaactcat gagatgcacc tgcctctgct tccccaatat   1140
tgggttaaag gaatggacta ccaccgacca gagttgctgg gcaacgggaa ggggagggca   1200
ggctgtcctc atcttgtttg ccttccgctg gtccacacag ccctgaagct cctcatcttc   1260
ttccagcttc tgagacagtc tgtcagcatc atcctctaga agagtaaagt ctgctgagcc   1320
taagcctagg gtgttctagc tcccctgatc gctagggcag agcagccacg agcaggaagg   1380
aagattctag ggtctgggag ctctgtagcc aggtaaagca aagctgactc ccaaccgaac   1440
tccaccagca gctggcttca attagttttgt ttagttgggg ggggatttgt ttgtttgttt   1500
gtgtgtttgt ttttagatgg gggttctcct cgtaccctg attgtcctgg agcaggcaga   1560
cttgaactca gatcagactg cctctgtatt ccagtgctgg gagtaaaggt gtgtaccacc   1620
accacccagc tatcattata tatttttgat tagcttggaa ctcaaccaaa ccagccagag   1680
cttttgtactt ccagagatct gcttgcctct gtattataag ccctggggaa gggcacggct   1740
cttaccccca gagagatcac tacaacaaag caaagaaatg acttcacaaa agtccaactt   1800
ggcaaactac tactacgtaa tttaatgagt ttattattaa taaattatta ttattaaatg   1860
agtttattgg gtctacttac agcagaagag gtaaagagtt atattacagg agaatgattc   1920
aaaagcagcg gcattatcac aaagctcacc caggagctgg agagatggct cagctgttaa   1980
gagcacagac tgttcttcca gaggccctga gttcaatccc ctgcaaccac atggtggctc   2040
ataaaacatc tataattgga tctgatgcct cttctggtgt gtctgagggc agctacagtg   2100
tacttgtata cagaaaataa ataaataatt ctataggact tcaggcaggc agatctctga   2160
gttccaggcc agtccctgta gccagcacag tctaggctaa ctgagatatg tctgggaaa   2220
aaaaaacaac caaccaacca aacaaacaaa caaaccaacc acacaaagct ctccctgcct   2280
gtatgaccac tctcacccca gagctgcagg tgttaagagc tccctctggt agtttcggga   2340
attcttgaac cttctactgt ttacttctgg agtctttttt ttttttttaat ttatttattt   2400
attatatgta agtacactgt agctgtcttc agacacaccc gaagagggggt tcagatctca   2460
ttatgggtgg ttgtgagcca ccatgtggtt gctgggattt gaactcagga ccttcagaag   2520
agcagtcagt gctcttaacc actgagccat ctctccagcc ctacttctgg agtcttaaga   2580
acctgtctcc aggaggaatg ttgatcaatt tcttcataac tcagagtctc actgggtcac   2640
cagactggcc tcaaatgtgc atagtccttg agagtgctgg gggtttacat gtgacgtatg   2700
atgtcacagg tctattttatt tatttatta tttattttatt tatggtattt ttcaagacag   2760
ggtttctctg tatagctctg gctgtcctgg aactcacttt gtagaccagg ctggccttga   2820
```

```
actcagaaat ctgcctgcct ctgcctccca agtgctggga tcaaaggcat gcaccaccat    2880
gcccggcttt tttgtttgtt tgatgtcaca gatttttttt ttttaagatt tatttattta    2940
tttattatat gtaagtacac tgtagctgtc ttcagacact ccagaagagg gagtcagatc    3000
tcgttacaga tggttgtgga tggttgtgag ctaccatgtg gttgctggga tttgaactcc    3060
ggacctttgg aagagcagtc agatgctctt acccactgag ccatctcacc agcccgatgt    3120
cacagatttt aagagtattg ttttttcaaga ttttttttttt tgagacagga tttctctgtg    3180
tagcccagaa agatttttat tttaaaaatt atgtaggact ggtgagacat tactcagcag    3240
ttaagagcac tggctgctct tctgaagatc gtgcattcaa atcccagcga ccaggtggtg    3300
gctcacaacc atccgtaatg aggtctgact ccatcttctg gtgcgtctga agacagctac    3360
agagtactta catataataa taagtaaatc tctggggctg gagtaagcag aggttctggg    3420
ttcaattccc agcaaccaca tgatggttca caactatctg tacagctata gtgtatcata    3480
tacataaaat aaatatttaa aaaattatgt atatatgtgc cagcatgtct gggcagcttt    3540
cgtcccaggg cttgggaggt agactctgaa ttcgaggcta gttgggtcta cagagtttca    3600
ggacagccag ggctatgtag ttgagacctc atctcaaaaa tcaagaaaaa gaaaaaaaaa    3660
taatttcttt tgcttgcttg ttttttgtttt ttgtttttgt ttttgttttt ttttaagaaa    3720
agttttctct gtataaccat ggctgtcctg gaactcactt tgtagaccag gctggcctca    3780
aactcagaaa tctgcctgcc tctgcctctg cctcccaagt gttgggatta aaggcttaca    3840
ccaccactgc ccagccaaca aaatactttt taaagagat cttttttttt aaattttatt    3900
ttatttttat taggtatttt cctcgtttac attttcaatg ctatcccaaa agtccgccat    3960
acccaccccc ccaatccact acccacccac tctcccgttt tggccctggg gttcccctgt    4020 actgggcat ataaagtttg caagtccaat gggcctctct ttgcagtgat ggccaactag    4080
gccacctttt gatacatatg cagctagagt caattaaaaa gagatcttta gtgtgataca    4140
ggggtgatct accacatcac ctcatctaca gagtggggtg gcgatattgc atgtttctgt    4200
atccttttcc aagcctatat acccttgttt tattttctgg gatttagcta atgaggcaag    4260
tcttgaaggg tacagaacag aaggaagcag aggtccagca ccctccagct ctgtgacgag    4320
gctcatcagt cctttttttt tttctttctt tctttcttgt ttttttttt cgagacgggg    4380 tttctctgtg tagccctggc tgtcctggaa ctcactctgt agaccaggct ggccttgaac    4440
tcagaaatat gcctgcctct ctcaagtgct gggataaaag gcatgtgcca ccacgcttgc    4500
tcgtcagttc ttatcaagct aggccactag gggccgctct tcgctcgcag ccacggcgcg    4560
caggcgcaga tgcgaagcgg cccggaaccc tgcttctcaa ccacctggtc ctcttagaag    4620
gcggtccggg caggaagcgc aggcgcagta cttcggaacc cggtggctgg gttggcgcgc    4680
gcggccggac cgagtccgct gccgtccctg tcccccgagt cggcggctcc ggcgtgacag    4740
tggcggcgac atgtacgcgg tgtacaagca ggcgcacccg cccaccgggc tggagtttac    4800
catgtactgc aacttcttca caacagtga gcgcaacctc gtggtggccg gcacctcgca    4860
gctctatgtg taccgcctga accgcgacgc cgaggtaggc cgtgtcgagg cagtgccgca    4920
gtcattcggc aggttcccca gtgcaggagc tgaggtttgc caagggtctt tgggcccag    4980 agccagttca tcgctgcctc gttgtttggc ctcatcctac cctgcccgga cacctctgcc    5040
cgcggtctac tgcttgttct ttggagatcg attttcagga gattgttgca caccttccac    5100
gagcttagca gcaaagacaa gccagtgaac ccttgagggc gatgattctt taggaagtca    5160
atactgccac acacagacgg ccacagtgtc tctctaggag taagacccaa tgaaggagac    5220
```

```
tgggtgtttc tgtacaaaac aaccagagct ctttctgaga ttgagcagat ttgttgtgga    5280
agaacgtttc ttcctaaagg agcaaggctg gatgttctc ggggacagac tattgtcagt    5340
agatgtagta atgtggaatg aattcatcag tacattgata acggggtgt tttggttgct    5400 agagagacag caagcggttc aggaagccct cccccctcc ccccaaaaaa aaggcaattt    5460
ccgtggctct ttaatcccag ttcgatccat taatcccagg tggaagcaga cagatttctg    5520
ggtgttccag tttaaactat ttccaagcca tctagggcta catagtgaac ctcttgtcta    5580
aaaacaaagc aaaaaagcca agaaggcaga tgcttttttt aaaaaattag acttattcat    5640
attcatttgt gtttgcttgt atatatgtat gtacaccata tgcattcttg gtgtccatgg    5700
aggtcagcat tatggatagt tgtgccatca agtgggtcct ctgtaagagc aacaagtgct    5760
tttgatggct gtgcattact gccaacatgc agtttactgg ggtggcagaa ctggacaggg    5820
aaatctcacc ttcatagaag atgtgtttta aatagacaag gaagtgtggg ggaagtatgt    5880
gggagttagg caaggggtt tcaaggaaag ttaagttttt gtggtagagg ctaagggaag    5940
gaggaaggaa gggaaagaac gggtaagaag taacagggca gggcctccac aacacactct    6000
ccaagcagga agttttggca atgaaataat cttacccaac ttatgttgga gagaggtcca    6060
agaaagatgg tcaagaagtg gctgtagcca ttaggcaaga tggtggcctg gaccagtgca    6120
gctatgacag ttcaggattg atagaggtgg agtttgaaag gagctcaagg taatgccaag    6180
aatctgtcac tgttctgggc aacaggtct                                      6209

<210> SEQ ID NO 24
<211> LENGTH: 9766
<212> TYPE: DNA
<213> ORGANISM: mouse

<400> SEQUENCE: 24
gctggcatgg tggctacttt tctgttgctg tgataaaaca ccaagaccaa gtcaacttat     60
gggagagacc gtttgtttag gcttacagtt tcaaagggtt agagtccacc atggtgggtc    120
accctgacaa taggtgccaa gctgaaacag tgaacgaaat ctccacaccc acccatggtg    180
acatacctcc accagtatgg tcgcacctcc taaacctccc aaaccatgcc caccagccaa    240
ggaccaaaca ctcagctgca ggagactact gaacagctca ttcaaaccac agcatgctcg    300
ctcgctcgct cggcatttga gaggctaaga tgggaggagc ctgagtttag gccagcatga    360
agacagaaac cccgagacaa aggaaaagaa gagaaaagac aagaggggct ggagaggggg    420
ctcatgggtg aggggctgga gagggctca ctgtaaggaa gggcacttgt tgctctcacc    480
caggaacaga gttccatttc cagcacaatg tgcctcacac cctttgtagt gatcttccgg    540
atcttctggc ctccccggga accactcaca cagtgcacac acatgtctgc aggcaaacca    600
catattcata agataaaatt aaaattcgtc tatgcatgaa tatacacatt aatataaata    660 ttttttaat ttaaaataaa tttaaacatt ttttcaagga tttatttatt ctatataagc    720
acactgtagc tgtcttcaga cacaccagaa gagggcacca gatctcataa cagatggttg    780
tggccatgtg gttgctgtaa tttgaactca agacctctgg aagagtagtc agtgctttta    840
atcactgagc catctctcaa gccccaaatt tatggatccc tgagttcgag ccctggtct    900 acagagtgag ttccaggata gctatggtga cacaagaac ctagtctcgc aaaaacaaac    960
aaacaaacaa tgaaaatatt aaaataaaag cagcctaaac aacacgtaca tttatagct    1020 atatctcagt agagcaaggg aaggcgggtc cggggagagt cagagagctg ccaccccagc    1080
```

```
acatgctggt ggaaagcctt cctgtggact gggctgctct ggcgcctggc gtttcttctg    1140
tagggtcctt cccttccgct cctcagaaga gccctcacca ggtggcaagt caaatgtcca    1200
cacaaaactt cagacaaaaa gtgttggctg tgctttctca tctacagcca aggttccaga    1260
ccccgagctg tgcaggtgga gccgggcagg gtccacccct cctctcccag agtcagggat    1320
tctgtctctg cagggcttga ggcctggcca ctccagactc tcctttactt gagattctgc    1380
tcgatctccc tgtcacttgc agagaactaa tcagggctg ggatgggagt ggggtgagag     1440
tgccttccta gaattctgaa gggaagggtc taggggccgg gctcagtggc agggctcttt    1500
acaaacatgt gaatctatgg attctatctc caagccagca aaaagttaaa ttaaaaatcc    1560
tgaatttggg ctggtgagat ggctcagcag gtaagagcac ccgactgctc ttccgaaggt    1620
ccggagttca atcccagca accacatggt ggctcacaac catccgtaac gagatctgac     1680
tccctcttct ggagtgtctg aagacagcta cagtggactt acttaaataa taaataaatc    1740
ttaaaaaaaa aaaacttta aaaaaaaaa aatcctgaat tttagtccag tgatggtggt       1800
gcacaccttt aatcccagca ctggggaggc aggtggatct ctgtgagttc aaggacagcc    1860
tgggctacag aaagagttcc aggacatcca gggctacaca gagaaacctt gtcttgaaaa    1920
accaaaaaac aaacaaagaa aacaaatcag acccgggaca aggggctggg tgcatattta    1980 acatataccct ccaggttctc ccagcatccc gcagcagtcc ctacctagta cagggcacgg    2040
ttagcatata ctgccctctg ccctgaattc ccagcctag cggggctgc ccctccccca       2100 gcagctcttt cccagataag cctggcattt tgctctctcc tctctctctc cccctctctg    2160
caccatgctt tcttttctct ctgcctccgt gggatcagtg aacccacctg agaacggctt    2220
cccaataaac ctaacctgcc tttatatact ttaatttgcc tcgaattggt tggtgttgtg    2280 ggtgagaaa atagcacttc gtcctgcatg gatgttttgc ctgtatgcac gttggtgcac     2340
tgctttcttg ccatgcctgc tgtcttccga ggagaccaga agcaggtgtc agattcccgg    2400 gagttgccttt gtgggtgctg gagacaaacc gggctgtcct ggaagagcgg tcagtactct   2460
taaacagctg acccttctc cagccccctt tctcctttct tcagtgtggg ttttttgcttt     2520 tgtttggttt tgacagggtc tcctgtagcc cagggtggcc tcaaactgac ttgttgccaa    2580
aggacgctga actcctggct tccaactgcc aagttctgga atgaccagta tgcaccacca    2640
ttctaggctt tccacatctt tatctgctag tccggctggt catgggaggt caggtggctg    2700
agactgagta aggcaaaggg gcttcagaag gctgcgggcc atgtagggtc agggaagaat    2760
ctagaaagcc agacctggga ggaggcgagg cttcactgtg taaacacagg gcagggcttc    2820
ctggccaacc tgaaatttcc cagaggccca aacatgaggg gttaggcatt ccactcagtc    2880
cagctctgtt tgttttgacc ctaggagcct tgatgccag ctggcagctc tcctgcccta     2940
accctcattc tgcacgtagc ttggaaaggt ctctccctgg aggctttagg attctgggta    3000
cttagttctg aggcccagcc tctgagaggc agctgccgct ctgtgtaagt gggtcaccag    3060
ggtcatagtg acttcctaat gagtcctgcg cctggactca cctttcaccc ctgcccatgg    3120
ctctggcctt cctggacatt cccaaagccc ctggcatagt gtgcacaccc tcaaaggagc    3180
tactcaaagg actcctgaag ctgttgccaa agccctcctt ggctcccatc tcccacttaa    3240
aaataattta ttttatgtgt atgagtacac tgtagctgtg agcttcgtg tgattgttgg      3300 gaattggatc taggacctct gctcgctccg atctcagccc cgctccctca ggcccaaaga    3360
ctgaggtcct ggccagcctg gaattcacta tataaactag ctggcctcc aactcacagg     3420 agatccacct gcctctgcct ctgaaatgtt aggattaagg cttttaattt cagcaaagga    3480
```

```
gtcagaggct agctgggtct acatagtaaa ctccaagcca gccaagtcta cccagtgagc    3540
acctttctca aacaaacaaa acgcaaaaat tgtgacaaaa tgtccacgcc acaaaataag    3600
cttaaaacaa caacagagcc aggcagtggt gtgtgtggtg gcatatgcct ttaatcccaa    3660
cacttgggag gcagaggcag gcaaatttct gagttcgagg ccagcctggt ctacagagtg    3720
agttccagga cagccagggg ctacgcagag aaaccctgtc tcgaaaaacc aaaaaaaaaa    3780
aaaggcaaaa aaattttttt taattaataa ataaataaga tacgctatgg aaggggagat    3840
ggctcgattt ttagggtgct tgctgcattt ccagaggacc acacttcagt tctcagtacc    3900
atatcaggcc cataatgcca actccaggga acaggtgcc tgcctgctct atcctctgta     3960
gcacttgcat tcatgtggta cacacacaca cagccatact tacacataaa taaatgaata    4020
aataaataag taaatactta aaaacacaga gacatactta cacataaata aataaataaa    4080
tacttaaaaa aaagttattc caggcagggt ggtgcacacc tttaaactca gcacttgaga    4140
ggcagaggca agcagatttc tgagttggag gccagcctgg tctacagagt gagttctagg    4200
acagccaggg ctacacagag aaactctgtc tggaaaacac acacacacac acacacacac    4260
acacacacac acacacactc acacacacac acacacacac aaattatttt atttatgtga    4320
gtacactgtt gctctcttca gacacaccag aacctcatct gtaatgggcg tcagatccca    4380
ttacagatgg ctgtgagcca ccatgtggtt gctgggaact gaactcagga cctctggaag    4440
agcagtcggt gctcttagtc actgagtcat ctctctagca cccaaataaa tactttttt     4500 ttttaaagat ttatttattt attatatgta agtacactgt agctgtcttc agacacacca    4560
gaagagggca tcagatctcg ttacggatgg ttgtgagcca ccatgtggtt gctgggattt    4620
gaactccaga ccttggaag agcagttggg tgctcttacc cactgagcca tctcaccagc     4680 ccctttttt  tttttttttt tttttaata ttaaaggctt cacgaatttt cgtgtcatcc     4740
ttgcgcaggg gccatgctaa tcttctctgt atcgttccaa ttttagtata tgtgctgccg    4800
aagcgagcac aaataaatac atttttgaga taggaccttg caacttagtc tagaactggc    4860
tacgtagcta gagcccaagc tgtcctcaaa actcagatgc ctgcctcgcc tctgcctccc    4920
gatgttgggg ttagaagcct gcgccacagt gcacgacctt caaatataat ttgttttga    4980 ttggtttggt tttattcggt tttggttttt tgatacaggg tttctcttgc agctctggct    5040
gtcctggtgg tacacactct atagattagg ctgtccacct gctttgtgtc tcccgagtgc    5100
tgggatataa aaggcatgtg ccaccaccaa caggctgaaa tgtaagggtt ttttgtttt     5160 ggtttgtttg tttgttgtt tgtttgtttg tttgttgtt tttgaaaagg acagccgagc     5220
atcgtgggtc aggcatttac cccagcactc catccaaagg cagaggcagg tggatgtttg    5280
agttcgaggt cagcttggtc tacagagtaa gtttcaagac agccagggct acacagagaa    5340
accctgtctc aaaaagagac agaggagaga gaggggtag agaagagcgg ggataggga     5400 gaaaggagag gggagggaa agattggggg taagggaggg gggagagag ggagagcacg      5460 agcgaggcga gagcgcgcgc gcgcgagctc aagggcagtc caggctccag gccccacccc    5520 ctcgaggtg tggcctgtgt ggtcacgtgc caacgcttct ccacccgctc cgctcctgta     5580
gcgcgagcga gagcggcgga cgctgggtac gtgcctactc cctgtgtgcc tggcgccccg    5640
ccctgcgacg ccgcgtgcgt gcgtacgtgc gtgcctgcgt gcgcgcgccc cgcccttctt    5700
atagagccgc agtggggcag ctcctggacg aggcgacatg gcggcggcgc tgctgctggc    5760
gctggccttc acgctcttga gcggccaagg cgcctgcgcg gcgggtaaga gcggggtgct    5820
```

```
gggaccgggc tggggtcacg gacttaaggt gagcctccga tttcggggac tcggtggttc    5880
cctactcggg ctcgaggctt ggagattgtg gaggagtaac agtggctgtg ggtgaccctc    5940
gagttgaacc tagcctcgac tgggcatcga ggtggagggg agtgatctta gagatgaggc    6000
cctggagaga caaatcaaag gttaggactc tgggggagac gtcctaaggt tgtgggaacc    6060
ggaggtggaa ggagccgcca ccttgtggtg gtccccacca ggacatgggc tggaaggtaa    6120
tttggatgga tttggattac agaagtgaat gggatgaccc cagattttgg tcagctggag    6180
atggaaggag ccgcttccct aactgtccca gctcccggaa tagggctggg acgtgaccct    6240
gaaggtttgg ggatacaaca atgactataa ttggcttagg ttttggggag ttagggaagg    6300
tgtgggaaga ggtgaccctg acgctggaag acagtaaggc tctgggcaa catctccaac     6360
gtgagtgagg gcgtccgtgg ccagggagct gtctggacca tcttggtgtc tccacctgcg    6420
taccagggct ggaacggaac cctagtaatt tacctcctcc tggtgttggg gcctgggaga    6480
gtgaagataa agaagtcag cacgttgagg gttccacacc tgagagacag ggctggaaag      6540
taaccatggg ccagagggac atctggcagg acatctgaga gaggtttgtg ggaccctgggg   6600
tgagggacag cagtgttgca ggtggcttcc tccaggattg agagatctg gggactaaag     6660
aagctgccac cttggggaga tcccaaattt ggaagacctg ggagtcgaag gaactgcagt    6720
cttggtgtcc ccactcaggg aacagagtga gggtcacagt ccctaattta ggagggcatg    6780
gagttagaga ggtctgttac tttagtgtta ccatctgggc aaggggagga tgcgaaatag    6840
actttcctac aaaggctgtc tccaaggttt ggggtcacta gggggactag agtaggagga    6900
gctaccattt cagggtgtcc atacttgggg gaccaggcag ggagatgatt cagagggttt    6960
ggggtacaga agtgcctggg gagaggtcca caagtttggg catatgggtg gaagtgaggt    7020
gactaggaat ttgggggagg tccttgatgt ttggtgatgt gaggggggatg gagaaaggat   7080
tggaaggtct cagtggagga agctgctgca ttgctgtttc tacttagtga aggagcacag    7140
cattgcttgg ggaatgtgaa agaagaggat gaagttggtg ggggatagca ttgcctatta    7200
gtaatgtcct caggtctctg gaggatgtgg attggaaagg gggtgagagg tgaccccgtg    7260
ggttcttggg gtaaagaggt gcccaggat gggtaggctt ggagggctgg ggatgagtgg      7320
actcgccctc acatgtgagg gttgggtgag gagttcctga gaggcagttc ccgcccctag    7380
gtttggagga gtccttatca gctgtcccca gctgtccctg tcctccttgg ggtgagcttg    7440
caggttctcc atagtccaca ggggctgtat ccctgtaatg gccacctgtc cctgcccctc    7500
tgggctgagg cagagcttca ggctggtcta ggagttccct gggagccagt gcctgcgaat    7560
ggctccggac cccaggctca ggcacttgct ggattatcat tcctggtggg atttctggtg    7620
gccagggctc tgcacactca gcttgctccc accctggagt ctggcccatt ctggccttag    7680
atccttgcct gatgaaggct caaaagggca gctgaggtag gaaggcaggg attcagggtc    7740
atggcaaggt tgaacatgtg gtaggcctcg aacacatggg gactgctctc ctgccctctc    7800
cagacagcag gcaaagggca gagccagagc tccactggag aagtgggcca tgtgactgct    7860
gcccccatca gcaggtacag gaggggctgt ccctggcagc agtgcccggc gttaattctg    7920
acccactttt tccaggccct cttcttcacc atcaaaacat cttgaggtgc ctccatgagg    7980
ctggctcttg gtgcagatag ctgtcccctg gtgagatgga ggcagttgat ttattctgtc    8040
ctgggtagga agcctggctg ggcacaggcc cagtggcttt ctgcctgggg ttaaacagac    8100
cttttgcaatg cccgggagcc aagcacagag tgtagcttac gggcaggtcc taacctttcc   8160
tgggaacaga cccatagcct acagcctggg cagggcccag gtcaaccagt gatgtgtttc    8220
```

| | | | |
|---|---|---|---|
| ccactatgca | gtgggggagg | ggctctgctc | agagggctac | cctgtggcat | ggacacttaa | 8280 |
| ggtttcctga | ttatgaggct | gaatttgata | ttagggtctc | ttcaggctgc | tccaagcact | 8340 |
| tcacaccctg | atttcgcatg | cttgctctga | gtgagtgact | aggctggcct | ccctggctag | 8400 |
| gccaactcag | acactcactg | cagggtgtta | ccccagcgct | tacccagatc | taatttaacc | 8460 |
| ctaataattc | ctcaggcttc | tagatgacat | ggtgagagag | gtgacaagcc | aacagcctgg | 8520 |
| gtcagcactg | gatagcagga | gactgcctgt | gggctgccct | ctagaacagt | gcccccctcc | 8580 |
| ctccctgcac | cctgtggtgc | tggcttgttt | acccaatgcc | tcaggctggc | cctgctctca | 8640 |
| cctgtctgcc | agtaggcagg | aaggaggggac | tgtggggaca | tgctgcaagc | tgtgggctac | 8700 |
| aagtcacatg | ccaagctgt | ggaggctcct | ggggttggga | tcatagttag | tggttacccc | 8760 |
| taagcaatgc | tagctaggct | ccgtgtggga | aggttggaca | gatgtcaagg | gagtaccaca | 8820 |
| gggcaccctg | cattcctgag | actagattat | gggtcattta | gttggtccta | aaagggctga | 8880 |
| aatgtggcca | ttaggcgcat | ggtccttggg | aacatggtag | ccatgtccca | gactgatgac | 8940 |
| acccacagta | tagtgtctct | tcagaaacct | agctggggct | ggggtcttca | gggcatccgt | 9000 |
| ctttcctgac | agtcctagat | ggagtggagt | tgatacagac | atcctggagc | agtaaacagg | 9060 |
| gaagggggact | aagggaaagg | gcactcactg | ctgtggcctc | ctcctgactc | agcctaccca | 9120 |
| cgtgcctgca | actgcaggtt | gggcagtccc | acagatcgca | gctctggaat | gtaggttacc | 9180 |
| aggaaacctc | taccaaagct | gctgtgtcgt | tcataccca | ggggccttga | ggcctcccag | 9240 |
| gctctaggtg | tcactcttgg | tcctggagct | tatcctgctg | ccatcccacc | ccccacccc | 9300 |
| cactacaggg | cctaaagcct | aagcctaaac | ccatatactt | gtacttccag | acagcaacca | 9360 |
| caccttgtgt | aggcatgcaa | agacctgcct | tcccacagga | catgtgtttg | gggcaggcat | 9420 |
| acaggtctga | gtgttccagg | tccctatgta | atactgagag | gccctgtctt | gaagtatttg | 9480 |
| tttgttttttg | ttttttctt | ttttggagac | aactttaaac | acatagccca | gctggcctgg | 9540 |
| aactcctagc | aatcctcctg | tatagacctc | ctcctaagtg | gtgggattat | aagcgagcca | 9600 |
| caacacctgg | cttttactct | gttttcgttt | tttaattaca | tttcgtgtgt | gtgtgtgtgt | 9660 |
| gtgtgtgtgt | gtgtgtgtgt | gtgtgtacat | tagttgcaca | caggtacttc | gccgcatggg | 9720 |
| tcttggggtt | ggactgcggc | tttaggcttg | gtggttacca | ctttta | | 9766 |

<210> SEQ ID NO 25
<211> LENGTH: 3512
<212> TYPE: DNA
<213> ORGANISM: mouse

<400> SEQUENCE: 25

| | | | |
|---|---|---|---|
| cagccctttg | tgttttgttg | tctacctaac | ttcatacttc | tccccgcaag | cagaaaagaa | 60 |
| atggagtttg | ctgtgttgtg | ttggcccctg | tggcaggccc | tggtggctgt | ccttccttgt | 120 |
| agtaacgggt | actaaccctt | tcccatagct | ggtttcctca | aggcaccact | gtcgcaggag | 180 |
| cggtgggcgg | ggggcagcgt | ggtcctgcac | tgtgaggctg | tgggcagccc | catccccgag | 240 |
| atccagtggt | ggtttgaagg | gaatgctcca | aacgacagct | gctcccagct | ctgggatggt | 300 |
| gcccggctgg | accgtgttca | catccatgcc | gcctaccgtc | agcatgcagc | cagttcgctc | 360 |
| tctgttgatg | ggctcaccgc | agaggacaca | ggcacttacg | agtgccgggc | cagcagtgac | 420 |
| ccagaccgca | accaccttac | tcggccaccc | agggtcaagt | gggtccgtgc | ccaggcgagc | 480 |
| gtggtggtcc | ttgaacgtga | gtggccaggg | cacctgtttc | tgtttacctc | tcgtgccacc | 540 |

```
caaccctggc tcccactttg tagaaccaga tgctgctctg ccctaccact cattgagact    600
cccctgggca cacgggtgag ctgaacactc atcagtgtcc ttgctgggtg caggttggcc    660
ctgccctctt ccaggtggct cctcggttcg cacccaggc ctttggtctg ctgtgcaccg    720
ccctgacctc ccgtcctgct ctgctccatg cacctgctct cctgcctccc ctgcctcccc    780
tgtgattgtc tggcaggggt ggggtctgct gcccaagtgt tcgctctgac tgtctactgc    840
aaacctgaaa attccagcca gactttgcag agccctctgg gggtttagtg tccagttctg    900
agtgacggtc agataacagt gaggggacca catggctgtg ggagcagcag gcggggcttg    960
ggcagctgcg tctcttatct tgaagtggtt tgtagtgcag catcagcttg ctttagccgt   1020
ctggggctgt agactgtcag ccgctgtgat tccaacagca gacctcacag agtggggctg   1080
actactatgc tgagcttata ctcttttctcc ctgtggcttc agcgggcacc atccaaacct   1140
ctgtccagga agtcaactcc aaaacacagc ttacctgctc tttgaacagc agtggcgttg   1200
acatcgttgg ccaccgctgg atgagaggtg gcaaggtact gcaggaggac actctgcccg   1260
acctgcatac gaagtacatg tgagtccaca gtgctcaaag daccctgtcc tgatgctgtc   1320
catggggacc tgcctccatc ctgacgtgta gcagtgccag gctccacaca gctctggatt   1380
ggctgggtgg ccttacctgt atagcgtgag agagcccaag gccctatgat ctgcacagag   1440
agccctggtg gggaggtggc caccatgcct tgggagttcc ttacctcacc gaggctctgt   1500
cccctgcaga gtgacgcag atgaccgctc tggggaatat tcctgcatct tccttcctga   1560
gcctgtgggc agaagcgaga tcaatgtgga aggtaatctg tgggagtggt ggggcgggc   1620 caggaggtgg ctggcgtgaa ggccagggac tggtgttggg gctgagagca gtctacaacg   1680
tgcttgggca tcagggttct catcctcaca gggccaccca ggatcaaggt cggaaagaaa   1740
tcagagcatt ccagtgaggg agagcttgcg aaactggtct gcaagtccga tgcatcctac   1800
cctcctatta cagattggtt ctggtttaag acctctgaca ctggggaaga agaggtaagg   1860
gctgtgaggc taaggacatg gagcttgagt ggtgccaagg accaggctgc agtgggagca   1920
tgaggttctg gacatggggg taggggaggc ggcagaaggg gcaccgggtg ctaggaatgg   1980
gagtggggat aagagcatca gaggggacac aggagaggac gctttggtgt ggggatctgg   2040
gacagtgtag gacagactct agcatgacat gacaagccct tctccctagg caatcaccaa   2100
tagcactgaa gccaatggca agtatgtggt ggtatccacg cctgagaagt cacagctgac   2160
catcagcaac cttgacgtaa atgttgaccc tggcacctac gtgtgtaatg ccaccaacgc   2220
ccagggcact actcgggaaa ccatctcact gcgtgtgcgg agccgcatgg cagccctctg   2280
gcccttccta ggcatcgtgg ctgaggtcct ggtgttggtt accatcatct ttatctatga   2340
gaagaggcgg aagccagacc agaccctgga cggtgagcag tcctgggtct gggtgagtgg   2400
gtgggatgcc ctcagtgtgt ccacctggag gagagtgggg tctgcttgta gctcaccctc   2460
ctccttcctc catcacttgg ccacaagctg ctgtcctctg gggagctcgc tgtgaggact   2520
tggggctgtg ggtgcctcta gctgtacact gcatggcgag ctggggtagg atgtgttggc   2580
ctcaccatgt gttgatcatc tgatgtacga cacttctgca gcaccatgag ggtggcagtg   2640
tggggccaag ttcacacgag ccctgacaca tgtcctttct ctttcatgtg gctgctcctg   2700
gctgcagagg atgaccctgg cgccgcccca ctgtaagtcc agccactgtg ggctctgggg   2760
agctagctgt gtgtcctata gaaatggggg atgctctggg actcaatgtg tgtgtccatc   2820
tttcataggc ctcagtaagt tcaggaagg tggatggctg ctgttgaaat aatgccaga   2880 tttcagtggg gttgaggcca gccctgtgcc tgttaagagt aatgagccct gttttgtatc   2940
```

```
cccaggaagg gcagtggaac tcacatgaat gacaaggaca agaatgtacg ccagaggaac    3000
gccacctgag tggtggggca ggcgggggag gggaggtgcc cagggtgcct gaccccaggc    3060
cagcgtctac ctccactcca gtatcccatc ctgtcccgat ttgaacctac ccaacccaac    3120
ctatcccaac ccaagtgaag acagagcctt accttacaga aaacccacct ggaagaagca    3180
agccacttgc agcccctgtt tctaatttaa actaaatgag gtttctatgc agacaatcca    3240
ttccttaggg gtttatgttt ttatttttcc ttcccttctg aagtgttgtc actacagccc    3300
tgtggagtgg gggaatgggg ccttgtcctt ggtcaggagg aaggccagt gcatgctctg      3360 acttactgtt ggagggggct gggcctgctg aaccccccc aataaagac ctaccccacc       3420 atgtgtgtgt cactacttga aacttcagga ccccatctta aagggagaat gagtgttgag    3480
gtcatataca ggaggggttg ttgatcagca cg                                  3512

<210> SEQ ID NO 26
<211> LENGTH: 4575
<212> TYPE: DNA
<213> ORGANISM: mouse

<400> SEQUENCE: 26
ctggggcaca ggtaagtgca tggtccctag accagtggtt ctcaaccttc ctaatgttct      60
gaacctttaa tataggatat ctggtgtgac ccctttgaaa aggttcttca acagcacccc    120
ctaggggtcc ttagaagttg aacctgcagg tacagcctta gtcctcatgg gtgtccaaga    180
aaagctgtct tcataagaac actgctgacc accactgatg tcctgtacaa gcctagtact    240
gatctggctg gtgggcacca gtgggaaatg ggcagtcaag ggacttgctg gctggtttta    300
actcttaaat tttgggcagg ggtcaggaca ggtgtatgtg gtggtatagt ctgactccag    360
agagacagct ttgatcccag cagagtacat cccagagtgg tggtggttaa gggagagaag    420
tcgggggggg ggggggggg ggaggcgggg cgatagcaga cctttctgaa gactccctga      480
ggtaaaacag gccctccgct tcaggccaag gaaaaattcc tcagacacct ccctggcctt    540
ccagccacta gagggcgctg cactttagtc cactgaggaa accggtgccc tagacccagc    600
caaatggctg gctatctttt agtacacaca tgcaactgca tatgtctggc acctcacccct   660 cttgtggagt tcttagaaga acaggagaac ctgcttaagg ctcagagtca tccctgacta    720
cacaaatgtc cacatgggcc tgtgtagaga aagcctaggg gcaaccactt ccagcagtgg    780
tgacctatgg tgtgtctggg gttctgtcca ttaaatcagg acaccctcac ctctgcaact    840
gcaggtgcag ccccagtcct cacgcacttc ccttggggtc tcaaggcagg tactgtgggt    900
cttaacatct ggaagacagg acacaggtgt ttagaaagta gttctattta ggggttcacc    960
tccagagcag tagttccccc ttgagaagca aaggggcata tccacatctt tcaggctgtc   1020
caaacagccc aaccaaagcc taacaaatac tggctgcttg ccccctcggcc caggatagca    1080 caggagcaaa tgttcaaaca tgaccctaaa ggcttctcag ttcctgagat gagatgggta    1140
cagggtcaac tttgtcagaa acaggacagc ctggaaacca cagggacttg agatccagcc   1200
tccagctggc aggcagagac aaatcccagg gcctttgtaa aacaaagact cattgatggg   1260
gtaggactca acatggactc agcaactcac tggtcatttc tgctccaagc agacgtctgt    1320
caaaccctct ccagcccttg gtccacctac tcagtgccat cctagtccat aaggcagtgt    1380
gcaagtgggc aggaggacca gacaatacat agcagcactg aagtttgtag aggccatgac   1440
tgtgaagtct catagatggg ggctcatggt gagccagttt ctccacaccc caactggggc   1500
```

-continued

```
ctgggggaga agcacccagg ccaaccataa gtgagtaaga caggctggcg aagtgatgca    1560
cacctgttgg cactctgcaa agtggagtca gaaggatccg ttcaaggtca ccctcagcac    1620
atactgactt ctacagccta tgtcatatga gccattgtct ccaaaagaca aaataaaat     1680
atagccatcc tccctggatg tgcatatgcc aaagaaattg agaccccagg aagatgtgca    1740
gtggacaccc aggctgtatg tgtgtagatc agagcctgag acgtcccttt accttcaggt    1800
caggaaaccc acaatgcaga tcctggcagc caaggagtcc aactttggct tgctgaatgc    1860
tgttagggca gcttccccat ctggtctatg ccttccctgg cctggcctgg ttctgactca    1920
attcaaaata ccccagaatc gtgaatagga atgactggt tagtgttggg agggcaggga     1980
agagtctaaa ggagacccctt gaagcaaatg atttggtccc tagggttatt gggttgttga    2040
tttattcgct tggttttcta aaggtcatga tgaggttgtg tacctgtgtg tgatggggga    2100
gctatagggc tgaactgaag ttacagatgt gtacgattga ttaaccgatt gatcaaccat    2160
tgattaactg attgacaggg tctcatcaag tagcactggt tactctgcag ttcactatga    2220
agatcaggct ggcctcaaac ttagagaccc ctcccaaagg ctggggttga aactagagag    2280
tagagagggc tcagcagttt aagagcattt atggctcttg caggtgatct gggtttggtt    2340
cccagaatca ttcatagctc caaatcgctc cagctccagg ggaatccaac accctcttct    2400
ggcttcgtta aggaccatgc ttgcatgtgg tgtacataca tacatacata catacataca    2460
tacatacata catatataca tacatacata atacatacat acagaccgac agacagaaag    2520
acaaataaaa tgagacaaat acatctaaaa gacaaaaacg tagctaaata agtaaggaca    2580
gctcctgagt aatgacaccc aaggttgacc tctggcttct gcacatgcac acatacacac    2640
acatacacat cagccctgag ccactcactt actgaatatc agaaaaaaac ctcatgtgtc    2700
agcatggaca tggggagacc aggtagccac agctagtttc tactcgttga aagcacctgg    2760
ctcagggctg gagagatggc tcagtggtta agagcactga ctgctcttct gaaggtcctg    2820
agttcaaatc ccagcaaaca cattgtggct cataaccacc aataatgagg tctgacgccc    2880
tcttctggtg catctgaagc tacagtgtac ttaaatttaa taataaatct taaagaaaa     2940
agaagacacc tggctctttt tagaatcctt tgtgagccca agggctgcct ggcagagcag    3000
tctcctggca tggcaggtcc tctgccagcc agtagccatg ctgcctcctc ccctgcactc    3060
aaccacaagt cctggagctc tggcgacctg cccagctgac atcttcccag ggtgaacata    3120
aaagatcccc cttcatctgg aacaggcatg tgccctgggg cggagcagcc tggcactgtc    3180
aactgtgatg ttcaaaagtg gaggccgagg gggtgccagg ggcagctcca gagtccccgg    3240
ggtcggggca gcccatctgt gtcagatgag ggcatgcagc tggcatggca catccaacat    3300
cactggacac ctactgtgag cagacagaag tcatagcccc attcttgaga cactcaacca    3360
atagctaaat atgaggtcag gccagaaaca gtgaaggctg tagggacctt gatgacccat    3420
aaagggctgg aagggtccaa gagaagttaa gagggaccca gaagatctaa aagggtctag    3480
aaagggtcca gaagcatcca ggggagtttg taaaaggtca gaaggattta agtgaactta    3540
gggtccaggg aaataaggga gaatctaagg atgcccagag gggacataag aaggtcccaa    3600
gagtctcctg aatgagaact ttcttcccac cagttcacag ctattcttcc cctgtatttc    3660
ctcccttctc cccaacatcc tgtcataaaa tcctctccac tctttggtga agaagggtgg    3720
gaatttagag tcagaactag tgtcacctgg ctccagcctc aggccacagc cttaggaccc    3780
ccaggagcca atgtctcccc ggacctgggg taaagtgtgg aatgtaactg atgcctgagt    3840
caaggtggca gagagtaggg gtcgggtata tgtacagagg cagaagttga accaggatcc    3900
```

```
cctggagacc gctaaggact acctaacctg ggatcctcac tttttaaggg agaagtcgcc    3960
agaagccaca ggagtcttgc tactgttttt gttgcctgac catgcctcag tttccccaca    4020
agtagggctt ggagatgggc tgagattaga acccagaatg atctcagccc ttctcacaaa    4080
tattcatagg tttctgcctt ggaggcggtg aaagcgacag agccagagat atggtagcct    4140
ccgggaacac acttttatta tggaatctgc caccttgaac cgagaaagga gttggcaccc    4200 gagggggtgag cgtcagcggt tgccccgccc gcggtgtcct cgagatcgcg gaggaacccc    4260
agagtggacc agggcttggt ctgcatcgtg cgtcaaggca ggggcccgcc ggctgggctc    4320
tgtgaccttg ggttcgtcct tggcctcagt tccccctgg ggaaccgagc ctgagcgcat    4380
ctccaaggtc tcaaggggct gactgacctt gagcctgctt gctggccaga gcctcagttt    4440
ccccatccat ccctgtgtgg ggtgagggtg gttcaggtgg aggcggggct cccgcccccg    4500
cccctccccc gcaagcagag gctccacccc cggctccgcc ctccctcggg ctcggccggc    4560
ggcggcggcg gccgc                                                      4575
```

<210> SEQ ID NO 27
<211> LENGTH: 5190
<212> TYPE: DNA
<213> ORGANISM: mouse

<400> SEQUENCE: 27

```
ctggtagggc attttttaaa ttagtgattg gtcgggaggg gcttctctca ctgtgccatt      60
catggactgc aggcctctgt aagaaagtag actgagctag ctgattggtg gtgatgcaca     120
cctttagccc cagctcttgg aaggcaaagg gaatcagatc tctgttccaa gccagcctgg     180
tctacagagt aagttccagg acagccagga ctacacagag aaaccctgtc tcaaaaagaa     240 aaaaccaaa atcaaaacaa agaaaagaaa gtagaaagga aggaaggaag aaaagaaaga     300 aaggaaatt gagcaagaga gagagagaag gaaattgagc aagccatgag gagcaagtca     360
gtaagctacc ctgaccctgt agcatcatcc ctaccttatc tcctggaata ttagttccca     420
tctctgttcc agtcactaga ctgtgactca ggatatgtaa gacaaataac cctttcctcc     480
caggttgctt tttggtcacg atgtttttatc acagcgtaat aacgctaaga tagtattcac     540
taggaaaaat gataaaaatc tgcacatgtt caaaatcagt tctttagttt ttaatatttt     600
gctctttact gggttgaatc caaagatata gaatgttaag tttggagaaa gaagaggtaa     660
cctttactgg ggtcggtgtt ggccagattg tggtggtgcc agggtcaaaa gtgctctgta     720
tttgtggaag ttgtggttaa ggaacccttt tagttcctga atttgtagaa ctaattgtgt     780
gtttggtttc ccacttcttc attatgatct tttttccttg tagccacatt gtccaaggac     840
tcctttgttc tttctcctta gtgcttgatg ggcggcatta tggcccctaa agacataatg     900
acaaacactc acgctaagtc catcctcaac tccatgaact ccctcaggaa gagcaacacc     960
ctctgtgatg tgaccttgag agtggagcag aaagacttcc ctgcgcatcg gattgtgctg    1020
gccgcctgca gtgattattt ctgtgccatg ttcactagtg aggtaaatgc aagtcactgc    1080
tacctaagtg aaattcgcat tgtaaccttg cagtcctctt atttcaaggg acaaaatagc    1140
atgtgttggt gattcagcta tggcatttgt cagccaattg gtcaccatgg ttaatcttgc    1200
tgtcactgtc acgtgtgtct tctgaagggg ctgctcaatc aatgggatt ttttttccaac    1260 acacagtcaa aagtcaaaag tattgggggg gggcgtgtct tccctgttag aacttccaaa    1320
caaatgctta gtaaataaaa tagaaatttg aaaccagata tagttgctca catttaacag    1380
```

```
tcctgacagt gggaagatca ccataaattt gaggccagtc tgggctacag aataacaccc    1440
acctgaaacc actcaacaag gaaggaaaaa aaaaaaaagt ctggtaaacc agtgaatctg    1500
tataatgtgg tagtcaaata ggtaagctct gaataagaca tgtgatggct ttctccttca    1560
gatcatcaat aattgctggg cggtggtggc gcacgccttt aatcccagca cttgggaggc    1620
agaggcagtc ggatttctga gttcgaggcc agcctcgtct acaaagtgag ttccaggaca    1680
gccagggcta cacagagaaa ccctgtctcg aaaacagaaa caaaaacaaa aagaattttt    1740
ggggactgga gaaatggctc agaggttaag agcactgact gctctttcaa aggtcctgag    1800
ttcaattccc agcaaccaca tgatggctca caaccatctg taatgggatc tgatgccctc    1860
ttctggtgtg tctgaagcaa cagggtactt atatacataa aataaataaa tatatcttta    1920
aaaaaatcat caataattat agaaaatgag tatgctactg atacagattt cagggtgact    1980
tccaatgagg ggagagggga tttaatgaat ggctgtgtgg tgttaactta gcctggtgag    2040
atagcacgtg gctgtaatgc cagcagtggg gaagtggagt tcaaggctgg cctcctggtg    2100
agaccctgtc tcacccaaac aagggtaggg gatgtagctc agttggtctg atgattacct    2160
aatatacaca aagccacgag attaagacca tccttgccta catacagagt tttaggctat    2220
ttggaactat atgagatgtt ttctccaaaa ccaaaattac tttgagagag agagacagac    2280
agacagacag caagctggtt caataagtaa agatactttc catccaacct catggaccag    2340
attccagtcc ctgagaccca cgtggggtgt gtatgtgtat gtttgtgtgt gtgtgtgtgt    2400
gtgtgtgtgt gtgtgtacac aaatgtactt gagtgtatgt atgtgtttgt ctgtctttt     2460 ttctttttttt tttttcttct caagacagag tttgtttatg tagtcttagc tgtcctgaaa    2520
cttgccctat agagcagacc agctttgaac ccacaggtcc acctgcctct gcctcccagg    2580
tgctaggatt aaagggatac accactatct tctggcttaa aagtttctaa aaagtaaata    2640
atataagaat atttaaacta gtctttataa gtgttttaag ttgaggtata tgaataatta    2700
tcacatgttt aaacttagac atatatctga attatttcat tatgcaggct ttttgtttat    2760
gtgtgcctcc atgaatttta tgggcatcat gtacaagtgg gtaccttgg  agtctaaagg    2820 gcatcagatg ccccagagct agagttccaa tggttgtgag ccacctgaca tgggtgctgc    2880
aagtgcttta acagtctctc caagcctctg gtatgggtgt gtgtacatct ggttttgctt    2940
gtttgtttgt tgttttggt ttttcaagac agggtttctc tgtgtagccc tggctgtcct    3000
ggaactcact ctgtagacca ggcctgccac tgcctcccaa gtgctggcat taaaggcatg    3060
caccaccact gcctggcatg tgcgtctgtt tttgaggaag aatcttaatg cctaaattgg    3120
ccctgaatac tccatctttc tgcctcagcc tcatcaagta tggagattat gggtgtgtgt    3180
catcctgcct tgttatgata agactctata aaaagtatct ctaaccacca gtattttctt    3240
tagttaatac ccatcaccat ggggctagag agatggctca atggtcaaga gcacactggc    3300
tgttcatcca gaggatccag gttcaattcc cagtacccac attatgggtc taactccagt    3360
tccaggagat ttgacaccct catacagaga tacctgcaga caaaacacca atgtacataa    3420
ggtaaaaatt tacaaaaaaa aaaaaaaag tacctgtcag tgtaatgaag tagttgttag    3480
acccagataa aaagggaaat aggataacag ctatatctat gggcccagtt aaactgccat    3540
gtttgtcatt tactctgggg gtaaatattg ccatttcatt tttcagatga agggtctcaa    3600
caaatgcctt tcaatgtcac atcacttgaa aatactacat agaggtaggc tttgcctcta    3660
cagcatgtgg ctgtaaaaaa tgattcttaa ctgccatttc agcctaaagg ctggtaggag    3720
aaatagaaag cagtcaggcc gttgcggcaa atcctgacta attaaaaac catcttgaat     3780
```

```
aatacaacag cacagatctc tagcttgtag tgttcttcag gatgtctgcc cccaaaacat    3840
tagcatttag ctgggtaggg agagttaacc agaagtgctg agcatgaaat ggcctaagcc    3900
tgccaactgc tactacagtc ctgctgaaac aggacgtgtc ctgcttgctg ttgtcttgag    3960
aacatctgcc tgcactgttt ttttaacatt gagagatttc tggaatcttg ggggagaaa    4020 aaaaaaaacc tcatttcttt tcatacatga ttcttctttc tttctctttc tccttctttt    4080
cttttctttt tcttttttcc ttccttccta ccttttttc ccctcttctt tttaaacagg    4140
gcttttctat gcctgtccta gaactctttc tgtagaccag gctagccttg acctcgaaga    4200
tccacctgcc tctgcctcca gaatactaga attaaaggtg tgtgccacca acgcctggct    4260
agggattgat tgttgttgt ttgttctttt gtttttgtt gttttgtttt gttttgtttt    4320
gttttgtttt cagaaacaag gattctgtgt ataacagagc cctggatgtc ctggacttga    4380
tttgtagacc aggctggcct cgagttctgt ctttgtccta gtctccccgt ctccctatgt    4440
gcaggaaata aagagggatt tttttttttt tttttttttt ttggtttttc gagacagggt    4500
ttctctgtgt agccccagct gtcctggaac tcactttgta gaccaggctg gcctccaact    4560
cagaaatcta cctgcctctg cctcccgagg ctgggatcaa aggcatgcgc caccacgccc    4620
ggcttggaat tgattttttt ttgtttgttt ttgttttggt tttggttttg gttttttgag    4680
acggtttctc tggaactcac tttgtagacc aggctggcct cgaactcaga aaccgcctg    4740 cctctgcctc ccaagtgctg ggattaaagg catgcgccac catgcccggc ttgggattga    4800 ttttttaag gaatgttttt tgttgttgtt gttactcttt gggctgatgg aggaattaag    4860
tatgacaaaa ccatttagtt aacagtggaa gtacatgaaa gtgtggtaac aggagtgtgt    4920
gtgtgagcac acgtgggcat gagtgtgcta acccatgtaa aggtgtggtg agcccagagc    4980
ttgacatcat gtcttcctta actgcttctc cacctctcca ctttacagtg tgattcaagg    5040
tctctcactg aaccccgagt ttgctcgaga gtcatgggat ctgcatgtct ctgccctagg    5100
gctctgaggt tttgctatta cgatcttgtt tttgatatac aatgtcactg catagcttag    5160
agcagctctc gatcactgct tgcctcttgc                                      5190
```

<210> SEQ ID NO 28
<211> LENGTH: 28812
<212> TYPE: DNA
<213> ORGANISM: mouse

<400> SEQUENCE: 28

```
ccctccccc aagctcatgc agcataaaca gaggagccgt ttacaatgat cttcatgttc      60
tttttctatc cagatgtagt ctgagggcgg atgagaggaa tgtggtgatg ttggaggagg    120
ttgtagctat aaatctcaga gttcattctc ctgaaatttc attgactatt tctattttag    180
ccatacatgg tggcaaatgc ctgggatgag agggttggct ataagttcaa agacacctta    240
ggctacaacc tgaaaaccag gccagccaca tagcatatag agtggtatgt aggagaggaa    300
agaagagaag agagagaatg ttttatcata aaggcacatg gacactagtg ttaatgaaac    360
ttttgtattc tgttctttaa ggcatctatg ttggttttaa tatagaatca ggttaactct    420
agaaattttg atattccatt gttcacgcct agggatacag tcatctgccc attttatttg    480
aagatttaca atacatgtca tatttttccag atacaaatca aataaaatag attataattt    540
aaatttttta ataaaattat tttatgctta tgagtgtttt gcctgcatgt atgtgtcaaa    600
tgtgtgagcc tggtgtctgt ggaggtcaga aaatggcttg acttcctgga aatggtggta    660
```

```
tgattgttta ctgcaatggg tgatgggaat tgcacacagg tcctctgaaa gagcaactag    720
gacccttttt gtttggtttc tctgtgtagc cctggcaatc ctggaactca ctctgtagac    780
caggctggcc tggaactcaa gagatctact gcctctgcct cccgagggat gggattaaag    840
ctgtgcacca ccactgcgca gtgagcagcc agtactctta accactgagc catctctctt    900
gtctcagatt gttgttttta aagatgtgt atttagttag taccagcatc cgtttaagct     960
cttagacttg ggttctgtgt ctaccttgtg gaattgaaag taccgtcctt ttcctacctc   1020
ctgaattttc agctttcaga aaggggaag ccgtatgttg acattcaagg tttaactgct    1080
gctaccatgg agatcctgct ggacttcgtg tacacagaaa cagtacatgt gacagtggag   1140
aatgttcaag aactgctccc tgcagcctgt cttcttcagc tgaaaggtac agacagtaaa   1200
aggtgtcctt gttcatgaca ctttagccct ggaagtgttt tcatttgaag caaaattaat   1260
caagagactg agagatcagt ctagaagcat gacatttgaa tctttgagca tggaagataa   1320
gatagagtca agagcaatgc aaaagaatct caccacataa gagtatttgg gtcttgtaaa   1380
agaaaacatt taaactttt ccgttttgc aataatccca acacttaaga agctgagaca    1440
ggaggattgc gttaagtttc aagccaattt agtacataaa atgagactac atgttaaaat   1500
gaagcaaagg ggctgaagag caggctcagt agttgagacc atggactgtt ctccagaagc   1560
atctgtattt gactcccagc acccactggt ggctcacaac tttgtaactc cactgcaagg   1620
gacctaatgc cctcttctgg gaacatggca cacagatgca cgtttccaaa gcacccatag   1680
cataaactaa ttaaactgaa ccaaacaaag cagaatagaa aatataggta tttccttaat   1740
acatacatgt atacatacat agtaaaaatt gccaagaaac tgataatatt cgttgtctac   1800
atagattctg tttatttacc ttgtcatttg atgtttgtgc atgtagaggc taagaggact   1860
tttaaaata aaccttttg tttgaatcat gtaaaatacc tttttaagaa aatttatttc     1920
tgtttacttt tattatttat tatttttatg tgtatattat tctcaaatgt atgacctcta   1980
atggccacag agatcagaag agggtgttgg attccccca aactggagtt acaggcagtt    2040
gtgggctgca ttctgggagt tgggaactga acctaactct tattcaagag taatagtgct   2100
tttaactgtt gagccatctc tccagtcccc taggggttgt ttatttgttt gttttgtttt   2160
gttttgtttt tgagacaggg tttctctgtg tagccctgac tgacctggaa ctcactttgt   2220
agatcaggct gtcctcgaac tcagaaatct gcctacctct gcctcccaag tgctgggatt   2280
aaaggcttgg gccaccatgc ctggctcccc tagtttgttt ctgtatttgg tttttgaaac   2340
atggtctcac tatgtaactg tggctatctg ggaactgctg gtcaggttgt cttctaactc   2400
aaggatatcc atctgcttct gcctctgaaa tgttagaatt agaggtatac atcctcatgg   2460
ctgccttaaa atatcttttg aaataaaat ttatactagg cagtggtggt gcatgcttta    2520
attccagcac ttaggagaca gagtcaggta gatctctgtg aattggagac ctgcctgctc   2580
ttcagaactg gttctaggac aaccaggact tcacaaaaaa accctgtctc caaaacaaaa   2640
caaccaagac aaataaaaaa taataaaatt aaaattaact tatacttgag aaggagaaat   2700
ggcatggact taaaaaaaag taaataaaat aaattttaaa ttgatgtata gcagttaaaa   2760
tataattttc actgcattag agatggtctc tcttccagtt tcttatgtat gtgtttgtgt   2820
gtatgtgtgt gttcatattt gtgtactttt tctttgtttt ggcctacact gtaaagataa   2880
gactatccct gaattgtatc ccagttggtc ctaactctgt cttaatgcct ccacctcctg   2940
agtactagga ttcagttgt ctaccattat aagtagccag tctgtctctt caacctccaa    3000
ttttgtatat ctacataatt aaaacatttt tactgttgtt tgttttgttt tagataagag   3060
```

-continued

```
tatcactgtg tagtctaacc tggccttgag tgtataatcc tttgtagcct cctgaatgct   3120
gggattacag gcacagacac tcactctcta cctgtcatac aagactgaag tgaagtggag   3180
cacactaagt tcagacttag aaaattaagt caagtttatg ccgggtattg tggcacacac   3240
ctttaatgcc agcactccag agagagatgc agacagatat ttgtgagttg agaccatctg   3300
gtccacacca cgagctctag gccagctagg gctacacagt aagactctgc ctcaaaaacc   3360
aaaccaaacc aaacaagaac tgggttcata cactggacct tttgtttttt ccagtgacag   3420
ggattgaacc cagggccttg tgcataccaa gatgctagat gagcaatgcg cttttctgtt   3480
aagcttcaat ccaagctttt attctgaata tcccagagaa ttatgggatt gttttccttt   3540
acttgagttt taaaagtttg atatagggac tagagagatg gtaccatggt acttgtcttg   3600
cagagaacct gggtcaagat cccaaaactc atgatgtctc acagctgcct ttaactagtt   3660
ccaaggcaca agcatgacct cactggacac tgcatgccag gacatggaca tgccaggaca   3720
cgcatgccag gacacgcatg ccagggtgca cttacacaca gacctactac ttacacacaa   3780
aataaaaata agtaaatctt aaaaatctat ctagagtgaa aaataaaaac atagtaaatg   3840
agccaggcag tggtggcaca tgcctttaat ttcagcactt aggaggcaaa ggcaggcaga   3900
tttctgagtt caaggccaac ctggtctaca gagtgagttc caggacagcc aaggctatac   3960
agagaaaccc tgtcttgaaa aaccaaaaaa tacagagaca aaatttggag ctgtgacgaa   4020
aggatggacc atctagtgat tgccatatgc agggatccat cccataatca gcttccaaac   4080
gctgacacca ttgcacacac tagcaagatt ttgctgaaag gacccagata tagctgtctc   4140
ttgtgagact acgccggggc ctagcaaaca cagaagtgga tgatcacagt cagctattgg   4200
atggatcaca cggcccccaa tggaggagct agagaaatta cccaaggagc taaagggatc   4260
tgcaacccta taggtagaac aacaatatga actaaccagt actccggagc tcttgtctct   4320
agctgcatat gtatcaaaag atggcctagt cggccatcac tggaaagaga ggcccattgg   4380
acacacaaac tttatatgcc ccagtacagg ggaaccccag ggccaaaaag ggtgagtggg   4440
tgggtagggg attgggggggg tgggtatggg gcattgaaaa tgtaaacgag gaaaatacct   4500
aataaaaaat aaattgaaaa aaaagaaaaa cccaaaaaaa acaaaaaaca aaaccatagt   4560
aaattaagtt actatttta gattggttcc agtagcagaa gagtttgcag cagtctgata   4620 gttttgaaa ctaggtccga ctagctaccc tcattttaaa gatgaggcag aagcaagtga   4680
aaatgctcac agccagtgtt tgaatgcctg aaccataaat gttctaatgc aatgttaagg   4740
tgtagagcca gggttcctct gataacatgt agagaagatg ttaagatcca agaatggaag   4800
gcacttttca cttggccaag tatcttaggt ctgctcactg cctgtgtgtg tcctaggtgt   4860
gaaacaagcc tgctgtgagt tcttagaaag tcagctggat ccatctaatt gcctgggtat   4920
cagggatttt gctgaaactc acaattgcgt tgacctgatg caagcagctg aggtgtttag   4980
ccagaagcat tttcctgaag tggtgcagca cgaggagttc attcttctga gtcaagggga   5040
ggtggagaag ctaatcaagt gcgacgagat tcaggtacag ggttgccttg tgttacagt    5100 ttctgtacat tacagagcag gatggggtga ctgtgtccat attatggctt cataatcaaa   5160
tacatgtatt gatgccaaaa gttttaattt atttgcatgt ctatggagaa gaaatctgc    5220 cctggtcatt catcaaatat atgaattcca gcggtaaata attaaataag cagaaattgg   5280
aaacaaggta aattttctat gcaatattgt tacgcattgg ctgtgtagta gtgtttgttg   5340
tgtgtaggtt tatagttagg ctgaacttgg gaatgaggaa tccaacagag gtctaataga   5400
```

```
tatctttgaa gcctgtactt taatctccag tgtactagtt ctttgtttgt ttgtttgttt    5460
gtttgtttgt tttttcaaga cagggtttct ctgtatagcc ctagctgtcc tggaactcac    5520
tctgtagacc agactgtcct caaactcaga aatccgcctg cctctgtctc ccaagtgctg    5580
ggattaaagg cttgtgccac catgcccggc tcgtactagt tctttagaca gtagcttcta    5640
gaaagatatt cggagagcca agtcctatgt atatattcct tttgagtttt atttctccac    5700
tgaaatagat tactgagtgt ctgtcctcag tttatataag aggtggatta gaaagtatta    5760
gaatgggttt aatgctttga cattccatag gaaagtttgc tacctaaaga aattctgtgg    5820
ccttccaggc ctgccagtgt gtgtctgtaa tcccagtact caagaggctg acataagatc    5880
acaagcttgc ctaggcagca gtgagaccat gtgttctttc ctcccccac ctcaaaaaaa     5940
ccaaaagcac catagaagaa attctgtgat acactttgtg aaaaccatat ggtctctgtt    6000
ttgattggct acaaaacagg tgtgtatgtt acaaagtaaa agttttactt ttttttctctt   6060
tttctttttct ttcttcttct tttttttttt tttttttac attttttcttt aacaaatgta   6120
aggcaaaact gatgagagca gttggtaaat tgtttgcacc tagagaaaaa ttattcccca    6180
agttgacttt tatatcagcc tagagaggca ctgttagaga tgctaatgtg tcaatatgtg    6240
ctggtctcgc tctcatcccc accgtgcagg accttgtctt ctcttgcaga cttgtgagca    6300
tggccacaaa gtgtattctt cacatttagg acgacccatt ggttagctag aaaaatagag    6360
ctcctttttt atatttatta ttattattta ttaatctatt tagtttctga tttttttttta   6420
gacagggatt ttctgtgtag atcagggtag atttgaattt cgaaatccac ctgcctcagt    6480
ctgccacgtg ctaggataaa atgtgtgcca ccacacctgt catggctctt cttgatttgt    6540
ctatgtatga gaaaacacag tgatgatact aagtactact gttataggaa aatagtactt    6600
cgcatttact atgggttatt ttgtcaaagg cttactgagc actcataggg agagatccct    6660
acccccttggt gcgtctactc tccttctccc tctccccacc tcctcttttg attcttttgt    6720
gtttccaagt tagagtttga aattgttgt ttttttaaat gttgttgttg ttttaagaca     6780
gggtttctct gtgtagccct ggctgtcctg gaattcactc tgtagaccag gctggcctcg    6840
acctcagaaa tccacctgcc tctgcctcct gagtactggg attaaaggcg tgcaccaaca    6900
cactggctga gtttggaatt gttaagtctt gggcatggta ggcaagtact gtgtcactga    6960
accacccctgg actcagctct acagtatctg ttctgtggca ttgacctcat ttgatcctca    7020
catcctgcag ttatcagaaa ctgtggctca gaggtaaacc ctcacaccat tgtaggtagt    7080
aagtaataga gccaggattc cgatccaggc aagcagctag atgcgatacc acacatctgg    7140
attccagcat acaggagcca gagctatgaa gttcaaagcc atcctataga agaaaccttg    7200
actcaaaaaa ccaacaaaaa aaggtaaagg aaaaatttaa aagctgagta tactagctta    7260
tacctgtatt tccatcacat aggcagtata ttcagtttaa aaccttcctc tgctacatat    7320
tgagtaccag actagcttgg gctgtatgaa actctttctc caaacaacaa caacaaaaag    7380
aagaagaaga aatactcaga aacaaatcag gccatgaatt cccaaggctg tcctggaact    7440
cactttgtag accaggctgg cctcagaaat ccacctgcct ctgcctccca agagctggga    7500
ttaaaggcgt gtgccgcctt gcccagcttc tctgaaattt taacttgctt gttttttagac   7560
aaaagaaaac agtattattt tttttttag atttttcaag actgggtttc tctgtgtagc    7620
cctgaccatc ctggaactct gtagaccagg ttggccttga actacacaga tgcctttgcc    7680
tccccagtgc caccatcgcc aggcaagaaa aattatcttt ataataaaca tcctgcatcc    7740
tccccatccc ctgtctgtaa gatggatcac cttgacctcc cacatatttc tcctagactg    7800
```

```
tcacaattgg agtctagcct gttgtgcaaa gaagactaga actgatcttg cagctcttgg   7860
cccttctaag tgttctaccc acagtcacca cagcagtgtt tgcaaacatc tctttattgc   7920
tgtcttactg gaagcattca agtgatatcg agttgctctc actgtgatgc cttcagcagc   7980
ctggtgctta cctaaaatct gtcaccaccc acccttcttc ctcccaggct ggacagctaa   8040
aatgtccccg tgtgccagtc ctctctgctc taggtcagtt ctgacctcta gaaagttctt   8100
tcaagatgga ctaaatttcc ttgtctggtc tgatagccac taggcacatt gctgttgggt   8160
gtggaacgta gctagtgctg ctaagaagct gagctctgat tttggtaaat gccgcttcgg   8220
tgacaggtag tgcagctcta gagcctcggt gcactcttgc ttgtcttttt cctttttttc   8280
tgatttagag tgctgttggg gattttgaga taagatctta ttttgtcctg gctggccctg   8340
aactcactat gtaggcggtc ctcctgcttc gagcctccaa gtgctggaat ttcagcata   8400 tgctgccact tctgacccct tgagtactct ctctttattc tttctggtta tttgctagtc   8460
gtccatcaga ttccagcttg ctacttgagg gagacttttc ctgactcact agaaatgaag   8520
aaatttccta ttgtttctgt ctcatggctc tgctacttcc ctgtataatt ttaatcacaa   8580
taagattgta gtaattgata attggtagta cttacttaca atcctggcaa ttggaatgat   8640
aagacaggtg gatcagatga aggcagagtc tggtctacag ggactggact tgatttctca   8700
tcatcagtgg aagttcagtg cattgatgaa atgaaacata tgcccaaaca tttctgcttt   8760
ccaaagcacc acagttcttg gggaaggtgt acaaggtcac agtcaaccgt ttagatgagg   8820
ccttgggtta catctgccta gagattgctg agagagcctg gtcctgcac ctacgtgtct   8880 gcctttggga agtcctaggt cttattgtgc ctgtcacttt tctggtggca taatacatac   8940
tttagagagt gcttcttact ttatctatct atcgtgtata atctaagttc tccaaagatc   9000
tgaatctgtg tgtcagaaca gcacagaatc taacacatag tagttgctga aatgctgact   9060
gaacatactt tgaaagctga aatgttattt atgatgataa agtgaagttc ttgcttcaga   9120
ggcaactaca aatgaaaatt atttcaattt taattaggat aacagatttc ctctcccatg   9180
tttactaaag ttgcagaaat gaccagacaa aaattcaaga atggatgcag ttctgaaaag   9240
aaggccaaca tgtgactcat catttattaa acactgtctc tgttcttttt taaatttaat   9300
tttatttata attcactttt tatactccat attccattcc ctgctcctcc ccatctaccc   9360
tcaaccgttc cacatcccat gcctcttccc accccacccc accccatctt agttcttttt   9420
aaattgcata taattctctt cctgtatctg aaaagactgt tttcccagaa ctttcttcat   9480
atttctggga gatgggaaat aacagtaatg gaggacaggt agcacaaagg agactaagca   9540
aggctgcctc gagtttgtgg ggaagtaaaa gtctgtgacg tgtgaatcta cattaatagg   9600
tggattctga agagccagtc tttgaggctg ttatcaactg ggtgaagcat gccaagaagg   9660
agcgagaaga gtctttacct gacctcttac agtatgttcg gatgcccctg ctgacccca   9720 ggtacattac agatgtaatt gatgctgagg taagtcacat aaggcgcttg gcatccagaa   9780
actccactaa ctctgcagcc tagctactca aaaccagcag ctttaatgca ggcagagtca   9840
cctggttccc ttccgcagga atggtggaat gataaagctg ggaacgttat aggcataaga   9900
aatgtttatt gcttggcaag tcacatctct gtcacaaatg aaaatccata atttttattta  9960 atttgtact gtgttgttgt cttttgttt tatgtgcctc ttatgtttta taaaaaactg   10020
tgtactgaaa agcataaaaa acaaaacaaa caaaaaaacc ctgtgtattg accgagcagt   10080
ggtggcgtac acctttaatc ccagcacttg ggaggcagag gcaggcagat ttctgagttc   10140
```

```
aaggccagcc tgtctacaga gtgagtgcca ggacagccag gactacacag agaaaccctg   10200
tcttgaaaaa aaaccaaaac caaaacaaac aaacaaaaaa ctgtgtacta gtctctctta   10260
aacatgaatt gttataaatt gctctggaaa aaaagagaca aaagttgctt tatttgtcag   10320
accctcatgg ttttacttct agtaagcctg atttacttag tttgatgcag ttgagctttc   10380
tattgtttta taaaagtgtt tctctaactt aagctgcaac aatgttttgt aactcataca   10440
cacacaacac acacacacac acacacacac acacacacac acacacacaa tgttgcgtgg   10500
actgttgtcc tagtttgctt tctgtttgct gtggtaaaca ccatgaccac aaagcagcat   10560
ggggagggca gggtttattt cttgcatgtt atagtctgtc atcaagggaa gcaagggcaa   10620
gggttcagag caggagcctg gaggcaggag ctgaagcaga gaccatgtga aggaacactg   10680
cttactggct tgcttccatt ggcttgctta gcatactttc tgatacagct agggactacc   10740
acctgttcag gaatggctcc cacatcggtc tctaatcaga aatgcctgcc cccccccaa   10800 tccaatccca aggaggcggg tgtactttga caagcactca tctataacat ttaggtgaag   10860
cccagtaact tcttggccag gacctgacca ttttaaaagt taaccataaa aatagttct   10920 tattcacttt acaaaatttg tttggtctgt tgtagtaagg gcctgtaatc tcttggtaga   10980
ggtaggcagg catatcaaga gttcaaggtc agcctaggtt acaggagact ctgtctcaaa   11040
caagtaaaca aatattgaga caccctccc aaaattaaaa aaaaaaaatc aggctaatta   11100
atgtcacatc tcaaactcat tttccccttc ttccttaaga cctctattta ttagttttct   11160
tgttgctgtg ataaaatacc ccacaaaagc aacttaagga aaaaagggt ttatcttggc   11220 tcacagttaa aagttatagt tcatcctgaa gaaggcgtgg cagaaaaacc cccatgaagc   11280
tgtgggtcac actgtaccac agtcatgacg cagagaggga aagctggcgc acagctgaat   11340
ttctcctttt tgttgggctt gggtcctaac cagtgctatc gtgtggccta cgttaagggt   11400
aggtcttacc acttgagcta aacctttcag aacccccccc cccccaggg acacagcagt   11460 tggtgtgttt cccaatcact caagttgata gtgaggccca accttcactc ccttctgaat   11520
cagtctttac attatgtttt agtacagaga tccggagcta gaatcaggaa gctgaaatcc   11580
taaatcagac attcttgtga gacccttagg gagatgacct cagatttttt cctttgtgaa   11640
gctgcagtga cattactcac ctcatacatg gttgccaata ttcacatgca gaagctttag   11700
agatatctat ataacagtag ttgctactgt tatatatttt cttttccaat gcatactgaa   11760
aacttcttgg agtcaaacta ataaactaga gctttatatg agttgacgat tccaacagga   11820
aacagatggt acagttctaa ggaaggtttt ctctcttct ctctctctct ctctctttct   11880
ctctctctct ccctctccct cccttcctct ctctctctct ctctcccccc cctctctcca   11940
cacacacagt ttacaaagtt acatttggag aaacagtaaa agacagtgga gactacagat   12000
ctagaacaac caagctgtca ccagcgctca gtctagctgg gctaagaagt gggtatcaga   12060
gcctgaagag aaaggcttga gaggagcctg ccctgcagca gaattcatcc cagctaggag   12120
tcatatagag accttactgg tgcggtttat agggaccgtt ttttctgaac tagagagcaa   12180
agtacagagt ggaggtagat gctaatacaa agatctattt cctgtgtagg tgtatgtgta   12240
tatgtgcaca tgtatgccag aggtcaatct tcggtgctgt tcctcagacc atccagcttg   12300
gttttttaaa tacagactga ttgattggcc cagagtttct gattgagctg gggcattaca   12360
agtataggct accatgtcta gcttttatg tggtttcgtg tgacaggact tgggtcatca   12420
tgcttacatg gcaaggtctt taccaaagtg agccatctag agcaccagtg ggaatagatg   12480
tgggagttgg actaatggtg aatacatgcc tataactcgg cacttggaag atagtgcaga   12540
```

```
aacatcagac attgaaagtt atcctatgcc ctgttgtaag tttgagacca acctgggcta    12600
caggagaacc tgtcagaaag aaaggatgaa aaggaggaag aggagaacaa aggagggaag    12660
gagagagaga gctttggggg aattatttca aagaagacat ttttccaaga gagattgtgt    12720
gccttgtctt tttgagacag tgtctctctt tagatcatcc tggctagaag tcagtctgta    12780
gctctgagtt ggcttgaagt ctcagaaatc cttttatctc agcctgccaa gtaactagag    12840
ttgcagatgt gaagccagtg tgctcagctc ccttaagatt cgtactaatc cttacctgct    12900
tttatctaca tacataaatt gcttctttat atacctcatt ttgttattgc agtattagaa    12960
atggccggtt cccttctctc ttctgtcttt tagcctttca tccgctgtag tttacaatgc    13020
agagatctag ttgatgaagc aaagaagttt cacctgaggc ctgaacttcg gagtcagatg    13080
caaggaccca gaacaagggc ccggctaggt aagctggtat tcctggaaaa atgaggggat    13140
gtctttgaac tccttttttca gatggtatga tatagttgga agtaacatct gtaatgctta    13200
cagtagactt gttttagacc tgcttttaat ctctttagac aagtagctgc cattttaagc    13260
ttttatttcc tgttgtttaa gagtgtcttt gtggcacata attattggag attaagttag    13320
ataaagtaga gagaaaaaga ttttacaaat tatcatatat tatataacat taatttttttt   13380 taaagaatgg gtaattttct ttttatttat ttattaatat gtaagtacac tttagctgtc    13440
ttcagacact ccagaaaagg gcgtcagatc tcgttataga tggttgtgaa ccaccatatg    13500
gttgctggga tttgaactca tgacctttgg aagagcagtc agtgctctta cctgctgagc    13560
catctcacca gcccaacatt aaatttctat ttcagcattt aaataaaggg cttggagcta    13620
gggatatagc tcagttgtta gagtgctttc ctagccctga gttcaatccc cagcacagca    13680
taaatggggt gtgatggtaa atgcctgtaa tcgggaagta gaggcaggaa gattataaat    13740
tcatccttgg gcacataaaa agttagaagc cgggatggaa aaatggctca gcagttaaga    13800
gcgttgactg ttcttccaga ggtcctgagt tcaattccca gcaaccacac agaagctcac    13860
aaccatctgt aatgggatcc agtgccctct tctggtgtgt ctgaagacag caacagtgta    13920
cccacataaa tgaaatgaat aaatctgcca gcagtggtgg aacatgcctt taatcccagc    13980
acttgggagg cagaggcagg tggatttctg agttcaaagc cagcctcgtc tacagagtga    14040
gttccaggac agccagggtt acacagagaa accctgtctt gaaaaacaaa acaaaacaaa    14100
aaataataat aaaataaata aataaaata aatacataaa tctaaaaaaa aaaaaagttc    14160
gaagccagtg tgatagactg tctcaaacaa acaaagtaaa actacagggc ttttttgacag   14220 tcatgtatca taggtaaaat ttctggctta acacttacct tagacaggaa gtttattatg    14280
tctgcctcag atgtttttatc tgtgaatcaa cataacatcc agctctaaga aagtcataac    14340
aattaaatga agaaatctag gaaagggcta ggaacagtta ctgtcacgta agtgctactt    14400
acgttagcaa atagacagag gttcaaatca aagccctgcc agtggctaat tagtgataac    14460
aatttatccg atcttaactg gatatggtgg cacagagcac taatcccagc actcaggagg    14520
tctagtcagg ttgatctttg tgagttcaag gacagcctgg tccagatagt gagttccaga    14580
gcatccaggg ctaaatagta gaccctgtct ccaataaata aataaataaa ttaataaatt    14640
aattaattaa tttaaaaaaa ccatttttt aaaacacaca cttatttgat cctatgcttt      14700
acccctaaac tgaggcttag tttcttctga atgggttgtt gggaggattg aattggaatg    14760
tggataagac acttagctgg cacagagtaa atatttagct attttttatct tggtccctat    14820 tactgctctg taaaaagagc cttcctgcca ctctgtaaaa ctattttgaa gattatcact    14880
```

```
tattctgtat atatgaggtg gcacttcatt tgctttattt ttttaataa tttatttttt    14940 attttatatg tttgagtgtt tgctgcttgc atgtctgtgt accacatgtg tgcagtgccc    15000
acagaggtca gaagatgaca tcagatcccc tggaactaac tagagtttca gattgttagg    15060
agccaccatg tggtttctag aacagattc ttagccacag aaccatctca tcagcccta    15120 gtgttttacc atttccttt cttagttttg attttagaat tggtgtatat tagaatattg    15180
acaatcaagt tgtctattga tagaggagta agcaatattt ttccagtttt tttcttgttt    15240
ttaagatctc tctctttttt ttttggttt tttgagacag ggtttctctg tgtaaccctg    15300
gctgtcctgg aactcacttt gtagaccagt ctggcctcga actcagaaat ccgactgcct    15360
ctgcctcccg agtgctggga ttaaaggcat gcgccactac gcccgtctta agatctcttt    15420
tattctgtgt gtttgtgttt atgagtttt ctgaggggac cagatctcct ggagtagagt    15480
tacaggctgt tatgagccac ctgggtgcta ggaaccaaac ctcttctgca aaaatagcgt    15540 gagctttaa ccgctgaacc atctctgtgg cccccattgc tgttgttttc aattaaattc    15600
ttcccatttt aaatattttt attttgttt acaatatatg agtgttttgc ctgcatgcag    15660
gacgtatgtg caccatggag gccagaagag gatgccagat tccctagaa ctgggattgc    15720 agacaattgt cagccaccac atgtgtctgg gaatcaaact tcttcctct ggaagagcag    15780 ccagtgctct gaaccactga gccatcccag tcctgcccac ctcctatgct ttttagtgtc    15840
acccatagtg tatgtttaat attaaaatat atagaagcaa aaattaaaa atcacccaa    15900 attctaccac acagaaatat acttagagaa agaggagagg tagaaaaaaa aattggagct    15960
tgagagatgg ttcaggggtt gagagcactg actgctctct caccccatc agtagattcg    16020 ctccaatctg taactcgcat tgaggggatt ctgagatcct tttctggcct ccaaagacac    16080
ctgcacactt gtacatttaa actcatgcag gaacacatac ataaattaaa cacacacaca    16140
caaaaactat taggaaaggt attaatttct gcagtgtgac aaaatgtgat ctgaatatca    16200
tgtactatat acaaaaatag atcaacacat atagattaag gaataaatga agtgtgaaaa    16260
cagaaattac aggaaaatat ttgaataatt tccagatcag attcatttt tgtttggttt    16320 ggtttaggga atttgtttca ttttgttatt tttaactagg ctattacact gtagtccagg    16380
ctagcctcaa attcattgtg taaaccaggc tgaccttgaa cccaaatgac ctggccttgg    16440
tcttctaaat tccaggatta tagtcatgag tcatcacgcc catttctctt ttttaattat    16500
aatatatggt aaccattttc ttatcataca aaaagtatta aacatgttta tattgctgag    16560
ccacggtgaa atcatataaa ccatgtacta cctttatcct gagtgacttg gtggaatggg    16620
gtaggaggat aatcgccggt atatccagta tataagactg actgtgttga ccaaaagttg    16680
ttgatatttc caaaaacatg gtatacaact caagttcctc ctgtacagga gggaatggct    16740
aagtaggtta cagcccagtt ataccatggg tggcctggca ccaagagaga catcgagtcg    16800
tgtgtgcaca gctggggctt ttctcaccta tcctttcctt actatgtatt gactgcagtg    16860
gtgggaggac attgcataga ccatggtgtg tctgtccatg gtgtaaatgc ctttatgccc    16920
ttaccggctg agtcagctca ttagccccag cttttccttt tctctgtctg tctctctgct    16980
tctctctctg tctcttttaa atagaatctt gcactgtagc ccagtctgac ctaaagttct    17040
taattctctt gcctcatcct cttaagtagc tggactatag gcaccaagct gcgctggctg    17100
ggcgtctaag ggaaaaaaaa ccatttttga aaatgggtga gtgctaggct cagtgatgga    17160
aggccagcct ccagtgggac cctcctgttt ggtcctcagc ccttaaaagg caggcgctct    17220
tgaatactta ttggtagaag cagagaccca ccacactcag cctttaacag catcacccta    17280
```

```
caggtgggat ggcaagggca ggttagcagt ttgtttattt acatacttca gcattagtcc    17340
taaaaacgtg cagttacctt tgttgtcttg aaaataacaa gtccagagtc tgtagctcaa    17400
agatagtaag tttctagaag agcgtataaa gcagtgactg agcagggatg cactaggtg     17460 gcgtgtgtgt cagtagacct ctgtccctaa ttttatatat ttatatcatg gattattttc    17520
atttttatct tttgtaggga tcagcctgag gcatgctagc caagtgctgt tgcactgagc    17580
tgtgtcccct tacttctcttc ctaattctgt acattctaga aacctgctgt gtaggcttgt    17640
tatcttcctc tgagccacag cgtgtatcca tgtaaagtgg gttaagttca cccactaggg    17700
tactttcaaa gacagaagat atgggttttg ttgttttttt gttgttgttt tttacataaa    17760
agcattcatt agttgcttat taaactgaac taaagccaat gaaaattttt atgagccaga    17820
aaatgcagaa ggttctctag aggttcattg tctacatttt gttaaatatt ttgcaaatca    17880
gaaaactatt ttctgacctt aaggaattag atttagtttt atgtaattca taactttgaa    17940
aaaacactga cattcttttt gactagatca attttgattt ttttaagggc ctgcaccagc    18000
ttacacatta atcttgtcag gtgtcctggt atacacctgt aattacagat actcaagagg    18060
ccagtgcagg aaggatctta agtttgtgat catactgggc tacaagtcaa tccagccact    18120
ctgtgtctcg agatgaaagc tcagaagtaa ctggggagta gttcagtgag agcacttgcc    18180
tagtatagga gagcctgggt ccagtcctga gtcaccaaaa gtaagagagg agtcatctga    18240
cactgctgtg ggggtgcata ttaggtccac tcagggcaa aggcagctgg atctctctgg     18300
gttctagatc ggcctggtca atataatgaa ttacaggcca gctacaacta cataaagaga    18360
cctgattttt tttttttttt tttttttttt tttttttgg ttttcgggt ctctctgtgt       18420 agccgtggct gtcctggaac tcactctcga actcagaaat ccacctgcct ctgcctccca    18480
agtgctggga ttaaaggcgt gggccaccat gcctggcgag agacgtgttc ttaaaaacaa    18540
acaaaacagc aacaaaaacc acctggcata gtatacactt gtatttctaa tacttgaaat    18600
gttgaagcag gaaaaaaaaa ataacaagtt tggggccgtt ctgagctata tccctagacc    18660
ttctggagtt ggtactgatg cttactggaa tttactaaca ctcactactt ggttagcagt    18720 cttaccttttg ggttgtgagc cttgccttta acagctaagc tatttctaaa gcccggggag    18780
ccgtctctca aaacaggatc tgtccttgga aaactatgaa gtcctttata acgaaggttg    18840
aggatccagt aagctagagt tctagccatg taaacccatg aaatccttaa gtaggtaggc    18900
atggggatga attacatctg gctaaaacat gttaagtgtt ccacaataaa gtccttgaga    18960
ggcagaagca gaaggatggg gagtttgagg ctagcctggt ctacatggca aaactgtctc    19020
aacaaaaaat aaatgtgatt cattgacctc tctgcccaaa ttctactgtg aactttagta    19080
tttatggaac aattttgtgt tgacaggcag ttgtcatttt tctggggttt ataacaaaat    19140
ctgtttcctg cctactgctg tttacaagct gctgaacaaa gtcatagcaa taaataaata    19200
gataaataaa agtgtggcag ttttttgttc tttggttttc tttagttttg agacaggcca    19260
ggctagcctc gatgtggttt gtttgttgat attttaaat atgggaattg cataatgtaa     19320
caaataatag ctaaaaaaaa aatcaatgga aaatttactg tcttttttctg atcatatccc    19380 tatagtgtca tttatcatgt tctagccaga tgtgatctgg tacatgctaa agtgggagaa    19440
cacttgagtt caggaactag aaatacagag gaacctgttc ttaaagagtt gaagggatg     19500 ggggtgaagg ggaactgaag agagatctgc ctgtccgatc tgctacttga ctgtatctgt    19560
cttgtcagat acacagtgca gcacttgctc tttcaggcca cggtcacctg aggcactggc    19620
```

```
accagagggt gcaaagcact acttactgac tgtctgacca ctgccccgcc agattattct   19680
cctcgtgagt tatcagagta gatgtccagg agaactctgc caaggttttc cctgtgaaga   19740
gagccaagac cagaaatgag actcgagaga ctctaggaaa gggaaaattt gatatacagg   19800
ctgttacttt cttttttctt tttctttctt ttttttttttg gttttcgag acagggtttc    19860 tctgtaaccc tggctgtcct ggaactcact ctgtagacca ggctggcctc gaactcagaa   19920
atccgtctgt ctctgcctcc cgagtgctgg cggctgttac ttttctgtaa caaaataaag   19980
ggctcacttt gttctcttta acatttattt tgtgtgttag ggtgcacatg tggacagtct    20040
gtgggaatca gttctccctt tctacagtgt aggttctggg ggttggcctc aggtcatcag   20100
ggttggcagc cagtgatcac caatggagtg gttgtaaggg cctgggactt tcttttatgg   20160
tgatgagggc atctcagaga ttcagactct gaaaagttat agcctcagaa acaagtagct   20220
tcctgcgaca ggggaagctg ctcagcagca gcaagagaaa ctgtgcttgg ttcccagcat   20280
gcatcaggca tggcaacgct caccgtgagc ccagtgctgc agaggtgcag agaaaggccc   20340
cgagtttgct gccaactctg ttcagcctaa ttgcagagct cctcagttca gtagacattg   20400
tctgaaaaaa acaaggcaga gggcaataca gaaccagaca cacagagggg agcacacaga   20460
aaatacaagg cagagccagt atctacacat acacaataca ttcattcaaa cctatacaca   20520
cagacattcg caaacacatg gaaacataaa ataaaatata gatagatacc ttcctattac   20580
acagctttat tttagattat ttctcaggca aatacaaaaa caacctaggt gtgcctggtg   20640
gcacaggctt gtaagctagc tgcgtcaggg attgagacaa ggcttgtaag ttcaaggcct   20700
gcctggctat acagagtgag ttcaaaacca gactgtgtca ctaagtaaga cccagtcttg   20760
aaataaaaag ttttaaatgt gatgtaggag tggttacagg tagtggtaga atactgaggt   20820
ccttgatcca gtaccttattg cctccaaaag aagacaacag tttcctgtgt gaacctttct   20880
acttaatatt ttcctgtaag cagtcaccta gccagggtga agtaacctgc cttttcctgc   20940 cttttgtcctt aggagccaat gaagtgcttc tggtggttgg gggcttcgga agccagcagt   21000
ctcctattga tgtggtagag aagtatgacc ccaagacaca ggagtggagc ttttaccag    21060 taagtcgtgg tggaaccatt tccagcagag ttgaaatgtc attggctcct gacactagct   21120
catatgtgac agctttgaga gtagaaaagc ctcagaacag cagaatgcat gtcccttcca    21180
gccatgctgt agcagaatgc atgtcccttc cagccatgct gtagcagaat gcatgtccct    21240
tccagccata ctgtagcaga atgcatgtcc cttccagcca tgctgtagca gaatgcatgt    21300
cccttccagc catgctgtag cagaatgcat gtcccttcta gccatgctat agcagaatgc    21360
atgtcccttc cagcatgctg tacgggttgt tctatgtgtg tgtctacaca tgtgggcatg   21420
tctgtgccat agccatctgt gtgaaggtca gagaatcatt ttcttctctt tttttttttaa   21480 gatctattta ttttatgtat atgagtactc tgtagctgta cagagggttg taagccttca    21540
tgtggttgtt ggaaattgaa ttttaggacc tctgctcgct ccagtcaact ctgcttacaa    21600
agtccctgct cagtctggcc caaagattta ttattatgca taagtacact gtagctgtct   21660
tcagacaccc cagaagaggg catcaggtct cattacaggt ggttgtgagc caccatgtgg    21720
ttgttgggat ttgaactcag gaccttcgaa agagcagaca gtgctcttac ctgctgagcc    21780
atcttgccag tcccagagaa taattttcaa gaatcaaatg tgggttatca gccttagcag   21840
cagacacctt tacccagcaa actatcttgc tggtcccctt ttatttgttt gtttggagac   21900
atctcactgt gtatcactta caggctcctt acttcctgaa actgtcttgc tgacacacac    21960
tggctgtgta accctggctg gcctcacgct tacaggcttt cctcacactc ctgagccagg   22020
```

```
gttgcacacg gagccaccac acttggcttg ttttttgaga taaggtcttg ttgtacagct    22080
ctggctggcc tgatactcaa tgtatagccc aggctgacct taaattatgg cagtcctgct    22140
tcaggctgac aaatgctggc attataggca tgtgccacca ccatacacaa cttagtttct    22200
gactgttcca attagaagtt ctcattgtgc ccgacgtggt ggcacacacc tttaatccca    22260
gcactcggga ggcagaggca ggaggatttc tgatttcgag gccagcctgg tctacaaagt    22320
gagttccagg acagccaggg ctatacagag aaaccctgtc tcaaaaaaca aaacaaaaca    22380
aaaaaaattc tcaccgcaga agtgtcagta accatatatc gtttagctgc caccaccatt    22440
aaggctgcac aacttatacc attgttcatg ctctgctaga ttgaacttgg ttatgttgaa    22500
tctaactcct gtttgactga aaagttaagt ctcatttcag catttcagta ctttacaacc    22560
aagaaccatt tctgaggaga catggaaaac ctttgaagcg ttcttatcct ttagggtatt    22620
tcagactggc tccaggatta gcagtatgcc tgcactttc ttatggaaag atattcagtc    22680
tcttagctca gtgccttaga gaagacagta gaaagccatg gtgtcttata taaacttccc    22740
aatgaggcag aagcatttca ctctataggc attcaccatc tagcccctca ggatgaaccc    22800
cgaagggggt ttccgatggc agggaagaag caaagaagat taaaccaggc agggtgcagg    22860
agaggtggga ctagagtgtg cccatttgaa tggtattact cctcttcttt cccaaatcca    22920
cagagtatca ctcgcaagag acggtatgtg gcctcagttt ccttacatga tcggatctat    22980
gtaattggtg gctacgatgg ccgttcccgc ctcagttcgg tggaatgtct agactataca    23040
gcagacgaag atggagtgtg gtactctgtg gcccctatga atgtgcggcg aggccttgct    23100
ggagccacca ctctgggagg taggtttgat aacaaacaat gtttcatgtg ctcttctact    23160
gtattgtagg aacataatta aatgtctcat ttcaaaggct cattcttgct tttagaaatg    23220
tctttgttaa cagaaactat tcattatttg tagacttttc aattctgact acagacctgg    23280
tgcttcatgt tttgttatgt tgtgtggtag taggtactga tgatgtttta gaaactccga    23340
gtggacagtc cagatgcctt tagtattcct cttttgttgt tgtttgtctt tctagagaag    23400
agtttctttg tgtagccatg gttgccccta aattcccttt gtagacgagg ctggctttga    23460
actcaagatc cacctgcctg tgcctctgga gtgctgagat ttaaagtgtg cactaccacc    23520
acccagctct tttttatgc caggtgtggt ggcgcacgcc tttaatccca gcattcggga    23580
ggcagaggca ggaggatttc tgagttcgag gccagcctgg tctacaaaat gagttccagg    23640
acagctaggg ctacacagag aaaccctgtc ttgaaaaacc aaaaaaaaaa aaaaaaaaa    23700 aaaaaaatta acatcttgag atggagtttg ctagatttcc ccgtgtaact caccettgtt    23760 tcaaacttgg gcttaccagc atgggcttta aatgcttgtt tgtactgcct ttcttccttc    23820
tgagacttac atgacttacc atttaagtca cgtaagtctc agaaaatata tacaaaatat    23880
acatttacaa gaatgtgctt atgtagtatt atacactacc atatataatt aatatacacc    23940
atgggaaatt taagaataat aaaaatcaac ttgaagaaat ataataattt gtttgcctgg    24000
gatgagttct gaaatagcta aggcttaact tagtctgtag ccaggaatgg ccttgaactc    24060
ctgaacctcc ttctgaacct cccaagtgtt gtaattacat tcatgtgtgc agtccctctt    24120
cccccatctt aacaatgggt aatttgtaga gataaaagtt gttaggtatt tttcattctt    24180
aatttaacag tctataattt gttcactctg agcagatatg atttacgtct ctggaggctt    24240
tgatggaagt aggcgtcata caagtatgga gcggtatgac ccaaacatcg atcagtggag    24300
tatgctggga gatatgcaga cagctcgaga gggcgcagga ctagtagtgg ccagcggaat    24360
```

```
aatctattgt ctaggtatga gcctgggatg gggctggaga gagcttagtg gttacagact    24420
ctggagggca gaattaagtg catatacttg catcaacaaa aactctgact tttctcaata    24480
tattgtccat gaataggatt atattttttct tgtaagcaat atgtaggatg ttgcatattc   24540
tctgacctgg acctctggaa aaaatagaac tgaaagaatc agttgaatta gggctagaga   24600
gatggctcag cagttaagag cactgactgc tcttccaaag gttctgagtt caaatcccag    24660
caaccacatg gtggctcaca gccatctgta atgagatctg atgccctctc ttctggggtg    24720
tctgaagaca gctacagtgt acttacatat aataaataaa taatcagttg aattactcac    24780
agaaggccaa ctaagatgag cctggtaatc taccttctc tttggaatgt tctccacttt     24840
gtctttcagg aggatatgat ggcttgaaca tattaaattc agttgagaaa tatgatcccc    24900
atacaggaca ctggactaac gttacgccta tggccaccaa gcgttctggt aagaccaaac    24960
ctatgaagtg atggtttaat tactgggtgt ggtatcagta ggacagaact gtagttctta    25020
tttcactgta gacccattgt gaatgtgagt cacagtccag tctcctccac ctctgccttc    25080
cctacaacat taggatgaag gaaggtaggt taaactttga gctagattgt ccatttgagg    25140
acagcgattc cttattcttt agtacttttt tctattcttg tagtttgacc actagcctca    25200
ttttgtgtgt gcagtacatg ttaaataaat attttttgtac acagacctgt tgaggtctat   25260
gtctttgctt tttgtactct ttggatgttg atgtcttgct gttttaaaga cagggtttgc    25320
ctgtgcagcc ccggctgtcc tggaactcac tctgtagacc aggctggcct tgagcttaca    25380
gagatgcacc tatacctgct tctgcctcct gagtgctggg attaaaggcg tgcactgaca    25440
aacctggctg gactttgttt tgagggtcct actgtgcagt cctggccagt gtacaagttg    25500
ctatgaggtg atcctcctgc ttctggcttc aagttatacc actacactca ttggtgattt    25560
ttttttttta atctaagatc tcactgtatg tagtatatag ctcacattaa ctttagactc    25620
caagtaatcc caggattgca cacatgtgac atatacctga taataaatgg caataagtat    25680
tagataaaat ctctaatgcc taaaaataat tttttttaaa ttctgaatac tgcacgcagg    25740
gctttgcata tactaggcaa gtactctatc atagaggtac atctaactct aacagctgag    25800
aactcttagt tgaataggct gtgatgtaac tgcctctgga cagagatcac agcagagcca    25860
tggccttggt tcctctcatt gtctctaaca cagaagagag atagactgtg agttagtgac    25920
agcagagatg agacccatgt cagtcttctg ctagaatttc aggccctaac ctaagggttg    25980
accaatgcac acactgacat ttgctgtatt acactgttgt agtgctttga catgtgtgca    26040
tccctcatct ccacagtgca gccgttagcg gccgtgtttg ttactgggtt cagatgctag    26100
gcttactgcc attcatgtgc tgatgctctc ttttcccag gtgctggagt agccctactg     26160
aatgaccata tttatgtggt ggggggtttt gatggtacag cccaccttc ttctgttgaa     26220 gcttataaca ttcgcactga ttcctggaca actgtcacaa gtatgaccac gcctcgatgc    26280
tatgtagggg ccacagtgct tcgagggaga ctctatgcaa ttgcagggta agggttttga    26340
aagtgggcta gaatcatgta tccaaggcaa gaaagaatcc atttgggatg gaggtgaaat    26400
gtgtgttgtg gggaacaacc actggggctg ttttttcatt cccgccccag tgtggggagt    26460
gggcccttgt agacaagtgg taggacttgt atgtaaagtg atggagacct catttctttc    26520 tttgttttc ccatcagata cgatgggaat tctctgctga gcagcattga gtgttatgac     26580
cctatcatcg acagctggga agtagtagcc tccatgggaa cccagcgttg tgatgctggt    26640
gtgtgtgttc tccgagaaaa gtaactgtta ttttaacacc agctggagcc agtgactact    26700
ccaaggaaca gtttgtggga gaatcaagga tcctttccag aatgtttatt cctcactgtg    26760
```

```
tgcacagggg gattccaggc accagtgctg agatgatgat tgtacttgtt tgatgcacac    26820
tctccttcgc actggtcatc ttgctcagaa gcatgggggg gggcaggtac tccagggaag    26880
agaatgcacg tttggatgtg ggaaaccaga tcatggctct ctgtggtctg aggagcactt    26940
tcttactgtt tctaacttac catgtgcttg ggaggatgta tgtatgtatg tttgtatgga    27000
tgtatgttgt gcctcatata ttgcagagaa taaggtgagt atggcctgct agatgtgggc    27060
agtgtccatc ctaggtgatt ggaaggatat cagtttatac aagcttggta aaatgaaagt    27120 cttttttccct ctcagaagca aaaatacctt ttctaaatac agaggtagct caagccacca    27180
cagttccttg ctgtaggaaa acactatcac tgttaaaatt tgagaggcca agaaggaaga    27240
ttcatgctgt cctcacttag aagacattg ttggtgcaga gatttgaata agtggctgga    27300
gctgaatgga atgtaggtga acccagaaga tcactgaagt gtaaattgga aggctggaaa    27360
ggacatgtta tttgatttca cagtctttct aatgtaaaat gttgtaccat cttggcactg    27420
gagacttgag agattaacag tggaaaaggt tagaataaga gatgctgtaa atgtgcagag    27480
ttcaatatac ctgtggtaaa ctagaaatat ctgtgatttt acaattgtct tagtccctgc    27540
cagggctcct atagcagtgg cagtttggtc ttcaaatggg tgaaaagacc atcttcctgg    27600
cgaatcaagt gctaccacgt tactacgcct ccacactatt tatttgggga tgggtggggt    27660
ggctgcagcc tagtagttca ggtacgtgat tactgccctg ttgtttaggg cacacttcca    27720
ctaaggagtg cttaagactg ctgtgtgtgg tatgttcagt tttcttcctg ctatatcttc    27780
tgtacctgtc tttacagtgt attttactca tcctgaaaca aaataatcaa ggacaattga    27840
aaatcttttg ttagtttcta taccttcgta tagaatggca gttctaggca cctctgtgtc    27900
gtggtgaaac tcttgagtta ctggtatagc aaataggaga atgtggcagc ctaaactggg    27960
ctacactttc cttttgctct ggaatcccac ttttcctctt tccttgaatt gtgtttgctg    28020
acagagttaa tttcctttgt attttttttaa gaaaacatta aaatggactg tctcaaatgg    28080
ctttaagaga atttgtgggt agtgctgcct tcagcagaca tgttgaagga catctaagct    28140
caaggtcttt catctaccct gtttacctta tgcctgccaa caagctcagc tgcttctctg    28200
gcagcatcag taaaatgttt gcccaaattt gttggattta ttgtcctttc acactgtgaa    28260
tctacatgaa aaagatgcag gagcgcatga ggtggcgcac acctttaatc ccagcactcg    28320
ggaggcagag gcagttggat ctgtgagttt gaggccagcc tggtctcaca gagtgagctt    28380
caggacagtc agggctacac agaaaaaccc tgactcaaaa agcaaaaaga taaagcagca    28440
gccttgagca gttttagcac acatgaattt tagggtttta gtcactctag tagacttacg    28500
tgtttgcttc agttaatggc atgtgatcat acagatagct gtgttacagg cttgccaca    28560 caactgagct ctggctgtcc tgaaaacttg atatgtagac caggctggca ttgatccacc    28620
tgcctctgcc tgcccaatgc tagtattaaa ggtgtgcacc accataccca gctaaaacca    28680
caagtctctc tcggtctcag agccaagaga aagcaggaca agaggatcaa gaggatcaag    28740
ctatttgtct gtagcagatg tatgtgccag cttattgaac cacagcctgt gaaatgtggt    28800
tcatttatct ta                                                        28812
```

<210> SEQ ID NO 29
<211> LENGTH: 11067
<212> TYPE: DNA
<213> ORGANISM: mouse

<400> SEQUENCE: 29

```
gaggaccagg gaaggttggc gggtaggaga agaaaacaca agagaaagaa agggctgata    60
attagctctc aggcatcagt gctggtttct gaattttgag ccatgtccac agttcatgca   120
ctgaagccac cactgaacag ttacagaaaa ccaggaaata aaattcattg atttttttaa   180
aaatttgcat agctttacat gaaaaaaata tgttcataaa cagaattcca ttcatttgct   240
ctttcctctt taaaaaaaaa aagtatgtga ctatgttgca ggaaatatta aaaacgaat    300 tggcatgttc ctgccccagt ggcctggttg gccccgcact ggagggcaat ggttgacctg   360
ttgttatctc atgaagactc tctgcctcag ggctccaaaa tctctccacc cagctcgcta   420
ggttctcact ggcaggtcac taccacacta actccatgct tcaaatcccc cacggccttc   480
gtggtacacc ctgggcaaac ccatgctttg ccgccatacc tttctctctt gaacccagac   540
gagctgccct ctgaacaaac ttagttcaga acgatggta attcagtcac tgggcacaac   600
aactaaaatc ctaaccttgt aagccttatt aaacctaaat tctctggtgg cgaaacctga   660
cgcatgctcc attaaaaccg ggagacactt gtagctgcgt cctgtcctca tgctatcccc   720
atccaaaaaa gcctaactct ctcctgcttc ctctcttcct ctgtccaaca cggaagtccc   780
acttactcgc ccagtgattg gctccttat tcgttaggtg atggttcaca agaagtcacc   840
tgagtacatg actcattcct catttgcatc gagcaagtgc ttcccggaag agtggaatta   900
gcatcaaaat acaagcaaca gcatgaatgt gtatgtctat gtaacctgta cacccagttg   960
tagggcctat ggaggccttt ggaagggcag tgtctgctct taactactga gctgtccta   1020 agcatcccct ttgtgtggta gaggcagagg atagcctcaa gtattgttcc tcagatacta  1080
tccacctcgt ttttccttg ttttaattta gtatgagggt agctgtgtgt gtgtagtcag   1140
gacaattcag tagagtcaac tctcagactt ttatgcaggt tccagggatc tgactgcagt  1200
tgccaggctt gcgtatgcca ttgagtcccc aaaattccta aattttgtct ctgcccatca  1260
ctaggattac acgctagtgc caccatgact gaattgttct catgcttgta aagcaagctg  1320
ttcacagaac tcaagatcaa tcagtttcct agccctggga aactttattt gtatgatcat  1380
catctgagtt ctacacagtt ctgtcatagt taaatccatt cccttatgac gtaaagtaac  1440
tgatgtccta acctttacac ttttccacca ctgtctactt tatcagcagc tctttctgaa  1500
attcagatgt ggttaccaca gtgcttaata tagagccaat tattggcaaa tattgatgtg  1560
tttctgtccc caagctccat agatttccat atcttgtact gtaaagttca gtttccttaa  1620
catgcatcag atccgtggtg ttgagggggc atattctacc attccgatct cattagtaca  1680
gtctctctct acgcagaaat atgctttagt cgctggttta caaaccattc ttaagtttga  1740 tcccttttt tgtttgtttg gttttgttt ttgttttttt caagacaggg tttctctgtg    1800
tagccctggc tgtcctggaa ctaactctgt agaccaggct ggcctcgaac tcagaaattt  1860
gcctgcctct gcctcccaag tgctgggatt aaaggctgtg ccaccattgc ccagctttaa  1920
atttgatcct tttctagtgt accctgtgtc taaaatcttt cattcctgac aaccaaatgg  1980
ttaattaaaa tgatacctac ggggcctgga gagatgagtc atggttgagt gccagctgat  2040
gactgttctt tcagaggatc tgggctgggt tcctggcacc catgtggaag gttacaacag  2100
tcagtaactc cagttccaga catcttgtgc cctcttctgg tctccacagg cgcaaacaca  2160
atgcacttac atgtaagcca aacacttata aaaatatct ttaaataaat aagtgggtgt    2220
gcagtggttg tgcatgcctt taatcccagc taaggtggcc agatctgtct gagaacaacc  2280
agggctacac agagcaaccc tgccttgaaa acaaatacag agataaaag acccaacatc    2340 ctagacagct gtttcctaat ccatttctga aattgttcta ttatatttga gtctatgacc  2400
```

```
ttctcaggtt actattctca catacacaat gtccatcatc atgtaatgtg ggactaacag    2460
gggagcaaga ctgcattcta gaacagtaag gtggcttaat tccctcgttc tgatgtccta    2520
tacacattgc aaaccttagc cttcttcctg tattatgccc gagggcatac cctctaagga    2580
aatgacgttt tcaaaattac tataagcaac gctttgctac ctaataaatg ccactatta    2640 gtctaggctt aatattatca cactttcgc aacactaaat gtactaagca ttatacatac    2700
ttcttacata gaaagcaatt gttttgtatc taaatcttgc tgaggtgtga cctgacccga    2760
attatcgcca tctactcatg aggcaaggga aatatcccaa gagttagtgg taaggctagc    2820
catagtgatt tgcttaggcc aatattaagg gcgcctggga gaccaggtat agtgaaaaag    2880
gattgtcaca agtaactcct gacacttccg tccggcaata gagaaaggcg cctgcgcaat    2940
agagttcaga cgcctgcgca gaggtacagc gagaggcacg ggcggggcgc ccccagggac    3000
ctgcgccagc gtagttccgg gtgagccagc tcagatcgcg cgtgcgccgt tgtggctgat    3060
ggtgtggcgg cacggcgatg gaaccctgcg agctgcagaa cgagctcgtg tcagccgagg    3120
gccggaaccg gaaggcggtg ctgtgccagc gttgtggctc tcgggtgctg cagccaggga    3180
ctgctctttt ctctcgccgg caggtaggaa agtgcttgat gctgcttaga gtcgcgctgt    3240
cctgagcgac ccagcggctc cgggttgctc ctggttccca ggtttccgga gaccgcgccc    3300
ttccttgcgc gtcttttgccc ctccccgcgt cgtgaggccc cgcccactgg cttggttggg    3360
gactgggacc ctcgtgtcga ggcacagttg cctggtcccc taaactgttc tctctcgcag    3420
agtactccct cagagggtgt gcctgtccta ggcggcccac ccgcccccag gctttgggta    3480
tcctgcgcga gctaagggac gaaccctagc cccctgtttc ctggagctct ggctaacctg    3540
ctgtaccccg caggtgtatc tccagccacc actcggtgtc gccccagggc acctaagaat    3600
cactggattt ccttcccacc atagctttta tccatctttc agtccctact tgtctcattt    3660
gcttctcccc agaggagctc caggatcaag tttggtggag agaattcaca ccgagtgact    3720
gctagtaccc aacttttcta agtcccccga gatacaattc ccaggacgag gcatttcgaa    3780
tagatttcga aggttaacca ttcttttctt gcagttagga cttttttcatg taggattttg    3840 tgtgtgtgtg tgtgtgtgtg tgtgtgtgaa aggtttataa agttaaattt taattaaagt    3900
gaaagagaaa gcacactcct gatgataaga ggtaatctgg aatctgaatc ctaagggtcc    3960
cccacccccg tgtgtgtgtg tgtgtgtgtg tgtgtgtgtg tgtgtgtgtg tgtgtgtgta    4020
tgtgtgttta agttgtttgt tgtttgaca gggtctccct atgtagcctt ggctggcttg    4080
gaacttgctc tgtagaccca gctggcctct aacttaagag gtccacctgg actccccact    4140
gctagggatt aaaggtatga gccgcgtatg gtagggtttt aaaataagtg tcttaaacca    4200
ccatcacccc aatgagaaaa ctgaagaaa aaaaagttt ctgagccctt ttttttaagt    4260
gtaacatgcg atcctattgg atagtacaaa ctaaattgct ttcagaccct cattataaat    4320
ggtttgtaag aagccactgt tctttcaagt ggtggagagt cacatacagc agtgtctgct    4380
gcaagagcgt gttctgatgg ccttgtctgt ggagtgggtg gaagtccgtt ttaataagaa    4440
ctactcggac aggtagtaga gttctccact tatttttgtaa agttagtggc cttgcggagg    4500
gatggagctg agccagggaa ctggatcctg acctgcgcac ttattaacac cggaagagct    4560
gttgaacctc catgaccttg cgcttgctcc ttctgaccaa gttgatgaat agggagattt    4620
ggcactgtga gcacagtgcc tcctatatgg gacagttctt gttctcgaat ggcagcttgc    4680
ctgcttgtgt aaattgacag aaacttaaat gttcccgaat ggcatgtggt ggcctgcgcc    4740
```

```
tatcttagca cttagggctg gctacccagt gagatcaaag ctaaaagggg tacataatga    4800
gaccctgtct gtgaactgag taactctttt ttaaaaagtc aagacatttc ttaaaagaaa    4860
ttttgtagta gtcaggtgtg atggtgcaca cctttaatcc cagcactctg tggggtaggc    4920
gagctcagtg agttagaggc catcctggtc gacatagtaa gttccaggtc agccaagact    4980
attacacaga gacaaactta tctcaaaaga ccaaaaagaa gaaagaaaga aaaaaaaga     5040 tagtttatag ttacagtttt tgtgtcatgt gttttaaata gatgtttcat aggagggaac    5100
ctgtaagcaa attaaactgt atattacaaa tcatattttg tttctcaaca gagtaccttt    5160
acagagaaca aaccatttgg aacacacatt tttaaaactg aatccctatg aagtgtcaac    5220
atggctcttt agtcgttccc tggactgttg agaaattact gtgaggccag tctaggcaag    5280
ctgacactcc gccctcttag ggatgacctt ccaggaggca ggaggaaagt gtctgagcag    5340
tctggttctc tctgtaggct gacctcaata taggaaaaaa ttaaaacaa agagaagatg     5400 cgaagatgcc cttccaggcc tagagagttg gctcactggt taagagttct tgaagcacat    5460
gtcaggtgtc tcacagttct ttgttgctcc agttagttgg atctagggga tccagcatct    5520
ttttccaccc tctgcaggca ccagacatgg gtatgataca cacatgcagg caaagcgctc    5580
ataaagtaaa aataaataaa tctttaagat tataaaagca gttcttgcca ggcggtggag    5640
gtgcacgcct ttgatcccag cagttgggag gcagaggcag gcggattcct gagtttgagg    5700
ccggcctggt ctacagagtg agttccagga cagccaggc tacacagaga aaccctgtct      5760 caaaaaaac caaacttta aaaaaaaaa aaaaaagca gtcctttcac catttaagag         5820
aacctggaga gagacagggc atgaagaggt ctccttagag gtggcccata gcattttcac     5880
ctgtaaggta gtctagtgta gtctgcatgg caaagctctg aaaaccatcc cagcatcgac    5940
atgatgcagg acctggtgat aactctgccg tgcatttcat agtctaaggc agtatgtttt    6000
ccacctggga gtaagttttt ccccaaaggg aaaagtctag agacaaacac agatattttc    6060
catggtaaga attgggaagg ggtattactg acttcagtag gctgctgtct tgtgtcatgt    6120
gaggctaccc ctcagagcta agaattcttt ggcccaattt ttcagaaagt caaagttcca    6180
gaaaccctag accctacatt gcaaatatct ggcacctctg ctacctcagt tgacctcttg    6240
gtaccttttg ctacttacac cactagactc tgagggcctg tgtcctatcc acgtgtgtat    6300
cttctatacc caggctgtgt gcatagtgag aacttaggaa ataatttggt cttcataaaa    6360
gctattagtc tggggtgaat aacggattat tattgatata ctggatcaga attttgtggt    6420
tttaccctcc cctccccct ttctaaagtc agagtcttat aaagccacgc cagccttgag      6480
ttctctgtgc gaccaaggac ggtcttgaac ttaacaatcc ttctggctta caggcatgga    6540
ccactgcccc agtatgttct cctgggtatt gcacttatga tagactttat gcctgcttga    6600
caagaacttt gccaattgag ccacatccct ggttcagttt gattggcacc tttactcctg    6660
tttgcagcag acaatctggg ttgttttttt tttttcagtc atagaatcgg ttccccatag    6720
aaaatattca taccatactc tctctcagga ccaatttctt ttgtttgttt gttttttcga    6780
gacagggttt ctctgtatag ccctggctgt cctggaactc actttgtaga ccaggctagc    6840
ctcgaactca gaaatccgcc tgcctctgcc tcccgagtgc tgggattaaa ggcgtgcgcc    6900
accatgcccg gctcagaacc aatttctgtc ctacttcagt tcctgtgatt tgataaaggc    6960
tggaccagaa gcgcttggag aggagagggt tcgtttggtt acctgtccat taactgaggg    7020
aagccaagac agaaactcaa gcagagcagg gacctgaaac agaccatgga ggaacggtgc    7080
ttgctggcac tcctaccacc caagctccca cagagcagcc ctccatgctc tgagcactca    7140
```

```
gtggctttcc cagcccaaca ttccaaacac ttccacagtt ctcctcaaaa catggtgatc    7200
acagcaatag cccaccctct gctactgact tctgttttag tttgatttct gtggctgtgg    7260
taaacacagc caaaagcctt aggagggaaa tgttcattgt atcttagctt acagttcatt    7320 atgagggaa gtcatggcag gagccaggag tcaggaccct ggaggtgggg ctatagagga     7380
gagctgctct gctggaccgt ggaggtgagg ctgttttatt cccccccccc ccccgccatt    7440
gtttgctcag cctgcttttt atatagtcca ggaccatctg cctaggggga cactacttac    7500
agtggcctcc cacataaatg tcccatcaag aagaatgccc cacaatttac ctgcaggcca    7560
atctgattga gacattttct caatcaaatt ttcctgttcc aggtgactct agcttgtgtc    7620
aggttgacaa aaacaccca gcatactttg gaccaaaact gtttcaggat tcaggggtgg    7680 gattttttcgg ggtgggatgg aggaactttt tgcaattaca cagtgaagta tttttaggctt   7740 gagagacaga tctaaacatg gaattctttt gtttcatatc cacctgtcta cataaactga    7800
agacaagttg atgtattttt ggtgagcctt tattttgctt aactcccatt ccatgacact    7860
gacaatggag ttttctgctt gtgtcatggc agtgctctta aaagtttcaa acactgggc     7920 atttcaggct ggatctggga actgaggaat tcagacttt cacagtcttt taaatgttct    7980
taattatgtg tgtgcttagg cttgcgtgtt tgtgtgtaca tattacatgt gtgcaggagc    8040
tcttggaggc cagaagagag ctttaaatcc ccctggaatc ccctgtatt acaggaggtt     8100 ttgagccacc tcatggattc tgggaaacaa actggatccc ctggaagagg agtgtgtgct    8160
cttaaccact gagcaagtct ctctctctct ctcttttttt tttttttttt tttttttttt    8220 tggttttcg agacagggtt tctctgtgta gccctggctg tcctggaact cactctgtag     8280
accagcctgg cctcgaactc aaaaatcctc ctgcctctgc cttccgagtg ctgggattaa    8340
aggtgtgtgc caccactgcc cggcctccag ccagatttct aataacctta aagttgttga    8400
aaatgagaca cagtgacatt tcctaatttt aaatatagtt tagaaactgt taagtttcct    8460
tagccagaac agaggttctg gagccatggc aatgagccct ccctgtaaat gggattgaag    8520
gaagactggg gcaggagcca ctccatctac aatggaaagg gcagagtggt cagagcttgc    8580
ataggtgacc aaacgtgaca ggttactaaa tgggagaaac cttgtagggg taaagtgctg    8640
agttaatgaa ggatcagctg ggagcaagag gagtatctct ttcctctcca ggtctgagag    8700
tgtagactgc tgggcaggag ctgtggtctc actctggccc tcactcctat gcagagaaaa    8760
agggaaactc cattgagttt ggaaattaga aaaaagatg atgatataga agagagatgt     8820
ttgattgtag gaaggaaagt ataaactctg ctggggtaga aagacgcgc agcacttaga     8880 gtacctgtta ctctccgcag aggacccaag ttcagttccc agcacataca tgggattcta    8940
aacatgaaat aaaagtgaat aagtcttaaa aaatttacac aaaatagtac tgggttaaac    9000
atattggagc agagagcgtg aaggcagtaa ccatgaacag tttcttataa aaccactctc    9060
gtggttaaca aatgagtggc actatgtgtt attttttccca gggaaatgaa aacttacatt    9120
catgacaaat gtgcagtgaa tgtgtgtagc aactgcattt gttatagctc caactggagg    9180
cagcacagat gtctctcagt tggtgagtgg agtactagtc agccataaac acagactacg    9240
aactacactt tgttctttgt gtgtgtgtgt gtgtgtgtgt gtgtgtgtgt gtgtgtgtga    9300
gtgtgtgttt tggttttttag agacagggtc tctctatata gccctggctg tcctagaact    9360
cactctgtag accaggctgg cctggaactc agaaattcgc ctgcctctgc cttgagtgct    9420
gggattaaag gcctgtgcta ccacacctgg cttgtgtttt tgttttgagt taacagctct    9480
```

-continued

```
tgtaattcag attggcctca aatttgctct gtagtggagg gtgaccttca actccccatc    9540
ctcctgcctc taccttccag ggttgggatc acaccaccac agccagcttg aaggagtcta    9600
cagagaatta ttctggtaag aaagccagtc ctcacacttc ccagcttttg aatctctttg    9660
tataaggttc cctctccatc ccactcctct gtttatttga cacagagtct cagtgctggg    9720
aaggctggcc tgcagacttg aacttgaaaa tcttgaagat ctcacttcgt tgatctttcc    9780
tggactagag tgtgccatca cgaggcccct cccctcccc gtgctctcgt gtgtgtgtgt     9840
gtgtgtgtgt gtgtgtgtgt gtgtgtgtgt gtgtgtgtgt gtgtgtgtgt gtgtttaatg    9900
tgagacaagt ctcatgtaac ctatattggc tttgactgcc ccacccaccc ccatgtacca    9960
atgtagttga gaggatgacc ttgaattctc aatgttcatc taagtgctag gagtacaagc   10020
atggaccacc aagcctagtt tatattgtgc tggggtccaa acctgggggtt ctatgcatgg  10080 tagacaagga gctctgaaag ctgatagttt actgccacct cagcatccca cctagctggg   10140
attatagatt atatccctgg ctcactggaa ctagctaagt agaccaggct gcctctgtct   10200
ccaaagtgct gggttaaaag gctctgtgct actccttaaa aggtttatga gccgggtgtg   10260
gtggcgcacg cctttgattc cagcacttgg gaggcagagg caggcagatt tgagttcaag   10320
gccagcctgg tctacagagt gaattccagg acagccaggg ctacacaggg aaaccctgtc   10380
tcaaaaaaat aaataagtaa ataaataaga tgtatttatg ccttcgtttg tgtgtgtgtg   10440
tgtttgtgtg tgtgtgtgtg tgtgtgtgtg tatgtgtatg tgtgtgtgat gcatgtgtct   10500
gcaagttcta gcagagtcca gaagcaagca tcagatcact tggagctgga aacgtggag    10560 ttttgagtca cctgacgtgg gccctggaaa acaaactagt cctcggaaga atggcaggtg   10620
cccttggctg ctcctgaact agctctctgg gtttggttgt tggcttttga gacagggcct   10680
caacgtgtcg ctctgactga ccttaaagtt atccacctgc ctctgctgag actaaagaaa   10740
ggcatatgcc actatgccca gctctttagg ttattaacac taaatatgag cttgttggga   10800
cattaaatga aacaagccag tcagaaaagg ctgtgcacag gccaatcgct cgaacaggaa   10860
atgtctagaa ctgcctctgt agaggacagt gagaggcagt tcagtgggag cagagtctcc   10920
gtttgggagg atgaagcagc agctcagctg ctggctgttg actgtggcag tacagtcctg   10980
tgaacattct tatgtactga actggacaca gagaaatagt gaggactggg gaggtgcctc   11040
agcacttcca gaggacctgg gtttggt                                       11067
```

<210> SEQ ID NO 30
<211> LENGTH: 46
<212> TYPE: DNA
<213> ORGANISM: artificial sequence
<220> FEATURE:
<223> OTHER INFORMATION: primer

<400> SEQUENCE: 30

```
cccatcacta tcaaagacga caagggcaat ctcaaccgct gcattg               46
```

<210> SEQ ID NO 31
<211> LENGTH: 32
<212> TYPE: DNA
<213> ORGANISM: artificial sequence
<220> FEATURE:
<223> OTHER INFORMATION: primer

<400> SEQUENCE: 31

```
cctgttgccc agaacagtga cagattcttg gc                              32
```

<210> SEQ ID NO 32
<211> LENGTH: 239
<212> TYPE: DNA
<213> ORGANISM: artificial sequence
<220> FEATURE:
<223> OTHER INFORMATION: poly(A)

<400> SEQUENCE: 32

```
tagataactg atcataatca gccataccac atttgtagag gttttacttg ctttaaaaaa      60
cctcccacac ctcccccaga acccgaaaca taaaatgaat gcaattgttg ttgttaactt     120
gtttattgca gcttataatg gttacaaata aagcaatagc atcacaaatt tcacaaataa     180
agcattttt tcactgcatt ctagttgtgg tttgtccaaa ctcatcaatg tatcttaac      239
```

<210> SEQ ID NO 33
<211> LENGTH: 359
<212> TYPE: DNA
<213> ORGANISM: artificial sequence
<220> FEATURE:
<223> OTHER INFORMATION: probe

<400> SEQUENCE: 33

```
gtgagttgtc aggtgatcca ggaagagacc ttctgcaatc cagtgaccaa ttaattacag      60
cagaaaggac catcgggaag gaaagccata ctctccagga acgtcattag tcgggatctt     120
cagttgctac aagaagcaga tgtcaaacgg ccttccccta accatgtgag aagtgagctt     180
tcactggccc gggtgtgaag tgattctaat ggaataaatg gatttgctaa ggaatagttt     240
cctcagaaga atcctggga gcaagtgggg aaagctgact cagcaaaaca gagctgtttc     300
ttgaggacga tgccaatagc aatcatttga ccaaactgaa gtggccgtca ggaggcatg     359
```

<210> SEQ ID NO 34
<211> LENGTH: 527
<212> TYPE: DNA
<213> ORGANISM: artificial sequence
<220> FEATURE:
<223> OTHER INFORMATION: probe

<400> SEQUENCE: 34

```
ggtcaacaga gcaactttca ggacaggcag ggctacacat agaaacccag tctgaaaaac      60
aaaacaaaac aaacaaaata attaataaat aaatagttga tgtttatctg taaaccctca     120
aacactcatc catggtccct tctcccctta gaggtgtggt ggtctctgtc tctgagtgtt     180
gctctagcaa ggtcggtaaa gcctaatgta cagaaggaag tggccagttg ggcctcagcc     240
accggcctaa acacgcacag ccaccagctg gctggacttc ctcacagctc tcaggccccc     300
accagggttc tggagcagct tcaactggac acagatcaga ggtgccaggc ctgtgaggca     360
ggcaagttgt tttactgctg ctgtcgaagc ctcctcagct gttgcttcct tctagtagca     420
gtcccaccca tcccatgagg agtaggagtt caaaggccga ccaaagacag gagccggatg     480
ggacctacct tagcagataa gcagcaatat ggagctcgga gttcctg                  527
```

<210> SEQ ID NO 35
<211> LENGTH: 459
<212> TYPE: DNA
<213> ORGANISM: artificial sequence
<220> FEATURE:
<223> OTHER INFORMATION: probe

<400> SEQUENCE: 35

```
cctcagacac ctccctggcc ttccagccac tagagggcgc tgcactttag tccactgagg      60
```

-continued

```
aaaccggtgc cctagaccca gccaaatggc tggcttatct ttagtacaca catgcaactg    120
catatgtctg gcacctcacc ctcttgtgga gttcttagaa gaacaggaga acctgcttaa    180
ggctcagagt catccctgac tacacaaatg tccacatggg cctgtgtaga gagaagccta    240
gggcaaccac ttccagcagt ggtgacctat ggtgtgtctg gggttctgtc cattaaatca    300
ggacaccctc acctctgcaa ctgcaggtgc agccccagtc ctcacgcact tcccttgggg    360
tctcaaggca ggtactgtgg gtcttaacat ctggaagaca ggacacaggt gtttagaaag    420
tagttctatt taggggttca cctccagagc agtagttcc                          459

<210> SEQ ID NO 36
<211> LENGTH: 459
<212> TYPE: DNA
<213> ORGANISM: artificial sequence
<220> FEATURE:
<223> OTHER INFORMATION: probe

<400> SEQUENCE: 36
gcatgctgag gcctctggac agtgaagcgg agaagccagc acctgaagct gaagtacccc     60
tctatatctc ttaagactca gagcaaaccc tctggttcgc tttcccatca gaccttgctg    120
ctgaacttgg tggtcataaa ggaaagagta cactgaagcc ggcctcacag tgatgtcgtc    180
agaatagaac atagggccag actcaaacaa gcctgaacac tgtgtactta ctatctgaga    240
gctaagtaca tctgttgcat gggaagttgt ggcctgttgt agcagtttgt gtggagttgg    300
ggagagatta taggggagag gggtttagat gtattcaact gtgaagaggt cctcatatga    360
tttggccaac agttggcaaa gcatcccagg gagggaagga gtaggcaggc agaaggacag    420
ctctgaaagt agacatgttg actaatgctg tgtaaccat                          459

<210> SEQ ID NO 37
<211> LENGTH: 528
<212> TYPE: DNA
<213> ORGANISM: artificial sequence
<220> FEATURE:
<223> OTHER INFORMATION: probe

<400> SEQUENCE: 37
gtacctgtca gtgtaatgaa gtagttgtta gacccagata aaagggaaa taggataaca      60 gctatatcta tgggcccagt taaactgcca tgtttgtcat ttactctggg ggtaaatatt    120
gccatttcat ttttcagatg aagggtctca acaaatgcct ttcaatgtca catcacttga    180
aaatactaca tagaggtagg ctttgcctct acagcatgtg gctgtaaaaa atgattctta    240
actgccattt cagccataag gctggtagga gaaatagaaa gcagtcaggc cgttgcggca    300
aatcctgact aatttaaaaa ccatcttgaa taatacaaca gcacagatct ctagcttgta    360
gtgttcttca ggatgtctgc ccccaaaaca ttagcattta gctgggtagg gagagttaac    420
cagaagtgct gagcatgaaa tggcctaagc ctgccaactg ctactacagt cctgctgaaa    480
caggacgtgt cctgcttgct gttgtcttga gaacatctgc ctgcactg                528
```

DIVIDING OF REPORTER PROTEINS BY DNA SEQUENCES AND ITS APPLICATION IN SITE SPECIFIC RECOMBINATION

CROSS REFERENCE TO RELATED APPLICATIONS

This application claims benefit under 35 U.S.C. § 119(e) of U.S. Provisional Application No. 62/300,966, filed 29 Feb. 2016, which is incorporated herein by reference in its entirety.

FIELD OF THE INVENTION

This invention relates to monitoring and visualizing genetic modifications by activation of DNA sequences encoding at least one reporter protein introduced by site specific recombination.

BACKGROUND

It is common to model human diseases in non-human mammals by modifying or deleting (excising) the specific gene or genes hypothesized to be responsible for the disease.

A commonly used technique is to remove the entire gene or an essential part of it in the animal model. There are at least two ways to achieve this. First, the gene can be removed from the germline stage, in early life, which is also called "knockout". In the knockout animal, every cell carries the gene deletion. As many genes are essential to embryonic development, embryonic death can occur.

To solve this problem, a second technique was developed, called conditional knockout, in which a specific gene can be deleted at a specific tissue and time rather than early in life. This is commonly done by activating the transcription of a certain recombinase, such as Cre. The recombinase will delete the sequence between two recombination sites when the sites are facing the same direction. Since the expression of the recombinase is controlled by its own gene promoter, the deletion of the target gene will be determined by where and when this promoter becomes active.

The commonly used promoters are not well defined in terms of where (e.g. in which tissue) and when (e.g. developmental stage or presence of physiological stressors) they will drive the expression of the recombinase. When researchers went back to trace where and when the gene was deleted, they faced daunting problems. As organs consist of many different cells and cell types, without a reporter, researchers could not pin-point when and where the deletion had taken place.

Therefore, there is a need to monitor and visualize where and when a gene is deleted in a conditional knockout model.

BRIEF DESCRIPTION OF THE DRAWINGS

FIG. 4 shows an exon trapping sequence that can be utilized in the method of FIG. 3.

FIG. 11 shows the green fluorescence generated in Example 1.

FIG. 12 shows the green fluorescence generated in Example 2.

FIG. 13 shows the red fluorescence generated in Example 3.

FIG. 16a and FIG. 16b show results of southern blot analysis for targeted ES clones of mouse Basigin gene.

FIG. 17 shows the green fluorescence generated by mating targeted Basigin gene with a Cre recombinase containing mouse.

FIG. 18a and FIG. 18b shows results of southern blot analysis for targeted ES clones of mouse KLHL12 gene and green fluorescence identified in mouse intestine cells FIG. 19 KLHL targeted mouse was mated with a IL17 driving Cre recombinase and green fluorescence was observed in mouse intestine cells by a confocal microscope.

SUMMARY OF THE INVENTION

Figure 1:
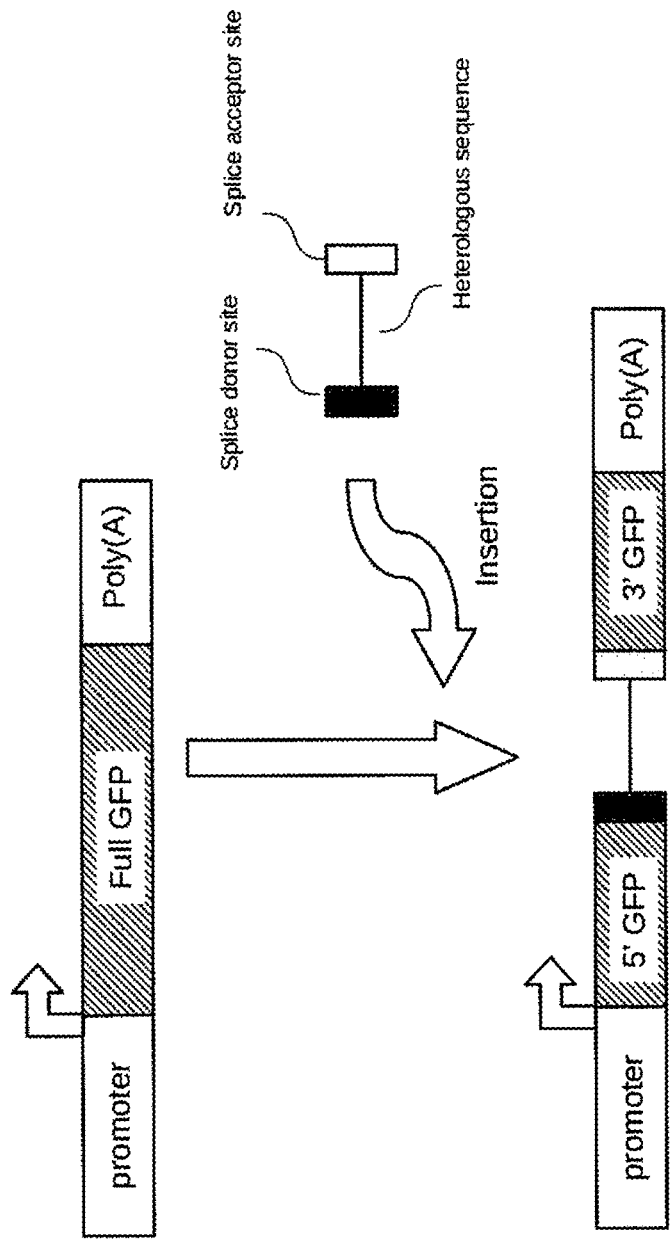
FIG. 1 shows a schematic diagram of an embodiment described herein.

The embodiments described herein provide a unique solution to problems associated with human disease modeling in an animal. Conditional gene knockout is a method often used to model human disease to avoid embryonic death caused by traditional gene knockout techniques. The conditional gene knockout method includes a site specific recombinase and its recombination site. The recombinase will delete or invert the sequence (target sequence) between two of these recombination sites. The expression of the recombinase thus controls where and when the target sequence will be deleted or inverted, which is difficult to identify. In one embodiment, a recombinant nucleic acid construct is provided, the construct comprising in order from upstream to downstream and/or operably connected, a promoter sequence a nucleic acid sequence encoding a first portion of a reporter protein including an N-terminus, wherein said first portion is insufficient to provide reporter expression, a splice donor site, a heterologous nucleic acid sequence, a splice acceptor site, a nucleic acid sequence encoding a second portion of a reporter protein including a C-terminus; and a poly(A) signal sequence. In an embodiment, the promoter may be a nucleic acid sequence capable of driving gene expression of downstream sequences in eukaryotic cells. In some embodiments, the promoter can be a polymerase II promoter. In some embodiments, the promoter can be a ubiquitous promoter, a cell specific promoter, an inducible promoter, and/or a constitutive promoter in eukaryotic cells In some embodiments, the promoter can be CAG (SEQ ID NO: 1), CAGGS, CMV, hCMV, EF1, PGK, FABP, Lck, CamKII, CD19, Keratin, Albumin, aP2, Insulin, MCK, MyHC, WAP, Col2A, Mx, tet, and/or Trex promoter. In some embodiments, the report protein includes fluorescent proteins and other proteins. The fluorescent protein can be a protein capable of absorption of a higher energy photon and emission of a lower energy photon in eukaryotic cells. In some embodiments, the fluorescent protein can be blue/UV fluorescent proteins, cyan fluorescent proteins, green fluorescent proteins (GFP), yellow fluorescent proteins, orange fluorescent proteins, red fluorescent proteins, far-red fluorescent proteins, Near-IR fluorescent proteins, Long strokes shift fluorescent proteins, Photoactivable fluorescent proteins, Photoconvertible fluorescent proteins, and/or Photoswitchable fluorescent proteins. In some embodiments, the protein can be GFP, EGFP (SEQ ID NO: 2), and/or DsRed (SEQ ID NO: 3). Other nonlimiting examples of reporter proteins include beta-galactosidase, luciferase, and chloramphenicol acetyltransferase.

In some embodiments, the splice donor site can be a functional DNA sequence which can be spliced by splicesome. In some embodiments, an intron sequence may comprise the heterologous sequence, the splice donor sequence and/or the splice acceptor sequence. In some embodiment, the intron has a 5' end (part of splice donor site), wherein the first nucleotide of 5' end of the intron can be a G nucleotide. In some embodiments, intron has a 3' end (part of splice acceptor site), wherein the last nucleotide of 3' end of the intron can be also a G. In some embodiments the splice donor site can be a functional DNA sequence which can be spliced to a splice acceptor by splicesome.

In one embodiment, a method of introducing conditional and divided polynucleotide sequences coding for a fluorescent protein into a mouse embryonic stem (ES) cell, is described, the method comprises constructing a DNA targeting vector comprising, in order and/or operably connected, a 5' homology arm, the recombinant nucleic acid construct described above, wherein the heterologous sequence comprises a target sequence flanked by two recombination sites, a 3' homology arm, wherein the DNA targeting vector further comprises an antibiotic selectable marker gene inserted between the 5' homology arm and 3' homology arm, introducing the DNA targeting vector into the ES cell, and selecting the ES cell for a targeted clone. In some embodiments, both of the recombination sites are identical. In some embodiments, both of the recombination sites are different or are not identical. In some embodiments, one of the recombination sites can be a mutant recombination site. In some embodiments, the recombination site can be a wildtype recombination site. In some embodiments, the wildtype recombination site can be loxP (SEQ ID NO: 4), frt (SEQ ID NO: 5), rox (SEQ ID NO: 6), Vlox, Slox, attR, attL, attP, attB, or IR/DR sequences. In some embodiments, the recombination site can be lox511, lox5171, lox2272, M2, M7, M11, lox71, lox66, loxN, loxp 5171, F3, F5, F7, FL-IL10A, Vlox2272, Slox2272, VloxM1, SloxM2, VloxM2, SloxM2, Vlox43R, Vlox43L, Slox1R, and/or Slox1L.

In an embodiment, a method of reporting gene deletion is described, the method can comprise constructing a DNA targeting vector as described above, generating targeted germline mouse, mating the targeted mouse with a recombinase expressing mouse, activating a fluorescent protein by removing the target sequence by recombination between its recombination sites. In some embodiments, a sequence encoding a second fluorescent protein can be included in the target sequence, such that removal of the target sequence also removes the expression of the second fluorescent protein, e.g., changing the fluorescence from the second emitted fluorescence to the first or indicating fluorescent protein emission, e.g., red changing to green (GFP). In some embodiments, the recombinase can be an enzyme capable of deleting or inversing sequence between two recombination sites. In some embodiments, the recombinase can be an enzyme capable of deleting or inversing sequence between two of its recognizable sites. In some embodiments, the recombinase can be Cre, Flp, Dre, Vcre, Scre, Nigri, Panto, PhiC31, and/or Sleepingbeauty transposase.

DETAILED DESCRIPTION OF THE INVENTION

The term nucleic acid sequence and or gene sequence refers to a nucleotide sequence having at least a minimal amount of homology therewith. For example, a specified SEQ ID can also include a sequence with 80%, 85%, 90%, 95%, 98%, and/or identical nucleic acid sequence, The term "promoter" as used herein refers to any polynucleotide sequence that can be capable of initiating transcription of a gene in a eukaryotic cell. The sequences of the promoter could come from, typically, but not limited to eukaryotic organisms, viruses, or man-made sequences.

The term "target sequence" as used herein refers to a nucleotide sequence having one recombination site on the upstream and downstream of the sequence. Upon the action of a recombinase, the target sequence could be modified from its original and/or native state. It could be, but not limited to, deletion, inversion.

The term "intron" as used herein refers to a nucleotide sequence present within the transcribed region of a gene or within a messenger RNA precursor, which nucleotide sequence is capable of being excised, or spliced, from the messenger RNA precursor by a host cell prior to translation. The sequences of introns suitable for use in one embodiment in the present invention could be naturally occurred or could be man-made sequence. The man-made sequence can comprise a splice donor and an acceptor sequence and other sequences connect the donor and acceptor sequences.

The term "heterologous sequence" as used herein refers to a nucleotide sequence, refers to a foreign, i.e. "exogenous", such as not found naturally in an organism in which genetic modification takes place. The sequences naturally occurred in the organism are called "endogenous" sequences. A nucleic acid sequence comprising the heterologous nucleotide sequence may differ in at least one nucleotide from the endogenous nucleotide sequence. Specifically, heterologous nucleotide sequences are those not found in the same relationship to cells of the organism in nature. In some embodiment, the heterologous nucleotide sequence can be completely different than the endogenous sequence. In other embodiment, heterologous nucleotide sequence is homological to the endogenous sequence.

The term "exon" as used herein refers to a nucleotide sequence that will encode a part of the final mature RNA produced by a gene after introns have been removed by RNA splicing.

The term exon refers to both the DNA sequence within the gene and to the corresponding sequence in RNA transcripts. In RNA splicing, introns are removed and exons are covalently joined to one another as part of generating the mature messenger RNA which in turn will be translated into a protein.

The term "fluorescent protein" as used herein refers to a protein is capable of absorption of a higher energy photon (excitation) and emission of a lower energy photon from a molecule (fluorophore) or more than one molecules inside the protein from prior absorption.

The term "recombinase" as used herein refers to a group of enzymes that can facilitate site specific recombination between defined sites, where the sites are physically separated on a single nucleotide sequence or where the sites reside on separate nucleotide sequence. The nucleotide sequences of the defined recombination sites could be not necessarily identical.

The term "recombination site" as used herein refers to a specific nucleotide sequence can be recombined by a recombinase. There could be wild type recombination site and mutant recombination site. Typically, wild-type recombination site occurs in the nature, specifically, homologous phage/bacteria system. Mutant recombination site refers to a site at which recombinase can facilitate recombination even though the site may not have a sequence identical to the sequence of its wild-type recombination site. A recombinase could bind both its wild-type and mutant recombination sites. In a broad embodiment, the term "mutant" as used herein in the context of the present invention shall specifically refer to any sequence derived from a parent sequence (wild type), e.g. by size variation, e.g. elongation or fragmentation, mutation, hybridization (including combination of sequences), or with a specific degree of homology, or analogy.

By "hybrid-recombination site" as used herein refers to a recombination site constructed from portions of wild-type and/or pseudo-recombination sites. As an example, a wild-type recombination site may have a short, core region flanked by palindromes. In one embodiment of a "hybrid-recombination site" the short, core region sequence of the hybrid-recombination site matches a core sequence of a pseudo-recombination site and the palindromes of the hybrid-recombination site match the wild-type recombination site. In an alternative embodiment, the hybrid-recombination site may be comprised of flanking sites derived from a mutant recombination site and a core region derived from a wild-type recombination site.

The term "exon trapping" as used herein refers to a nucleotide sequence contains a splice acceptor that forces splicing from any exon upstream to itself during transcription. Typically, the exon trapping sequence can be inserted into an intron directly downstream of an exon which can be intended to be trapped through RNA splice. The resulting sequence could get transcribed as a hybrid message with the initial portion of the exon and a hybrid protein can be produced.

The term "poly(A) signal" as used herein refers to a nucleotide sequence which is, typically, recognized by polyadenylation complex to initiate and perform polyadenylation which adds a poly(A) tail to a messenger RNA. The poly(A) tail could consist of multiple adenosine monophosphates which could be a stretch of RNA that has only adenine bases. In eukaryotes, polyadenylation could be part of the process that produces mature messenger RNA (mRNA) for translation (Wahle et al., The EMBO Journal. 12 (2): 585-594. (1993)). The sequence elements for polyadenylation include the polyadenylation signal (Poly(A) Signal) and the polyadenylation site (Poly(A) Site). In mRNA or cDNA the added stretch of polyadenosine monophosphate can be the polyadenylation tail (Poly(A) tail). The typical sequence for poly(A) signal could be, but not limited to, AATAAA, but other similar sequence can also be used as poly(A) signal by polyadenylation complex (Ohler et al., Bioinformatics, 29(13): i108-i116 (2013)). Many protein-coding genes could have more than one polyadenylation site, so a gene can code for several mRNAs that differ in their 3' end (Lutz et al., *Nucleic Acids Research.* 33 (1): 201-12. (2005)).

The term "functional fluorescent protein" as used herein refers to a protein capable of absorption of a higher energy photon (excitation) and emission of a lower energy photon from a molecule or more than one molecule (fluorophore) inside the protein from prior absorption. The fluorescence generated by said protein could be detected by an optical detector.

The term "fluorescence expression" as used herein refers to fluorescence generated through the fluorescent protein could be detectable by an optical detector.

The term "dual fluorescent reporter" as used herein refers to there being two fluorescent proteins with different wavelengths within the same cell. In some aspects, the one could turn on. In other aspects both are off or on.

The term "a splice trapping acceptor site" as used herein refers to a nucleotide sequence forces splicing from any exon upstream to itself during transcription. Typically, a splice trapping acceptor site can be inserted into an intron directly downstream of an exon which was intended to be trapped through RNA splice. The resulting sequence could get transcribed as a hybrid message with the initial portion of the exon and a hybrid protein can be produced. A splice trapping acceptor site could comprise of, but not limited to, natural occurring splice acceptor, man-made splice acceptor, or acceptor that generated by computer assisted programs.

The term "genetic modification" as used herein refers to at least one nucleotide change including insertion and deletion of an endogenous nucleotide sequence.

The term "homologous recombination" as used herein refers to a type of genetic recombination in which nucleotide sequences are exchanged between two similar or identical molecules of DNA.

The term "gene targeting" as used herein refers to a genetic technique that uses homologous recombination to change an endogenous gene. Specifically, recombination between homologous regions contained within the introduced DNA fragment and the native chromosome will lead to the replacement of a portion of the chromosome with the engineered DNA.

The term "targeting vector" as used herein shall refers to a DNA sequence that includes two homology arms, such as 5' and 3' homology arms, an antibiotic selectable marker gene and other sequences between the two homology arms. Targeting vector has the same meaning as targeting construct.

The term "5' and 3' homology arms" as used herein refers to DNA sequences in a targeting vector that are identical, or have significant homology to the endogenous DNA sequences where a homologous recombination will take place. The homology can be in a range from 80%-100%.

The term "an antibiotic selectable marker gene inside 5' and 3' homology arms" as used herein refers to an antibiotic selectable marker gene could be inserted in many locations inside the targeting vector. It could be inserted, but not limited to, sequences next to 5' GFP, 3' GFP, recombination sites, Poly(A) signal, promoter, target sequence. The antibiotic selectable marker gene could be often flanked by two recombination sites, such as frt site, from a different recombination system, such as FLP recombination system. When the targeting or during the targeting process, the antibiotic selectable marker gene can be removed by introducing the second recombinase. In general, the insertion of antibiotic selectable marker gene should avoid, but not limited to, functional exon, functional promoter, functional splice sites, functional recombination site, functional target sequence, functional Poly(A) sequence, functional 5' and 3' DNA sequences coding for GFP, 5' and 3' homology arms. Typically, the insertion of the selectable marker gene would not interfere, or substantially not interfere, the functional part of the gene and other introduced sequences inside targeting vector.

The term "splicesome" as used herein refers to a complex molecular machine found primarily within the splicing speckles of the cell nucleus of eukaryotic cells. The spliceosome can be assembled from snRNAs and protein complexes. The spliceosome removes introns from a transcribed pre-mRNA, a type of primary transcript. This process is generally referred to as splicing.

The term "targeted germline mouse" as used herein shall mean a mouse carries the targeted modification in its germline. This targeted modification can be passed down to next generation.

The term "reporter" as used herein shall mean a gene which codes for a protein which can be easily identified and measured within an organism. The reporter can be used as a selectable marker. The reporter can be often used as an indication of whether a certain gene has been taken up by or expressed in the cell or organism population.

In FIG. 1 there is shown the basic concept of dividing a fluorescent protein, e.g. green fluorescent protein, into at least two portions by a heterologous sequence with a splice donor and an acceptor sequences. A fluorescent protein can be divided into two portions, e.g., a 5' portion and a 3' portion. The 5' portion in FIG. 1 was linked to a promoter sequence and the 3' portion was linked to a poly (A) sequence. One embodiment described herein can be that a fluorescent protein, such as green fluorescent protein (GFP) can be utilized as it is often used as a reporter. Once expressed, the reporter fluorescent protein can be detected by observation under fluorescent microscope or other fluorescence detection apparatus. In order to observe where and when the gene was deleted by a recombinase, the reporter needs to stay non-active, or substantially non-active, for example, for GFP, no-green or substantially no-green before the action of the recombinase. After the action of the recombinase, and removal of the targeted gene, the reporter needs to be active or substantially active, for example, green or substantially green in the targeted cells to indicate where and when the targeted gene was deleted. In some embodiments, the endogenous promoter from a target gene is not used, as very often the target gene promoter may not be strong enough to generate detectable of fluorescence and there is large variation of promoter strength among natural genes.

Heretofore, in the field of animal model creation, GFP was mostly used as a single linear chain of amino acid which was coded by a single stretch of polynucleotides.

In accordance with the invention, a stretch of polynucleotide sequence is inserted into a pre-determined coding region of a reporter, for example, GFP, dividing the reporter (e.g., GFP) into at least two parts (or two portions), e.g., an N-terminus part and a C-terminus part. In one embodiment, at least the N-terminus part (first portion) will not be able to generate a reporter signal, e.g., green fluorescence. In some embodiments, neither part nor portion can generate a reporter signal, e.g., green fluorescence. The inserted stretch sequence may contain intron splicing elements which can be spliced out by RNA splicesome.

In order to keep the target gene expression intact or substantially intact before the action of recombinase, in some embodiments the target gene and/or the region that can be essential to the function of the gene and can be flanked by two recombination sites, e.g., a first and second recombination sites. In some embodiments the first and second recombinant sites can be at positions where the desired deleted sequence starts and ends, respectively. While not wanting to be limited by theory, it is believed that keeping any genetic modification to a minimum can provide the benefit of the target gene expression not being disturbed during the insertion of these two recombination sites and other genetic modifications. In some embodiments, the first and second loxP sites could also carry other sequences such as extra modification sequences, e.g., restriction enzyme sites and other useful sequences. In some embodiments, the recombination sites can be identical or different.

In an embodiment, the sequence encoding the reporter, e.g., fluorescent protein, can be placed in the opposite direction of transcription of the target gene. The N-terminus part or first portion of said reporter (e.g., fluorescent protein) together with a promoter can be inserted at the 3' end of the target gene, behind a polyA signal of the target gene, with a first recombination site. In some embodiments, the first recombination site can be a loxP site or Rox. In some embodiments, the C-terminus part of the reporter, e.g., fluorescent protein, with a second recombination site, such as another loxP and or Rox site, can be inserted in an intron of the target gene. The placement of the second recombination site can be determined by how long the target sequence needed to be deleted such that, but not limited to, the target sequence could contain functional sequence. When the target gene is deleted, it may lead to change of phenotype of the organism, more specifically, an animal.

Upon expression of the recombinase, the target gene between the two recombination sites can be deleted, which can bring the sequences encoding for N-terminus and C-terminus together with a much shorter intron. Since the N-terminus has its own promoter, this promoter may drive expression of RNA which includes the coding regions for the N-terminus, intron, and C-terminus of the reporter (e.g., fluorescent protein). RNA splicesome can splice and bring the RNA sequence for the N-terminus and C-terminus together to create an mRNA. This mRNA will code for a complete reporter, such as fluorescent protein, and turn on the reporter signal (e.g., fluorescence) upon excitation by certain wavelength.

In one embodiment, the C-terminus part of the reporter (e.g., fluorescent protein) could be kept as small as possible as far as the sequence encoding for N-terminus reporter protein (e.g., fluorescent protein) could not create a functional reporter (e.g., fluorescent protein), in order to minimize the impact of the insertion of a foreign sequence.

In another embodiment, said promoter can be selected independently from the target gene promoter, which offers flexibility and diversity. Researchers can select promoters among, but not limited to, promoters that are ubiquitous, cell specific, and inducible.

In some embodiments, a recombinant nucleic acid construct is described, wherein the construct comprises, in order from upstream (5' end) to downstream (3' end) and/or operably linked to one another, a promoter sequence, a nucleic acid sequence encoding a gene product of a first portion including an N-terminus of reporter, (e.g., a fluorescent protein, beta-galactosidase, luciferase, and chloramphenicol acetyltransferase.), wherein the protein product of the first portion is insufficient to provide reporter expression (e.g., fluorescent expression); a splice donor site; a heterologous nucleic acid sequence; a splice acceptor site; a nucleic acid sequence encoding a protein gene product of second portion including a C-terminus of the reporter (e.g., fluorescent protein); and a poly(A) signal sequence. In some embodiments, the promoter can be pCAG. In some embodiments, the promoter sequence is of sufficient strength to initiate the expression of its downstream sequences in the cell of interest. In some embodiments, the promoter sequence is of sufficient strength to initiate the expression of its downstream sequences in most cells. In some embodiments, fluorescence cannot be generated unless the first and second portions of the sequences are connected by a heterologous sequence containing splice donor and acceptor. Once they are connected, RNA splicesome can splice the heterologous sequence containing splice donor and acceptor and bring the first and second portions together to form a complete reporter sequence (e.g., fluorescent protein sequence) which can be translated into a functional reporter (e.g., a functional fluorescent protein).

Figure 2:
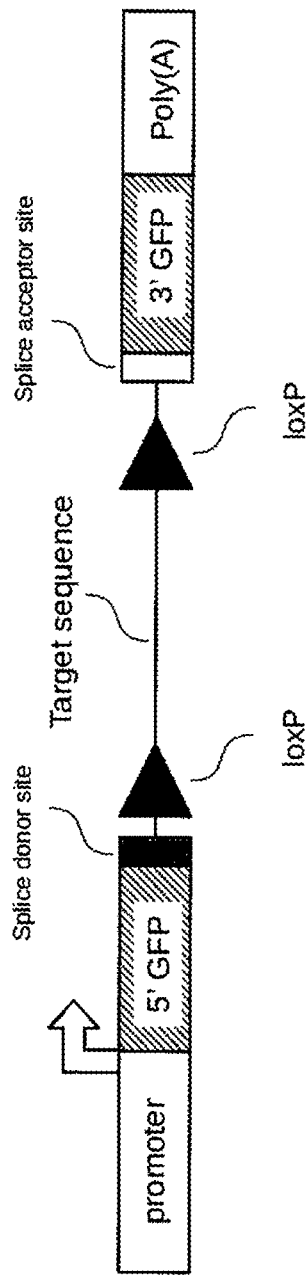
FIG. 2 shows a schematic view of an embodiment of a conditional construct described herein.

As shown in FIG. 2, a further developed construct of FIG. 1 is provided. The heterologous sequence is comprised of a target sequence flanked by two recombination sites. The target sequence could be a sequence of interest which genetic modifications may take place. In some embodiments, the construct can further comprise a 5'-homology arm and a 3' homology arm, two recombination sites, and sequences of interest for genetic manipulation to form a targeting vector.

Figure 3:
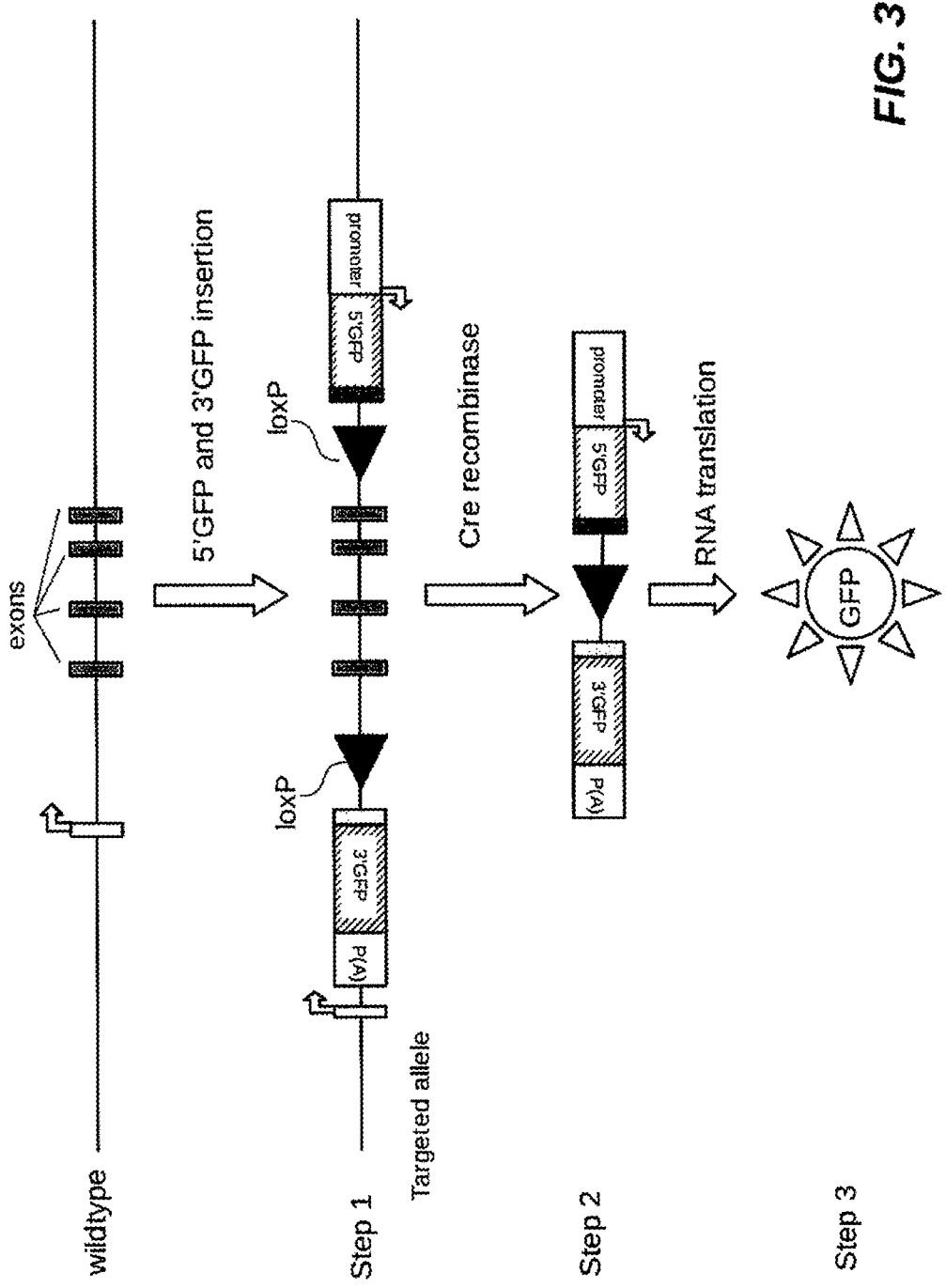
FIG. 3 shows a schematic view of a method described herein.

As shown in FIG. 3, in some embodiments, a method for turning on fluorescence is described, the method can comprise exposing the further developed construct of FIG. 2 to a recombinase, e.g. Cre recombinase. In some embodiments, the method can comprise (Step 1), constructing a DNA construct comprising sequences described in FIG. 2, wherein the target gene is a part of an endogenous gene. The construct can further comprise a 5' and 3' homology arms for a target insertion. DNA constructs in accordance with the invention can further comprise an antibiotic select marker gene for providing selection by an appropriate drug. In some embodiments, the method can comprise (Step 2), (a) introducing the DNA construct into a cell, e.g. a mouse embryonic stem cell; (b) screening for a targeted clone; and/or (c) generating a mouse derived from the targeted clone, e.g., a conditional mouse. In some embodiments, the method can comprise (Step 3), mating said conditional mouse with a recombinase containing mouse The recombinase could remove the target sequence, e.g., the sequence between the recombination sites which could include the targeted gene for deletion and bring the 5' and 3' sequences coding for a fluorescent protein operably together, e.g., by splicing the 5' and 3' fluorescent portions together. The promoter linked to the 5' portion of the sequence could drive the expression of RNA containing the 5' and 3' sequences, which can be spliced by a RNA splicesome to generate a full RNA which can be translated into a full fluorescent protein. FIG. 3 further shows that the 5' and 3' portion sequences coding for a fluorescent protein can be inserted in the opposite direction of a target gene. In some embodiments, a method of introducing divided polynucleotide sequences coding for a fluorescent protein into a mouse embryonic stem (ES) cell and selection of the targeted clone is described. In another embodiment, the method further includes generating targeted germline mouse (conditional) using the ES cell of; and mating said mouse with a recombinase containing mouse. The recombinase can recognize the two recombination sites in a second generation mouse and can delete the sequence between these two sites including the sequences of interest for genetic manipulation. When the sequence of interest is deleted, the first and second portions of sequences encoding for a fluorescent protein may be spliced together by RNA splicesome to form a sequence encoding for a full fluorescent protein. Upon the translation, fluorescence can be generated by exposing the cell to light of certain wavelength to indicate the deleting event by a recombinase in a cell. The fluorescence can be detected by systems receptive or able to read the emissive wavelengths generated by the fluorescent protein.

In some embodiments, a plasmid is described, the plasmid can comprise the nucleic acid constructs described above. In some embodiments, a cell is described, the genome can comprise the nucleic acid constructs described above. In some embodiments, a kit is described, the kit can comprise components of the nucleic acid constructs as described above.

In some embodiments, a recombinase is described, the recombinase can be capable of recognizing and/or reacting to the above described recombination sites, e.g., loxP. In some embodiments, the recombinase can be Cre recombinase (SEQ ID NO: 19) or a codon optimized iCre.

In some embodiments the reporter protein can be a fluorescent protein. In some embodiments, the fluorescent protein can be selection of green fluorescent protein (GFP), enhanced green fluorescent protein (EGFP) (SEQ ID NO: 2), or a red fluorescent protein (DsRed) (SEQ ID NO: 3). In some embodiments, the reporter protein can be beta-gal, luciferase, and chloramphenicol acetyltransferase.

In some embodiments, the construct can comprise a target sequence. FIG. 4 shows an exon trapping sequence can be inserted into the construct as described in FIG. 3 to prevent 5' portion to splice to 3' portion of a fluorescent protein before exposing to a recombinase. The exon trapping sequence could be inserted within the two recombination sites. The term recombination site or sites refers to the nucleic acid sequence recognized by or binding with the recombinase to enable excision of a sequence by action of the recombinase. Before exposing a recombinase, 5' portion could splice into the exon trapping sequence instead of the 3' portion sequence. After exposing to a recombinase, sequence including the exon trapping and target sequence could be removed, so the 5' portion was brought together with 3' portion to turn on a full expression of a fluorescence protein as described in FIG. 3.

In some embodiments, the target sequence can comprise a sequence capable of trapping exon. In some embodiments, the sequence capable contains EN2 exon trapping sequence (SEQ ID NO: 7).

In some embodiments, the first portion of the sequence encoding the N-terminus end of a fluorescent protein has an ATG initiation site. In some embodiments, the heterologous sequence can comprise sequences of endogenous sequence from the organism where the gene modification takes place. In some embodiments, the heterologous sequence can comprise at least one recombination site. In some embodiments, the heterologous sequence can comprise at least two recombination sites.

Figure 5:
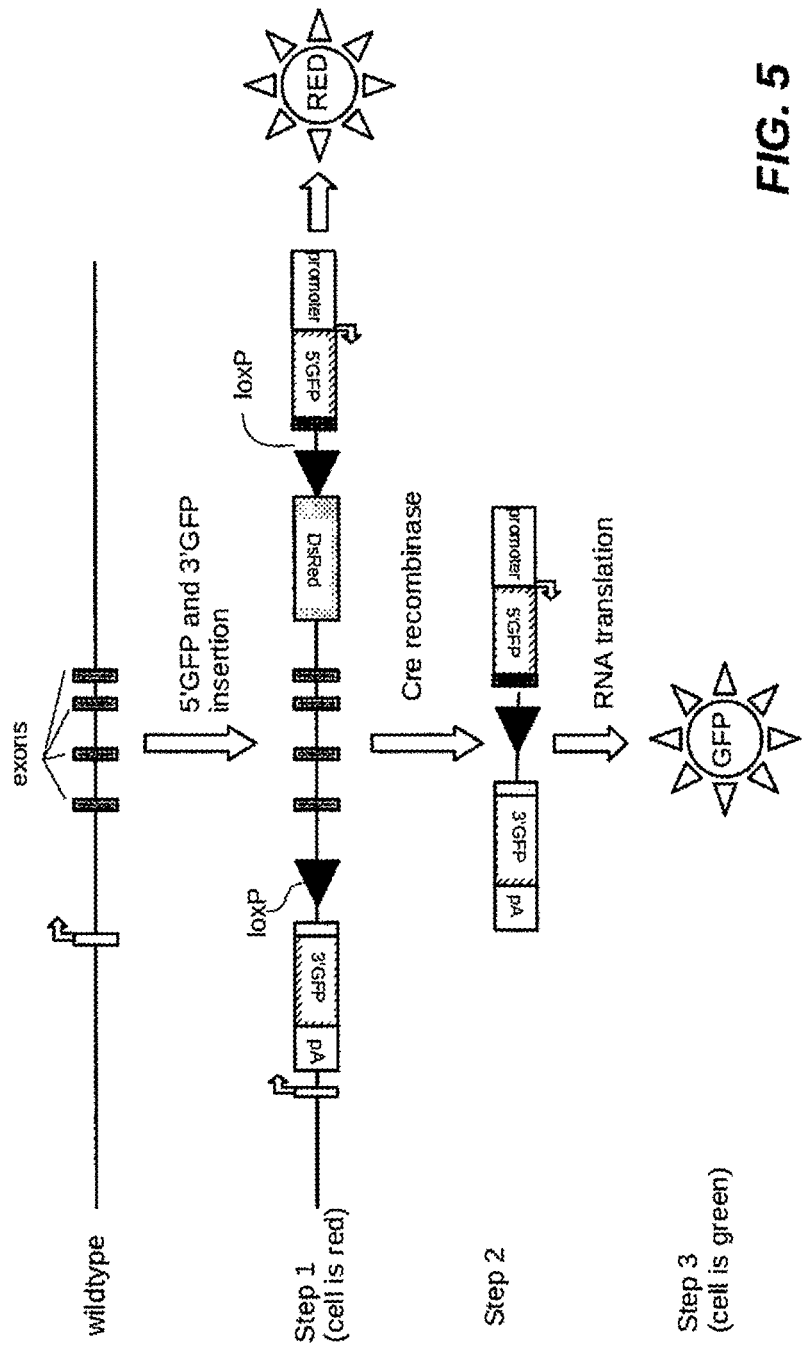
FIG. 5 shows a schematic diagram of another embodiment described herein.

In some embodiments, as shown in FIG. 5, a method described herein utilizing dual fluorescent proteins, e.g. red and green, to provide color switching before and after exposing to a recombinase in a cell. In this embodiments, before exposing to a recombinase, the cell and/or animal has red fluorescent protein encoding, expressing an observed red fluorescence. After exposing to a recombinase, the sequence coding for the red fluorescent protein was removed and a green fluorescent protein can be expressed. This can provide a different way to demonstrate deletion of the targeted sequence Promoters and Their Particular Usage In some embodiments, the construct can comprise a promoter. Typically, a promoter can be a region of DNA that initiates transcription of a gene. In general, the promoter can be located near the transcription start sites of genes, on the same strand and upstream on the DNA (towards the 5' region of the sense strand) in eukaryotic cells (Gagniuc et al., *BMC Genomics*. 13 (1): 512. (2012)). In one embodiment, the promoter can be a naturally occurring and/or native DNA sequence, which is not manmade. In another embodiment, the promoter can be manmade and/or derived from native. In further embodiment, the promoter can be combinations of manmade and non-manmade DNA sequences. In some embodiments, the promoters can be composite promoters which combine promoter elements of different origins or were generated by assembling a distal enhancer with a promoter of the same origin or different origin. In a broad sense, a eukaryotic promoter can be any DNA sequence that could be capable of initiating transcription of a gene, in particular, a fluorescent gene or part of fluorescent gene in eukaryotic cells.

In one embodiment, a eukaryotic promoter can contain regulatory sequences typically bound by proteins called transcription factors that can be involved in the formation of the transcriptional complex. Some promoters that could be targeted by multiple transcription factors might achieve hyperactive or hypoactive state, leading to increased or decreased transcriptional activity (Liefke at el., *Genome Med.* 7 (1): 66. (June 2015).

In one embodiment, promoters can be selected based on particular cells of interest. If there is an indication of a gene in this particular cells involved in a particular biological process suggested by other experiments, a promoter known to drive gene expression in these cell can be selected. In some embodiments, the gene of interest can be flanked by two recombination sites. In some embodiments, the gene of interest can be flanked by two loxP sites and the GFP cassettes containing 5-terminus and 3'-terminus can be inserted in the opposite direction of the gene. In some embodiments, suitable mutant loxP sited can be used. In some embodiments, once the gene was deleted by Cre recombinase, this promoter could drive GFP expression. Subsequent of the gene deletion, the GFP, previously split in the original construct, could be turned on in the expected cells, indicating the successful removal or deletion of the intervening target gene/desire sequence to be removed. In some embodiments, the experiment could go un-expected, such that Cre recombinase expressed at different cell types or different timing than one has planned in the target cells. In some embodiments, the Cre recombinase may have been expressed, but could not delete the target cell as the gene location could be protected by chromatin structures or other chromosomal protection mechanisms. In some embodiments, Cre deletion may have taken place in un-wanted locations. Typically, there may be genetic and epi-genetic variations among animals. Locations where the deletion took place and timing can be quite different among each other although all the animals have the same genotypes. Practically, it can be difficult, if not possible, to predict the express pattern a promoter creates.

Ideally, in order to track the deletion created by a recombinase, such as Cre recombinase, the 5'-GFP can be expressed in the cells where deletion possibly could take place. Typically, since the event of deletion could not be predicted, one of the safest ways could be trying to express 5'-GFP in every cell to anticipate the deletion. Since 5'-GFP by itself could not generate functional fluorescent protein, in the event of no deletion, the cell will not turn fluorescence. Only when a deletion occurred, recombination by the recombinase could bring 5' and 3' GFP sequence together to turn on fluorescence.

In some embodiments, promoters that drive gene expression in every cell may practically not exist. But there are promoters could drive gene expression in majority of cells. They were often called ubiquitous promoters. Ubiquitous Promoters are the promoters drive strongly expression in a wide range of cells, tissues and cell cycles (Schorpp et al., *Nucleic Acids Res* 24 (9): 1787-1788. (1996)). One of them, but not limited to, pCAG promoter is capable to drive GFP expression in many tissues (SEQ. ID NO:1).

pCAG promoter was constructed in the lab of Dr Jun-ichi Miyazaki (Miyazaki et al., *Gene*. 79 (2): 269-77. (1989); and Niwa et al., *Gene*. 108 (2): 193-9. (1991) from the following sequences: 1) the cytomegalovirus (CMV) early enhancer element, 2) the promoter, the first exon and the first intron of chicken beta-actin gene, 3) the splice acceptor of the rabbit beta-globin gene.

The pCAG promoter can be a strong synthetic promoter frequently used to drive high levels of gene expression in many mammalian expression vectors (Okabe et al., FEBS Lett. 5; 407(3):313-9. (1997); and Alexopoulou et al., BMC Cell Biology 9: 2. (2008).

In one embodiment, in a target cell before the introduction of the Cre recombinase, pCAG may only drive expression of 5' part of the GFP as the 3' GFP may be located farther away from the 5'GFP sequence. There can be many potential exon trapping sequences inside the target sequence. The transcribed 5'GFP may not be able to reach to the 3'GFP before it could be intercepted. Without available 3'GFP, the 5' GFP may not be functional, affecting a fluorescence. As a result, no fluorescence may be detected. In some embodiments, the transcripted 5'GFP could be constantly available in the target cell. Only upon the expression of cre recombinase, 5'GFP and 3'GFP may be spliced together to product a functional GFP which can turn fluorescence upon proper excitation to indicate where and when a deletion had taken place.

In further embodiment, they are, but not limited to, many ubiquitous promoter including: beta-Actin promoter, EF1 (elongation factor-1 alpha) promoter, EGR1 (early growth response 1) promoter, elF4A1 promoter, FerH (human ferritin heavy chain) promoter, FerL (human ferritin light chain) promoter, GAPDH (glyceraldehyde-3-phosphate dehydrogenase) promoter, GPR78 (glucose-regulated protein 78) promoter, GPR94 (glucose-regulated protein 94) promoter, HSP70 (heat shock protein 70) promoter, beta-Kin promoter, PGK-1 (phosphoglycerate kinase 1) promoter, Ubiquitin B promoter, beta Act/RU5' promoter, CMV (cytomegalovirus) promoter. The MC1 (polyoma enhancer/herpes simplex virus thymidine kinase) promoter. A non-limiting list of suitable promoters includes CAGGS, hCMV, PGK, FABP, Lck, CamKII, CD19, Keratin, Albumin, aP2, Insulin, MCK, MyHC, WAP, Col2A, Mx, tet, ubiquitin C, and Trex promoter.

The ubiquitous promoter could include other promoter selected from polymerases I, II and III dependent promoters, preferably is a polymerase II or III dependent promoter including, a snRNA promoter such as U6, a RNAse P RNA promoter such as Hi, a tRNA promoter, a 7SL RNA promoter, a 5 S rRNA promoter, etc.

In some embodiments the promoter can be three other types of promoters, but not limited to, can be used according to the intended type of control of gene expression. In some embodiments, these other promoters can be:

1. Constitutive promoters. These promoters direct expression in virtually all tissues and are largely, if not entirely, independent of environmental and developmental factors. As their expression is normally not conditioned by endogenous factors, constitutive promoters are usually active across species and even across kingdoms.
2. Tissue-specific or development-stage-specific promoters. These direct the expression of a gene in specific tissue(s) or at certain stages of development. Tissue specific promoters could include FABP (Saam & Gordon, J. Biol. Chem., 274:38071-38082 (1999)), Lck (Orban et al., Proc. Natl. Acad. Sci. USA, 89:6861-5 (1992)), CamKII (Tsien et al., Cell 87: 1317-1326 (1996)), CD19 (Rickert et al., Nucleic Acids Res. 25:1317-1318 (1997)); Keratin (Li et al., Development, 128:675-88 (201)), Albumin (Postic & Magnuson, Genesis, 26:149-150 (2000)), aP2 (Barlow et al., Nucleic Acids Res., 25 (1997)), Insulin (Ray et al., Int. J. Pancreatol. 25:157-63 (1999)), MCK (Bruning et al., Molecular Cell 2:559-569 (1998)), MyHC (Agak et al., J. Clin. Invest., 100:169-179 (1997), WAP (Utomo et al., Nat. Biotechnol. 17:1091-1096 (1999)), Col2A (Ovchinnikov et al., Genesis, 26:145-146 (2000)); examples of inducible promoter sites are Mx (Kuhn et al. Science, 269: 1427-1429 (1995)), tet (Urlinger et al., Proc. Natl. Acad. Sci. USA, 97:7963-8 (2000)), Trex (Feng and Erikson, Human Gene Therapy, 10:419-27). Above-mentioned promoters can turn into inducible promoters by combining them with an operator sequence including, but not limited to, tet, Gal4, lac, etc.
3. Inducible promoters. Their performance may not condition to endogenous factors but to environmental conditions and external stimuli that can be artificially controlled. Within this group, there are promoters modulated by abiotic factors such as light, oxygen levels, heat, cold and wounding. Since some of these factors are difficult to control outside an experimental setting, promoters that respond to chemical compounds, not found naturally in the organism of interest, are of interest. Along those lines, promoters that respond to antibiotics, copper, alcohol, steroids, and herbicides, among other compounds, have been adapted and refined to allow the induction of gene activity at will and independently of other biotic or abiotic factors.
4. Synthetic promoters. Promoters made by bringing together the primary elements of a promoter region from diverse origins.

Apart from the promoter types mentioned above, there are regulatory expression systems based on transactivating proteins. These systems regulate the expression of genes of interest irrespective of their physical position to the target genes. In fact, several chemical-inducible promoters incorporate transactivating proteins and constitutive promoters as part of the regulatory system. Transactivating proteins constitute a whole realm of molecules in the field of gene regulation (Beaulieu et al., *Br. J. Pharmacol.* 172 (1): 1-23. (2015).

Reporter Proteins and their Usage

In one embodiment, the reporter protein is a fluorescent protein. The fluorescent proteins can be, but are not limited to, capable of absorption a higher energy photon (excitation) and emission of a lower energy photon from a molecule (fluorophore) inside the protein from prior absorption.

In other embodiment, the fluorophore can be more than one molecule.

In some other embodiment, but are not limited to, protein containing tryptophan, tyrosine, or phenylalanine residue within its sequence can be used utilized as fluorescent protein.

In some other embodiment, but are not limited to, fluorescent protein can be protein capable of binding to non-proteinaceous chromophores to become fluorescence.

In one embodiment, the fluorescent protein can be also called an optical marker. If it is used inside a cell, it may be called an optical cell marker.

The green fluorescent protein (GFP) can be a protein composed of 238 amino acid residues (26.9 kDa) that exhibits bright green fluorescence when exposed to light in the blue to ultraviolet range (Prendergast et al, Biochemistry. 17 (17): 3448-53. (1978); and Tsien et al., Annual Review of Biochemistry. 67: 509-44. (1998)). Although many other marine organisms have similar green fluorescent proteins, GFP traditionally refers to the protein first isolated from the jellyfish *Aequorea victoria*. The GFP from *A. Victoria* has a major excitation peak at a wavelength of 395 nm and a minor one at 475 nm. Its emission peak is at 509 nm, which is in the lower green portion of the visible spectrum. The fluorescence quantum yield (QY) of GFP is 0.79. The GFP from the sea pansy (*Renilla reniformis*) has a single major excitation peak at 498 nm. GFP makes for an excellent tool in many forms of biology due to its ability to form internal chromophore without requiring any accessory cofactors, gene products, or enzymes/substrates other than molecular oxygen.

Another use of GFP can be to express the protein in small sets of specific cells. This allows researchers to optically detect specific types of cells in vitro (in a dish), or even in vivo (in the living organism) (Chudakov et al., *Biotechnology*. 23 (12): 605-13. (2005)).

Due to the potential for widespread usage and the evolving needs of researchers, many different mutants of GFP have been engineered (Shaner et al., *Nature Methods*. 2 (12): 905-9 (2005); and Wilhelmsson and Tor, *Fluorescent Analogs of Biomolecular Building Blocks: Design and Applications*. New Jersey: Wiley. ISBN 978-1-118-17586-6. (2016)).

The first major improvement was a single point mutation (S65T) reported in 1995 in by Roger Tsien (Heim et al., *Nature*. 373 (6516): 663-4. (1995)). This mutation dramatically improved the spectral characteristics of GFP, resulting in increased fluorescence, photostability. A 37° C. folding efficiency (F64L) point mutant to this scaffold, yielding enhanced GFP (EGFP), was discovered in 1995 (U.S. Pat. No. 6,172,188, Thastrup et al.; and Cormack et al., *Gene*. 173 (1 *Spec No*): 33-38, (1996).). Superfolder GFP, a series of mutations that allow GFP to rapidly fold and mature even when fused to poorly folding peptides, was reported in 2006 (Pédelacq et al., *Nature Biotechnology*. 24 (1): 79-88. (January 2006)).

Besides GFP, there are other fluorescent proteins can also report the genetic modification in the cells. They can be, but are not limited to, blue/UV fluorescent proteins, cyan fluorescent proteins, green fluorescent proteins, yellow fluorescent proteins, orange fluorescent proteins, red fluorescent proteins, far-red fluorescent proteins, Near-IR fluorescent proteins, Long strokes shift fluorescent proteins, Photoactivable fluorescent proteins, Photoconvertible fluorescent proteins, Photoswitchable fluorescent proteins.

In some embodiments, fluorescent proteins could be interchangeable and have been used as reporters. For example, but not limited to, a GFP or EGFP can be replaced by YFP, or Cerulean, or mTFP1 as far as it could serve as an optical reporter. In other embodiments, if two or more fluorescent proteins are required for a particular experiment, a careful planning may be needed for the compatibility of the color they generated. Spectral crosstalk and inter-variant interactions between fluorescent proteins should be carefully examined for multi-color imaging. In one embodiment, the coding sequence could be changed, but it still coded the same amino acid.

In some embodiments, an interaction among multiple fluorescent proteins could cause changes in fluorescence (or Förster) resonance energy transfer (FRET) to report on biochemical processes in living cells.

In some embodiments, blue/UV fluorescent proteins can be, but are not limited to, Y66H, Y66F, Y66W, EBFP, mCFP, ECFP, Azurite (Marco et al., *Nature Biotechnology* 24, 1569-1571 (2006)), GFPuv (wang et al., Hum Vaccin Immunother 9(7): 1558-1564. (2013), EBFP2 (Wu et al., Front Microbiol. 6: 607. (2015)), Cerulean (Wu et al., Front Microbiol. 6: 607. (2015)), CyPet (Scott et al., Sci Rep; 5: 10270. (2015)), TagBFP (Wu et al., Front Microbiol. 6: 607. (2015)), mTagBFP2 (Subach et al, PLoS One. 6(12):e28674. (2011)). EBFP2 (Ai et al., Biochemistry 46: 5904-5910. (2007)), mKalamal (Ai et al., Biochemistry 46: 5904-5910. (2007)), Sirius (Tomosugi, et al., Nat. Method. 5: p. 351-353. (2009)), Sapphire (Cubitt et al., Meth Cell Biol, 58: p. 19-30. (1999), T-Sapphire (Zapata-Hommer et al., BMC Biotechnol, 3(5). (2003)), TagBFP, TagCFP (Wu et al., Front Microbiol. 6: 607. (2015)), SBFP2 (Wu et al., Front Microbiol. 6: 607. (2015)), AmCyan1 (Clontech), mTFP1 (Rizzo et al., doi:10.1101/pdb.top63 Cold Spring Harb Protoc (2009)), S65A (Biochemistry 44: 1960-1970. (2005)).

In some embodiments, cyan fluorescent proteins can be, but are not limited to, ECFP (Wall et al., Biochem Mol Biol Educ. 43(1):52-9 (2015)), Cerulean (Rizzo et al., Nat Biotechnol. 22(4):p. 445-449 (2004)), SCFP3A (Kremers et al., G-J. et al., 45: p. 6570-6580. (2006)), mTurquoise (Goedhart et al., Nat. Meth. 7: p. 137-141. (2010), mTurquoise2 (Goedhart et al., Nat Commun. 20; 3:751. (2012), monomeric Midoriishi-Cyan, mTFP1 (Rizzo et al., doi:10.1101/pdb.top63 Cold Spring Harb Protoc (2009)).

In some embodiments, green fluorescent proteins can be, but are not limited to, EGFP, Emerald (Cubitt et al., Meth Cell Biol. 58: p. 19-30. (1999)), Superfolder GFP (Pedelacq et al., Nat. Biotech. 24: p. 79-88. (2006)), Monomeric Azami Green (MBL international), TagGFP2 (Evrogen), mUKG (Tsutsui et al., Nat. Methods. 5(8): p. 683-685. (2008)), mWasabi (Rizzo et al., doi:10.1101/pdb.top63 Cold Spring Harb Protoc (2009)), Clover (Lam et al., *Nature Methods* 9, 1005-1012. (2012)), mNeonGreen (Shaner et al., *Nature Methods*. 10: 407-409. (2013)), S65C, S65L, S65T (Pang et al., Plant Physiol. 112:893-900. (1996)), ZsGreen1 (Clontech), Dronpa-Green (Habuchi et al., PNAS. 102:9511-9516. (2005)), TagGFP (Evrogen), AcGFP1 (Clontech), CopGreen (Condon et al., Insect Mol Biol. 16(5):573-80. (2007)).

In some embodiments, yellow fluorescent proteins can be, but are not limited to, EYFP, Citrine (Griesbeck et al., Biol Chem. 276(31): p. 29188-94. (2001)), Venus (Nagai et al., Nat Biotechnol. 20(1): p. 87-90. (2002)), SYFP2 (Ledermann et al., Mol Plant Microbe Interact. 28(9):959-67. (2015)), TagYFP (Evrogen), Topaz (Yu et al., Genom Data. 5: 318-319. (2015)), mCitrine (Rizzo et al., doi:10.1101/pdb.top63 Cold Spring Harb Protoc (2009)), Ypet (Scott et al., Sci Rep; 5: 10270. (2015)), TurboYFP, PhiYFP (Condon et al., Insect Mol Biol. 16(5):573-80. (2007)), PhiYFP-m (Condon et al., Insect Mol Biol. 16(5):573-80. (2007)), ZsYellow1 (Richards et al., Cytometry. 1; 48(2):106-12. (2002)), mBanana (Zhou et al., Protein Pept Lett. 15(1):113-4. (2008)), Y66S (Biochemistry 44: 1960-1970. (2005)).

In some embodiments, orange fluorescent proteins can be, but are not limited to, Monomeric Kusabira-Orange (MBL international), mKOx (Tsutsui et al., Nat. Methods. 5(8): p. 683-685. (2008)), mKO2 (MBL international), mOrange (Shaner et al., Nat Biotechnol, 22(12):1567-72. (2004)), mOrange2 (Shaner et al., Nat. Meth. 5: p. 545-551 (2008)), and mKO (Sung et al., PLoS One. 20; 10(11):e0141585 (2015)).

In some embodiments, red fluorescent proteins can be, but not limited to, TurboRFP, dKeima-Red, mKeima-Red, mRaspberry, mCherry, mStrawberry, mTangerine, tdTomato, TagRFP (Scott et al., Sci Rep; 5: 10270. (2015)), TagRFPt (Scott et al., Sci Rep; 5: 10270. (2015)), mApple, mRuby (Scott et al., Sci Rep; 5: 10270. (2015)), mRuby2 (Scott et al., Sci Rep; 5: 10270. (2015)), DsRed (Yarbrough et al., Proc Natl Acad Sci USA. 16; 98(2):462-7. (2001)), DsRed-Express2 (Gottwein et al., J Virol. 85(17):8913-28. (2011)), DsRed monomer (Chou et al., Chin J Physiol. 28; 58(1):27-37. (2015)), DsRed2 (He et al., Cell Biosci. 5:67. (2015)), TurboRF602 (Khodosevich et al., Front Mol Neurosci. 2: 7 (2009)), AsRed2 (Hirrlinger et al., Mol Cell Neurosci. 30(3):291-303. (2005)), mRFP1 (Wallrabe et al., Cytometry A. 87(6):580-8. (2015)), J-Red (Condon et al., Insect Mol Biol. 16(5):573-80. (2007)), HcRed1 (Subach et al., Chem Biol. 20; 15(10):1116-24. (2008)), TurboRF635 (Evrogen), Katushka (Kinnear et al., PLoS One. 19; 10(6): e0130375. (2015)), and Katushka2 (Kinnear et al., PLoS One. 19; 10(6):e0130375. (2015)), mRaspberry (Wang et al., Proc Natl Acad Sci, 101(48):p. 16745-16749. (2004)), mCherry (Shaner et al., Nat Biotechnol, 22(12):1567-72. (2004)), mStrawberry (Shaner et al., Nat Biotechnol, 22(12): 1567-72. (2004)), mTangerine (Shaner et al., Nat Biotechnol, 22(12):1567-72. (2004)), tdTomato (Shaner et al., Nat Biotechnol, 22(12):1567-72. (2004)), TagRFP (Evrogen), TagRFP-T (Shaner et al., Nat. Meth. 5: p. 545-551. (2008)), mApple (Shaner et al., Nat. Meth. 5: p. 545-551. (2008)), mRuby (Kredel et al., PLOS One, 4: e4391. (2009)), mRuby2 (Lam et al., *Nature Methods*. 9, 1005-1012. (2012)).

In some embodiments, far-red fluorescent proteins can be, but not limited to, mPlum (Wang et al., Proc Natl Acad Sci. 101(48):p. 16745-16749. (2004)), HcRed-Tandem (Maynard-Smith et al., JBC 282, 24866-24872. (2007)), mKate (Guess et al., Skelet Muscle. 3: 19. (2013)), mKate2 (Tanida et al., PLoS One. October 23; 9(10):e110600. (2014)), mNeptune (Lin et al., Chem. Biol. 16: p. 1169-1179. (2009)), NirFP (Evrogen), E2-Crimson (Barbier et al., PLoS One. 3; 11(3):e0146827. (2016)).

In some embodiments, near infar-red fluorescent proteins can be, but not limited to, TagRFP657 (morozova, Biophys J. 21; 99(2):L13-5. (2010)), IFP1.4 (Yu et al., Nat Commun. 15; 5:3626 (2014)), iRFP (Agollah et al., J Cancer. 23; 5(9):774-83. (2014).

In some embodiments, Long Stokes Shift fluorescent Proteins can be, but are not limited to, mKeima Red (Yang et al., PLoS One. 20; 8(6):e64849. (2013)), LSS-mKate1 (Piatkevich et al., PNAS, 107: p. 5369-5374. (2010)), LSS-mKate2 (Piatkevich et al., PNAS, 107: p. 5369-5374. (2010)), mBeRFP (Yang et al., PLoS One. 20; 8(6):e64849. (2013)).

In some embodiments, photoactivatible fluorescent proteins can be, but are not limited to, PA-GFP (Patterson et al., Science. 297(5588): p. 1873-7. (2002)), PAmCherry1 (Subach et al., Nat. Meth. 6: p. 153-159. (2009)), PATagRFP (Subach et al., JACS 132: p. 6481-6491. (2010)).

In some embodiments, Photoconvertible fluorescent proteins can be, but are not limited to, Kaede (green) (MBL international), Kaede (red) (MBL international), KikGR1 (green) (MBL international), KikGR1 (green) (MBL international), KikGR1 (red) (MBL international), PS-CFP2 (Evrogen), mEos2 (green) (McKinney et al., Nat Meth. 6: p. 131-133. (2009)), mEos2 (red) (McKinney et al., Nat Meth. 6: p. 131-133. (2009)), mEos3.2 (green) (Zhang et al., Nat. Meth. 9: p. 727-729. (2012)), mEos3.2 (red) (Zhang et al., Nat. Meth. 9: p. 727-729. (2012)), PSmOrange (Subach et al., Nat. Meth. 8: p. 771-777. (2011)).

In some embodiments, photoactivatible fluorescent proteins PA-GFP, PAmCherry1, PATagRFP may remain silent, may only turn on when the protein was activated by certain wavelength lights.

In some embodiments, photoconvertible fluorescent proteins, such as Kaede (green), Kaede (red), KikGR1 (green), KikGR1 (green), KikGR1 (red), PS-CFP2, mEos2 (green), mEos2 (red), mEos3.2 (green), mEos3.2 (red), PSmOrange can turn from a green fluorescence to red fluorescence under radiation of certain wave-length. It provides the ability to track individual neuronal cell and cell movement. It can often be that tissue of interest has auto-fluorescence. It could be the same color as the reporter color. It may make it very difficult to distinguish fluorescence that was generated from the background (auto-fluorescence) or target deletion. To solve this background auto-fluorescent problem, photoconvertible fluorescent protein, such as Kaede, can be used. In a way that two photos of microscope excited two different wavelengths can be taken. For example the original color has a background of auto-fluorescence. The same sample can be treated by radiation of certain wave-length which causes the structure changes on the fluorescence protein. The fluorescent protein will change to different color, but the background may not. So only the signal going with the color change could be the signal where target gene was deleted. In some embodiments, two fluorescent proteins can be fused together as dual fluorescent protein.

In some embodiments, more than two fluorescent proteins can be fused together to form a multi-fluorescent protein.

In some embodiments, part of a fluorescent protein fused with a full fluorescent protein.

In some embodiments, part of a fluorescent protein fused with multi-fluorescent protein.

In some embodiments, there are newly developed fluorescent proteins. They are, but not limited to, UnaG (Kumagai et al., Cell. June 20; 153(7):1602-11. (2013)), eqFP611 (Kredel et al., PLoS One. 4(2):e4391. (2009)), KFP (Khrenova et al., Biophys J. 108(1):126-32. (2015)), EosFP (Shcherbakova et al., Annu Rev Biophys. 43:303-29. (2014)), IrisFP (Gayda et al., Biophys J. 103(12):2521-31. (2012)), smurfp, FMN-binding fluorescent proteins (FbFPs) (Drepper et al., Appl Environ Microbiol. September; 76(17): 5990-4. (2010)).

In some embodiments, any protein capable of being detected and measured in cells and organisms, such as beta-galactosidase, luciferase, and chloramphenicol acetyl-transferase and other suitable proteins can be used as reporter proteins.

Inventive Details of Splice Sites and Its Insertion into a Sequence Coding for Fluorescent Protein In some embodiments, the construct can comprise a reporter protein. In some embodiments, the reporter protein can be a fluorescent protein, further the fluorescent protein could be green fluorescent protein (GFP). Dividing the coding sequence of GFP by splice donor and acceptor sites from an intron into at least two parts, or more than two parts, could keep the GFP silent (no indicated or perceived fluorescence) in event there is no recombinase and deletion and active when there is a deletion (indicated or perceived fluorescence).

In one embodiment, the insertion can be determined by the coding sequences around the insertion site and the sequences of splice donor and acceptor sites.

In some embodiments, the construct comprises an intron. In some embodiments, the intron can comprise a donor site (5' end of the intron), a branch site (near the 3' end of the intron), a heterologous sequence and/or an acceptor site (3' end of the intron) that may be required for splicing. The intron can obtain from nature sources or fully man-made.

In one embodiment, splicesome recognize a consensus sequence A-G-[cut]-G-T-R-A-G-T from the sequences around the 5' end of an intron, wherein A-G is provide from the upstream exon and G-T-R-A-G-T is from the 5' end of the intron, which could be essential part of the splice donor site, wherein R represents a choice of A or G. (Iupac-Iub Comm. On Biochem. Nomencl. *Biochemistry.* 9: 4022-4027 (1970); and De Conti et al., Wiley Interdiscip Rev RNA, 4(1):49-60. (2013); and Lewis et al., book of "Molecular Biology of the Cell". 2012; and William et al, *Nature Reviews Genetics.* 7 (3): 211-21. (2006); and Ohshima et al, J. Mol. Biol., 195:247-259(1987)).

In another embodiment, splicesome recognize another consensus sequence Y-rich-N-C-A G-[cut]-G from the sequences around the 3' end of the intron, wherein Y-rich-N-C-A G comes from the 3' end of the intron, which could be essential part of the splice acceptor site. The G at the end of said consensus sequence is contributed from exon downstream of the intron, wherein Y represents a possibility of C or T. N represents a possibility of A, C, G, or T. (Iupac-Iub Comm. On Biochem. Nomencl. *Biochemistry.* 9: 4022-4027 (1970); and De Conti et al., Wiley Interdiscip Rev RNA, 4(1):49-60. (2013); and Lewis et al., book of "Molecular Biology of the Cell" 2012; and William et al, *Nature Reviews Genetics.* 7(3): 211-21. (2006); and Ohshima et al, J. Mol. Biol., 195:247-259(1987)).

In another embodiment, upstream (5'-ward) from the AG at 3' end of the intron could be a region high in pyrimidines (C and T), or polypyrimidine tract. Further upstream from the polypyrimidine tract is the branchpoint, which may include an adenine nucleotide involved in lariat formation with a consensus sequence Y-N-C-T-R-A-C (Clancy et al., *Nature Education.* 1 (1): 31. (2008); and Black et al., *Annual Review of Biochemistry.* 72 (1): 291-336. (June 2003)). The branchpoint could be 20-50 nucleotides upstream of splice acceptor site.

In one embodiment, many locations inside the nucleotide coding sequence for a fluorescent protein could be selected such that the end of the first part of a fluorescent protein coding sequence can be connected to a splice donor site of an intron and the beginning of the second part of a fluorescent protein coding sequence can be connected to a splice acceptor site of the intron.

In one embodiment, in order to divide the coding sequence of a fluorescent protein into two separate parts, sequences surrounding the potential insertion sites (donor and acceptor site) should be closely examined by satisfying the rules suggested by the consensus sequences described above. Only designs with sequences very closely resembling to the consensus sequences may start to be constructed and tested.

In another embodiment, any sequences can be utilized as splice donor and acceptor as far as they can be recognized and spliced correctly by RNA splicesome.

In another embodiment, intron sequences can be utilized according to the U2 and U12 categorization (Sharp et al., Cell. 91: 875-879. (1997)).

Introns suitable for use in embodiments herein could be prepared by several methods such as purification from a naturally occurring nucleic acid or de novo synthesis. The introns present in many naturally occurring eukaryotic genes have been identified and characterized (Mount et al., Nuc. Acids Res., 10:459 (1982)). Artificial introns comprising functional splice sites also have been described. (Winey et al., Mol. Cell Biol., 9:329 (1989); and Gatermann et al, Mol. Cell Biol., 9:1526 (1989)). Introns may be obtained from naturally occurring nucleic acids, for example, by digestion of a naturally occurring nucleic acid with a suitable restriction endonuclease, or by PCR cloning using primers complementary to sequences at the 5' and 3' ends of the intron. Alternatively, introns of defined sequence and length may be prepared synthetically using various methods in organic chemistry (Narang et al., Meth. Enzymol., 68:90 (1979); and Caruthers et al, Meth. Enzymol., 154:287 (1985); and Froehler et al, Nuc. Acids Res., 14:5399 (1986)).

In some embodiments, vectors contain the suitable sequences including a cell specific promoter, the sequences encoding for 5' and 3' of a fluorescent protein, intron with splicing sites, and a Poly(A) signal can be constructed and tested in vitro (in cells). If the design of the intron insertion leads to right splicing, fluorescence could be observed under a fluorescent microscope. If fluorescence could not be observed, the insertion of the intron may need to change to a different location inside the coding sequence of a fluorescent protein with further tests.

In some embodiments, following above description, intron can be inserted in many locations inside GFP, or other fluorescent proteins of researchers' choices. Further, coding fluorescent protein or reporter protein can be divided by a heterologous sequence with splice donor and acceptor sites with different ratios of N-terminus to C-terminus portions, for example, but not limited to; 10% front, 90% back; 20% to 80%; 30% to 70%; 40% to 60%; 50% to 50%; 60% to 40%, 70% to 30%, 80% to 20%, respectively. The coding sequence of a fluorescent protein can be also divided into a ratio that the sum of percentages can be added to 100%. Each front part can only connect to its own back part to facilitate fluorescence expression. Different ratio of dividing coding sequence of a fluorescent protein can be very useful in tracking cell development including neuron development and disease animal model creations.

In one embodiment, the size of intron may vary from as little as a few nucleotides to over hundreds of thousands nucleotide. It thus provides further flexibility for researchers to design their research such that many functional components can be built inside the intron.

In further embodiment, at least four distinct classes of introns have been identified in the nature (Alberts, Bruce (2008). *Molecular biology of the cell*. New York: Garland Science) and most of these introns can be used as entirely or partially to insert into the fluorescent proteins. The four classes could include, but not limited to; 1) Introns in nuclear protein-coding genes that are removed by spliceosomes (spliceosomal introns). 2) Introns in nuclear and archaeal transfer RNA genes that are removed by proteins (tRNA introns). 3) Self-splicing group I introns that are removed by RNA catalysis. 4) Self-splicing group II introns that are removed by RNA catalysis.

In further embodiment, there is a fully or partially man-made intron, which can be also used to insert into the fluorescent protein.

In other embodiment, there may have other ways than site specific recombination to cut out of a stretch of sequences and subsequently bring together N- and C-terminus of GFP to activate GFP expression. They can be, but are not limited to, Crispr, TALENs, Zinc finger, rare cutting restriction enzymes, genomic translocation, hot-spot related deletions, immunology VDJ recombination, immune-class switching, gene inversion, natural deletion, and other known in the art.

In further embodiment, a suitable intron can be retrieved from genomic data source such as, but not limited to, ensemble, UC Davis genome browser.

In one embodiment, bioinformatic analysis can be employed to help the design of the intron insertion (Reese et al., *J Comp Biol* 4(3), 311-23. (1997)).

Cre-loxP and Other Applicable Recombination Systems

With an intent to delete a target gene and subsequently turn on fluorescence, the target sequence could be flanked by two recombination sites through genetic engineering. In some embodiments, an expressing second fluorescent protein can be included in the target sequence, such that removal of the target sequence also removes the expression of the second fluorescent protein, e.g., changing the fluorescence from the second emitted fluorescence to the first or indicating fluorescent protein emission, e.g., red changing to green (GFP). Two parts of the coding sequences for a fluorescent protein can be linked to these two recombination sites, in a configuration that the coding sequence of 5' a fluorescent protein with a promoter could be connected to an intron donor site and 3' a fluorescent protein was connected to an intron accepting site. The 5' and 3' sequence coding a fluorescent protein could be inserted along with these two sites in a direction opposite to the target gene expression direction. Upon the recombinase expression, the sequences between these two recombination sites could be deleted or excised and this process will bring the 5' and 3' coding sequence together. The promoter which connected with 5'GFP could drive the expression of a functional fluorescent protein.

In one embodiment, there could be many recombinases can be used to remove sequences between recombination sites. Cre recombinase is one of the most frequently used ones.

The Cre protein is a site-specific DNA recombinase. It can catalyze the recombination of DNA between specific sites in a DNA molecule. These sites, known as loxP sequences, contain specific binding sites for Cre that surround a directional core sequence where recombination can occur.

When cells that have loxP sites in their genome expressing Cre, a recombination event can occur between the loxP sites. Cre recombinase proteins bind to the first and last 13 bp regions of a loxP site forming a dimer. This dimer then binds to a dimer on another lox site to form a tetramer. LoxP sites are directional and the two sites joined by the tetramer are parallel in orientation. The double stranded DNA is cut at both loxP sites by the Cre protein. The strands are then rejoined with DNA ligase in a quick and efficient process. The result of recombination depends on the orientation of the loxP sites. For two lox sites on the same chromosome arm, a direct repeat of loxP sites will cause a deletion event, while an inverted loxP sites will cause an inversion of the target DNA.

In one embodiment, other systems to delete or inverse sequences may include by way of nonlimiting example,
1. FLP/frt recombination system (Schlake et al., Biochemistry. 33 (43): 12746-12751. (1994) and Turan et al., J. Mol. Biol. 402 (1): 52-69. (2010)).
2. Dre/rox recombination system (Anastassiadis et al., Dis Model Mech. September-October; 2(9-10):508-15. (2009)), Vcre/VloxP recombination system (Suzuki et al., Nucleic Acids Res. 39(8): e49. (2011)).
3. Scre/SloxP recombination system (Suzuki et al., *Nucleic Acids Res.* 39(8): e49. (2011)).
4. Nigri/nox recombination system (Karimova et al., *Scientific Reports* 6, Article number: 30130 (2016)).
5. Panto/pox recombination system (Karimova et al., *Scientific Reports* 6, Article number: 30130 (2016)).
6. PhiC31/att recombination systems (Thomson et al., *BMC Biotechnology.* 10:17. (2010)). Typically, the site specific recombination could only occur within its own recombinase.
7. Sleepingbeauty transposas which deletes the DR sequences in the mirrored IR/DR sequences (Zayed et al., *Mol Ther.* 9(2):292-304. (2004).

In general, one particular recombinase may only works with its own particular recombination sites. It may be a rare event that cross talk occurs among different recombinase based systems.

In the FLP/frt system, FLP recombinase was discovered in yeast *Saccharomyces cerevisiae* (Schlake et al., Biochemistry. 33 (43): 12746-12751. (1994) and Turan et al., J. Mol. Biol. 402 (1): 52-69. (2010)). For every FLP-mediated recombination, a total of four FLP recombinases and two frt sequences could be required. Two of the four proteins bind to one FRT sequence because every frt has two 13-bp FLP-binding sites which are interrupted by an 8-bp spacer region. In this spacer DNA strand breakage takes place, producing 8-bp overhanging ends. After strand breakage, the overhanging ends of the two FRT fragments come together by complementary base pairing so that a mutant frt sequence is generated.

Another recombination system is Dre/rox recombination system, Dre recombinase was first described in the P1-like transducing bacteriophage D6 isolated from *Salmonella enteric*. The genes encoding Dre and Cre recombinases share 39% sequence similarity. Dre recombinase could catalyze site-specific DNA recombination by recognizing rox sites, whereas Cre recombinase could not be able to recognize rox sites, which are distinct from loxP sites. Similar to Cre recombinase, Dre could delete the sequence between two rox sites if they are facing the same direction.

VCre/VloxP recombination system may also be used. Vcre showed very weak similarity to Cre, sharing 29% identity to the Cre amino acid sequence. It recognizes the VloxP sites.

There are other systems that may be used to delete the sequence between two recognizable sites. They are, but are not limited to, KD, B2 B3, lambda, HK022, HP1, lambda gamma, ParA, Tn3, Gin, Bxb1, R4, and TP901-1.

Typically, site specific recombinase recognized its own recombination site. It was discovered that the recombinase can also recognize sequences similar to the wildtype recombinase site with only one or a few bases. These sites were also called mutant sites.

As for example, in Cre/lox system, many mutant loxP sites were created. A mutant recombination site is a nucleotide sequence that is similar but not identical to the minimal native loxP recombination site set forth in SEQ ID NO:4. While the mutant loxP recombination site can be functional. Unless otherwise noted, a mutant loxP recombination site retains the biological activity of the wild type loxP recombination site and comprises a functional recombination site that is recognized by a Cre recombinase and capable of a recombinase-mediate recombination reaction. Thus, a mutant loxP recombination site can comprise a deletion, addition, and/or substitution of one or more nucleotides in the 5' or 3' end of the minimal native loxP recombination site, in one or more internal sites in the minimal native loxP recombination site. Generally, modified recombination sites will have at least about 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the minimal native recombination site over its complete length or to any domain contained therein. The mutant loxP recombination site could therefore include 1, 2, 3, 4, 5, 8, 10, 12, 13, 14, 15, 16, 17, 18, 19, 20, 21, 22, 23, 24, 25, 28, 29 or greater nucleotide substitutions, additions, and/or deletions across the entire length of the minimal recombination site, or alternatively, in each of the various domains of the recombination site as outlined above.

In one embodiment, the mutant loxP sites may have different characters than that the wildtype (native) loxP site. Some could be not compatible with the wildtype loxP site and some could. Some could be substantially compatible. When a mutant loxp site recombines with a wildtype loxP site, they will create a new mutant loxP site. Some of the combinations are reversible, some are not. These mutant loxP sites can be used to flank the target gene and sequences between the sites which can be deleted by Cre recombinase. Upon the Cre reaction, combination of two identical mutant loxP could leave a single mutant site, which could have an identical sequence as parental mutant loxP site. Combination of two different mutant loxP could leave a single mutant loxP site, which has the sequence which is different than any of its parent (wildtype, or native).

In one embodiment, among the mutant loxP sites, they are, but not limited to, lox511, lox5171, lox2272, M2, M7, M11, lox71, lox66, loxN, loxP 5171, and other published and un-published, and under-develop mutant loxP sites. In some embodiments, the mutant loxP site can also be called heterospecific loxP site or modified loxP site. Its diversity could be often created by variation inside the 8-bp spacer sequence.

In other embodiment, many mutant recombination systems could have their own sets of wildtype (native) recombination sites and their mutant recombination sites. They worked in a very similar way as described above. Among them, but not limited to, they include F3, F5, FL-IL10A, Vlox2272, Slox2272, VloxM1, SloxM2, VloxM2, SloxM2, Vlox43R, Vlox43L, Slox1R, Slox1L, attR, attL, attP, attB, IR/DR sequences.

In one embodiment, proper usage and combinational usage of these recombination sites can be incorporated into the design of turning fluorescence on and off, off and on with many other different combinations and configurations.

Poly (A)

In some embodiments, the construct can comprise a poly (A) sequence. Typically, a Polyadenylation signal poly(A) could be required for proper expression of an eukaryotic protein. Polyadenylation adds a poly(A) tail to a messenger RNA. The poly(A) tail could consist of multiple adenosine monophosphates which constitute a stretch of RNA with only adenine bases. In eukaryotes, polyadenylation could be part of the process that produces mature messenger RNA (mRNA) for translation. It could form part of the larger process of gene expression.

The process of polyadenylation could begin as the transcription of a gene terminate. The 3'-most segment of the newly made pre-mRNA can be first cleaved off by a set of proteins (Proudfoot et al., Cell. 108(4): 501-12. (2002) and Guhaniyogi et al., Gene. 265(1-2): 11-23. G (2001)).

These proteins then synthesize the poly(A) tail at the RNA's 3' end. In some embodiments, these proteins add a poly(A) tail at one of several possible sites and produce more than one transcript from a single gene (alternative polyadenylation), similar to alternative splicing (Proudfoot et al., Cell. 108 (4): 501-12. (2002)).

The poly(A) tail can be important for the nuclear export, translation, and stability of mRNA. The tail is shortened over time, and, when it is short enough, the mRNA is enzymatically degraded (Guhaniyogi et al., Gene. 265(1-2): 11-23. (2001)). However, in a few cell types, mRNAs with short poly(A) tails are stored for later activation by re-polyadenylation in the cytosol (Richter, Joel D. Microbiology and Molecular Biology Reviews, 63(2): 446-56. (1999)).

In one embodiment, the poly (A) sequence could be linked to the end of the 3' fluorescent protein coding sequence after the termination sequence. The combined sequences including the 3' end of the coding sequence with a termination sequence and poly (A) sequence could be inserted into a specific location inside one of the intron of a target gene.

In one embodiment, in order to keep minimum impact on the endogenous sequence, it could be desirable to keep the poly (A) sequence as shorter as it could.

In some embodiments, the ploy (A) can be acquired by extension of 3' GFP coding sequence into a region where similar sequence can be functional as a signal (Edwalds-Gilbert G et al., Nucleic Acids Res. 25(13):2547-61. (1997)).

In some embodiments, in mammalian genes, polyadenylation sites can be usually preceded by AATAAA or ATTAAA ~20 bases before the cleavage site and could be followed by a more weakly conserved GT-based motif. There may be other possible sequences which can be recognizable by the poly (A) related set of proteins. These sequences could be also be used. (Cheng et al., Bioinformatics. 22(19):2320-5. (2006), and Hu et al., RNA. 11(10): 1485-93 (2005)).

In a broad embodiment, the poly (A) signal could be NNTANN, where N represents any of a nucleotide A, C, G, or T (Cheng et al., Bioinformatics. 22(19):2320-5. (2006), and Hu et al., RNA. 11(10):1485-93. (2005)).

Exon Splice Trapping Acceptors

In one embodiment, target sequence may contain sequences that can be recognizable and be spliced by the RNA splicesome, which provide a natural barrier to block 5' coding sequence of a fluorescent protein to be spliced with the 3' coding sequence of a fluorescent protein. Before exposing to recombinase activity, 5' coding sequence of a fluorescent protein may be spliced with one of the splice trapping acceptor site to generate a chimeric protein encoding by the 5' coding sequence of a fluorescent protein and the sequence downstream of the splice trapping acceptor site and sequence behind it till a poly(A) (Burn et al., Gene 161:183-187 (1995)) and Datson et al., Nucleic Acids Research. 24:1105-1111 (1996)).

In one embodiment, in event that there is no such suitable splice trapping acceptor site naturally available in the target region, a splice trapping acceptor sequence from other sources could be inserted at the downstream sequence of the first loxP site which located downstream of 5' coding sequence of a fluorescent protein. It may also be inserted at any location of the target sequence between two recombination sites to block the premature splicing between the 5' and 3' coding sequence of a fluorescent protein. The other sources of splice trapping acceptor sequence could include sequences came from, but not limited to, a naturally found exon acceptor site, a man-made sequence, or any sequences that are capable of trapping upstream exon sequence.

In some embodiments, there are many types of splice trapping acceptor site could be suitable to the purpose of intercept the 5' coding sequence of a fluorescent protein. Specifically, an EN2 (mouse En2 intron 2/exon 3 splice acceptor sequence) (SEQ ID NO: 7) splicing trapping acceptor could be used to trap the 5' coding sequence of a fluorescent protein (Nature Reviews Cancer 10, 696-706 (2010)).

Dual Fluorescence Reporters (FIG. 5)

In some embodiments, a single color fluorescence could not provide sufficient contrast in relation to surrounding cells as non-fluorescent cells could not be well detected by a fluorescent microscope. In some embodiments, a second fluorescent reporter can be introduced inside the target sequence, which may carry its own promoter or shares with the promoter from the first fluorescent protein. Before a cell exposed to a recombinase, the cell has fluorescence from the second fluorescent protein. After the cell exposed to a recombinase, the cell obtains fluorescence from the first fluorescent protein. This color switch scheme could provide more detailed visualization where and when a gene deletion had taken place in a cell.

Research Kits

A kit may include one or more containers housing the components of the invention and instructions for use. Specifically, such kits may include one or more agents described herein, along with instructions describing the intended application and the proper use of these agents. In certain embodiments agents in a kit may be in a pharmaceutical formulation and dosage suitable for a particular application and for a method of administration of the agents. Kits for research purposes may contain the components in appropriate concentrations or quantities for running various experiments.

The following is a listing of embodiments that are specifically contemplated herein.

In one embodiment, a recombinant nucleic acid construct is provided comprising in order from upstream to downstream:

(1) a promoter sequence;
(2) a nucleic acid sequence encoding a first portion of a reporter protein (e.g., fluorescent protein) including an N-terminus, wherein a protein product of said first portion is insufficient to provide fluorescent expression;
(3) a splice donor site;
(4) a heterologous nucleic acid sequence;
(5) a splice acceptor site;
(6) a nucleic acid sequence encoding a second portion of a reporter protein (e.g., fluorescent protein) including a C-terminus; and
(7) a poly(A) signal sequence.

In another embodiment, a method of introducing conditional and divided polynucleotide sequences coding for a reporter protein (e.g., fluorescent protein) into a mouse embryonic stem (ES) cell is provided, comprising:

(a) constructing a DNA targeting vector comprising, in order,
  (1) a 5' homology arm;
  (2) a recombinant nucleic acid construct in accordance with the invention, wherein the heterologous sequence comprises a target sequence flanked by two recombination sites; and
  (3) a 3' homology arm.

The DNA targeting vector may further comprises an antibiotic selectable marker gene inserted between the 5' homology arm and 3' homology arm.
(b) introducing the DNA targeting vector of (a) into the ES cell;
(c) selecting the ES cell of (b) for a targeted clone.

In another embodiment, a method of reporting gene deletion is provided comprising,
  (a) constructing a DNA targeting vector as described herein;
  (b) generating targeted germline mouse;
  (c) mating the targeted mouse with a recombinase expressing mouse;
  (d) activating a fluorescent protein by removing the target sequence by recombination between its recombination sites.

In a further embodiment, the nucleic acid construct of the invention may comprise a promoter wherein the promoter comprises a nucleic acid sequence capable of driving gene expression of downstream sequences in eukaryotic cells.

In an embodiment, the promoter may be a polymerase II promoter.

In another embodiment, the promoter may comprise a polymerase II promoter that is selected from the group consisting of ubiquitous promoter, cell specific promoter, inducible promoter, and constitutive promoter in eukaryotic cells.

In a further embodiment, the promoter is selected from the group consisting of CAG (SEQ ID NO: 1), CAGGS, CMV, hCMV, EF1, PGK, FABP, Lck, CamKII, CD19, Keratin, Albumin, aP2, Insulin, MCK, MyHC, WAP, Col2A, Mx, tet, and Trex promoter.

In other embodiments, the nucleic acid construct of the invention may comprise a reporter, wherein the reporter is a fluorescent protein which comprises a protein capable of absorption of a higher energy photon and emission of a lower energy photon in eukaryotic cells.

In particular embodiments, the reporter may comprise a fluorescent protein selected from the group consisting of blue/UV fluorescent proteins, cyan fluorescent proteins, green fluorescent proteins, yellow fluorescent proteins, orange fluorescent proteins, red fluorescent proteins, far-red fluorescent proteins, Near-IR fluorescent proteins, Long strokes shift fluorescent proteins, Photoactivable fluorescent proteins, Photoconvertible fluorescent proteins, and Photoswitchable fluorescent proteins.

In a further embodiment, the reporter comprises a fluorescent protein selected from GFP, EGFP (SEQ ID NO: 2), and DsRed (SEQ ID NO: 3).

In an embodiment of the invention, the nucleic acid construct may comprise splice donor site, wherein the splice donor site is a functional DNA sequence which can be spliced by splicesome.

In an embodiment, the first nucleotide of a 5' end of the intron is a G.

In another embodiment of the invention, the nucleic acid construct may comprise a splice acceptor site, wherein the splice acceptor site is a functional DNA sequence which can be spliced by splicesome.

In an embodiment, the last nucleotide of a 3' end of the intron is a G.

In one embodiment of the invention, the nucleic acid construct may comprise at least two recombination sites, wherein both of the recombination sites are identical.

In an embodiment of the invention, the nucleic acid construct may comprise at least two recombination sites, wherein both of the recombination sites are not identical.

In a further embodiment of the invention, the nucleic acid construct may comprise at least two recombination sites, wherein one of the recombination sites is a mutant recombination site.

In an embodiment of the invention, the recombination site is a wildtype recombination site selected from the group consisting of loxP (SEQ ID NO: 4), frt (SEQ ID NO: 5), rox (SEQ ID NO: 6), Vlox, Slox, attR, attL, attP, attB, or IR/DR sequences.

In an embodiment, one of the recombination sites is selected from the group consisting of lox511, lox5171, lox2272, M2, M7, M11, lox71, lox66, loxN, loxp 5171, F3, F5, F7, FL-IL10A, Vlox2272, Slox2272, VloxM1, SloxM2, VloxM2, SloxM2, Vlox43R, Vlox43L, Slox1R, or Slox1L.

In a further embodiment the method of reporter gene deletion comprises a recombinase enzyme, wherein the recombinase is an enzyme capable of deleting or inversing sequence between two recombination sites.

In a further embodiment, the recombinase is an enzyme capable of deleting or inversing sequence between two of its recognizable sites.

In another embodiment, the recombinase is selected from the group consisting of Cre, Flp, Dre, Vcre, Scre, Nigri, Panto, PhiC31, or Sleepingbeauty transposas.

In a further embodiment of the invention, the heterologous sequence further comprises an exon trapping sequence.

In an embodiment, the exon trapping sequence is EN2 exon trapping sequence (SEQ ID NO: 7).

In a further embodiment of the invention, the nucleic acid construct may further comprise a nucleotide sequence coding for a second fluorescent protein.

In an embodiment, the second fluorescent protein is DsRed fluorescent protein (SEQ ID NO: 3).

The following examples are offered by way of illustration only and are not intended to limit the invention in any manner. All patent and literature references cited herein are expressly incorporated by reference.

EXAMPLES

Example 1

Figure 6:
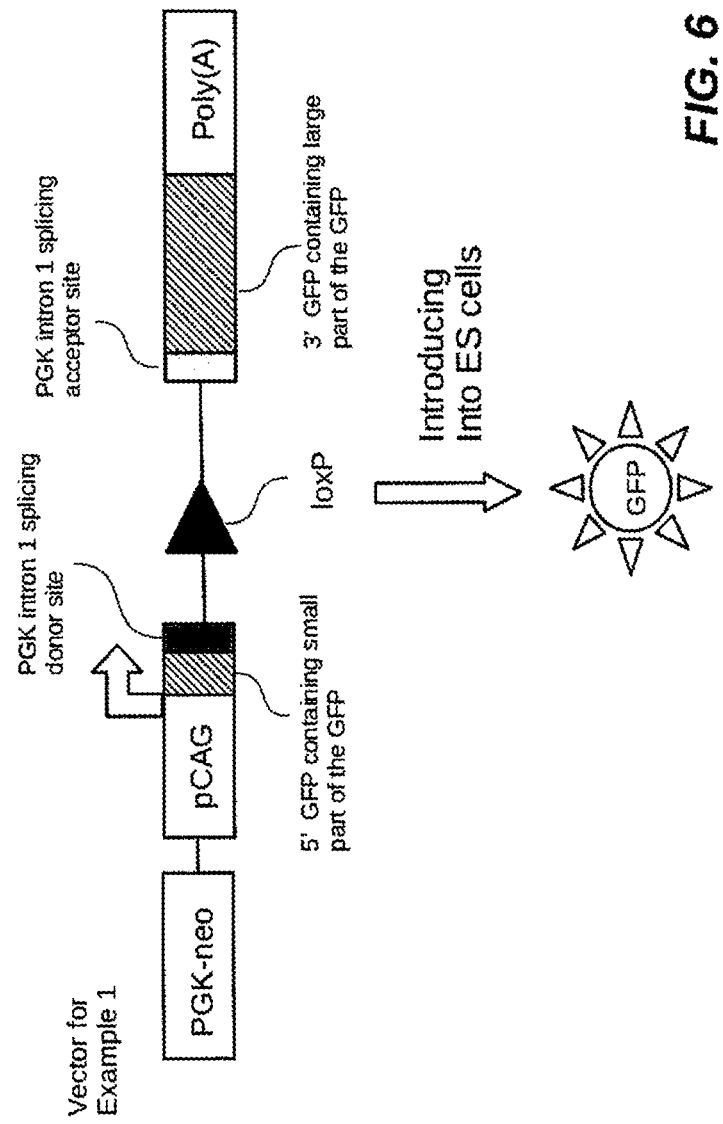
FIG. 6 shows a schematic diagram of the vector for experimental Example 1.

Inserting a Synthetic Intron Into a Site of GFP Sequence and Its Visualization in Vitro (FIG. 6).

Step 1. Constructing Vector

FIG. 6 shows a schematic diagram of the vector, wherein sequences containing a mouse PGK-1 intron 1 splice donor (SEQ ID NO: 8) and acceptor (SEQ ID NO: 9) and part of the PGK-1 intron sequence. The part of the PGK-1 intron sequence was incorporated in (SEQ ID NO: 8) and (SEQ ID NO: 9), respectively. An antibiotic select marker gene for providing selection by an appropriate drug was also included. The vector was inserted into coding sequence of a fluorescent protein, e.g., GFP. A wildtype loxP is included in the sequence between the splice donor and splice acceptor sites to test if loxP could interfere the splice of 5' GFP (SEQ ID NO: 10) and 3' GFP (SEQ ID NO: 11) since after cre mediated deletion could generate a single loxP site. The construct was introduced into a cell, e.g., a mouse stem cells.

Green fluorescence was observed by a fluorescent microscope. The results showed that the location of insertion and splicing was a success and the loxP site could not interfere with the expression of the fluorescent protein. The divided GFP coding sequence has a 5' portion which has a smaller and 3' portion which has a larger part of GFP coding sequence.

It was sought to express an optical marker, GFP, after inserting an intron into the coding sequence of the GFP.

Vector included, from 5' to 3',
1) a pCAG promoter (SEQ ID NO: 1);
2) a synthesized 5' GFP coding sequence (SEQ ID NO: 10);
3) a synthetic shorter version of 5' end of mouse phosphoglycerate kinase 1 (PGK-1) intron 1 including splicing donor site (SEQ ID NO: 8);
4) a synthetic wildtype loxP site (SEQ ID NO: 4);
5) a synthetic shorter version of 3' end of mouse phosphoglycerate kinase 1 (PGK-1) intron 1 including splicing acceptor site (SEQ ID NO: 9);
6) a synthesized 3' coding sequence GFP (SEQ ID NO: 11);
7) a synthetic poly(A) site (SEQ ID NO: 32).

Components from 1 to 7 were assembled into a carrier vector pSP72 (purchased from Promega) by using standard molecular biology procedures as described in (Sambrook et al., Molecular Cloning: A Laboratory Manual (New York: Cold Spring Harbor Laboratory Press, 1989).

An eukaryotic selection cassette, neomycin resistance gene, was also inserted inside the carrier vector with above components 1-8 such that the insertion of the neomycin resistance gene cassette located outside of the sequence of components 1-8.

The neomycin resistance gene has a PGK-1 promoter (SEQ ID NO: 18).

Step 2. Introducing Vector Into Mouse Embryonic Stem Cells By Electroporation
The Embryonic Stem Cell Medium (ES) was prepared by adding following components: Dulbecco's modified Eagle's Medium (DMEM) with high glucose (Gibco #11960-044) to the 500 ml bottle add: •6 mls of GlutaMAX, (GlutaMAX-1, Gibco 35050-061) •6 ml of diluted ß-mercaptoethanol, 100 µM final concentration. •6 mls of Sodium Pyruvate, 1 mM final (Gibco, 11360-070)≠6 mls of Non-essential amino acids, 100 µM final (Gibco, 11140-050) •1000 U/ml of LIF (Leukaemia inhibitory factor, Chemicon ESG1107) •penicillin/streptomycin (Gibco #15140-148, final concentration 50 ug/ml each) Plus the 15% fetal bovine serum.

Prior to electroporation day the following should be prepared: (i) one 10 cm plates containing a feeder layer of gamma ray inactivated neomycin resistant fibroblasts. (ii) ES cells should be grown to approximately 80% confluency such that approximately 1.times.10.sup.7 cells are available on day of electroporation.

On the electroporation day, 9 procedures need to be followed:
1. The ES media was changed two to four hours before the electroporation, cells will be harvested. Usually one 10 cm plate of ES cells will be needed. This plate will provide approximately 2.times.10.sup.7 cells. This is adequate for one electroporation.
2. Remove the media and wash by 10 ml PBS. Digest the ES cells using 3 ml of 0.25% trypsin/EDTA and incubating for 5 min at 37degree C. Add 10 ml of DMEM media to stop the trypsin reaction.
3. Collect cells into a 15 mL tube and spin the ES cells at 1500 rpm for 5 min.
4. Resuspend the ES cells in 1 ml of the electroporation buffer such that cell density is approximately 1.times.10.sup.7 cells/mL.
5. Cut the vector by NotI restriction enzyme at 37degree C. in 0.1 ml reaction for 2 hours and heat inactivate the enzyme at 80 degree C. for 10 minutes. Add 0.1 ml cut vector into the 1 ml ES cell suspension solution.
6. Add the mixture to a 0.4 cm electroporation cuvette. Mix up and down gently with a sterile transfer pipette. Electroporate with gene pulsar with settings at 0.4 Kvolts, 25 .mu.FD (time constant should be 0.4 or 0.5 sec).
7. Allow to stand for 10 min at room temperature. Plate out 0.3 ml of the electroporated ES cells to two times.10 cm plates, along with the proportionate amount of DMEM media.
8. twenty four hours later, begin selection with geneticin (G418) with a concentration of 150-250 µg per ml.
9. Change media daily. ES cells will grow to form colonies by day 10 or 11.

Step 3. Green Fluorescence Visualization Under Fluorescent Microscope The ES media from procedure number 9 was partially removed. The plate was transferred onto the observation platform of Nikon fluorescent zoom microscope. Green fluorescent signal excited by blue light generated from the Epi-fluorescent illuminator was observed and captured by digital camera (FIG. 11)

Example 2

Figure 7:
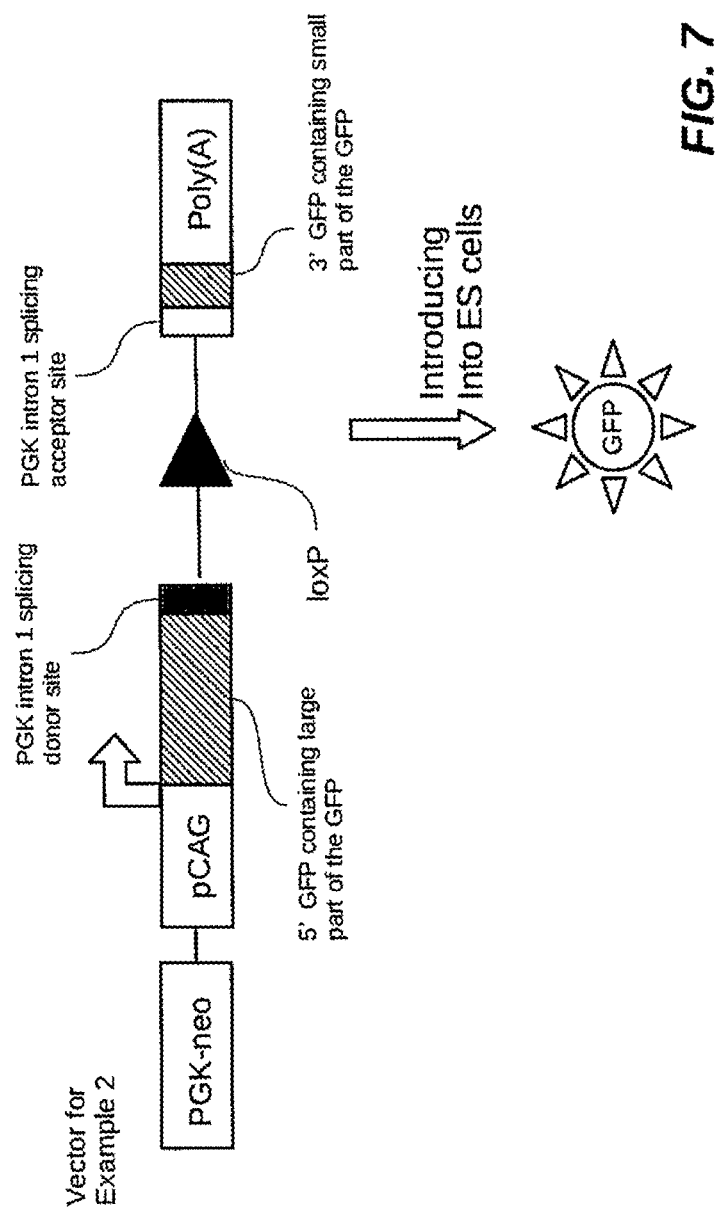
FIG. 7 shows a schematic diagram of the vector for experimental Example 2.

Inserting a Synthetic Intron Into a Different Site of GFP Sequence and Its Visualization in Vitro Step 1. Constructing Vector
FIG. 7 shows a schematic diagram of the vector to test if the coding sequence of a fluorescent protein, e.g., GFP can be divided at a different location. The same PGK-1 intron from EXAMPLE 1 was inserted into different location of the GFP coding sequence. The selected site for this experiment was more towards downstream of the GFP sequence. This design kept the 3'GFP sequence much shorter than that of EXAMPLE 1.

Vector included, from 5' to 3',
1) a pCAG promoter (SEQ ID NO: 1),
2) a synthesized 5' GFP coding sequence (SEQ ID NO: 12);
3) a synthetic shorter version of 5' end of mouse phosphoglycerate kinase 1 (PGK-1) intron 1 including splicing donor site (SEQ ID NO: 8);
4) a synthetic wildtype loxP site (SEQ ID NO: 4);
5) a synthetic shorter version of 3' end of mouse phosphoglycerate kinase 1 (PGK-1) intron 1 including splicing acceptor site (SEQ ID NO: 9);
6) a synthesized 3' coding sequence GFP (SEQ ID NO: 13);
7) a synthetic poly(A) site (SEQ ID NO: 20).

Components from 1 to 7 were assembled into a carrier vector pSP72 (purchased from Promega) by using standard molecular biology procedures as described in (Sambrook et al., Molecular Cloning: A Laboratory Manual (New York: Cold Spring Harbor Laboratory Press, 1989).

An eukaryotic selection cassette, neomycin resistance gene, was also inserted inside the carrier vector with above components 1-8 such that the insertion of the neomycin resistance gene cassette located outside of the sequence of components 1-8.

The neomycin resistance gene has a PGK-1 promoter (SEQ ID NO: 18).

Step 2. As described as Example 1, step 2.

Step 3. Green Fluorescence Visualization Under Fluorescent Microscope

The ES media from procedure number 9 was partially removed. The plate was transferred onto the observation platform of Nikon fluorescent zoom microscope. Green fluorescent signal was observed and captured by digital camera (FIG. 12). The results demonstrated that the insertion could be highly flexible.

Example 3

Figure 8:
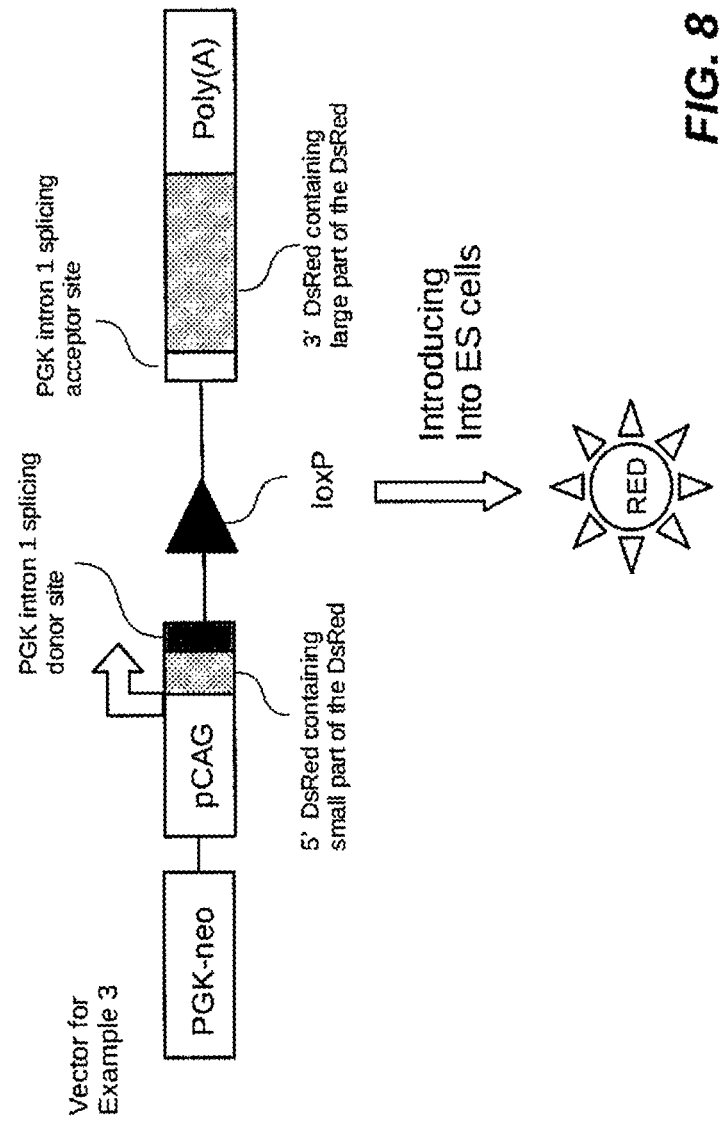
FIG. 8 shows a schematic diagram of the vector for experimental Example 3.

Inserting a Synthetic Intron Into Other Fluorescent Protein and Its Visualization in Vitro FIG. 8 shows a schematic diagram of the vector to test if the coding sequence of a different fluorescent protein, e.g., DsRed (a red fluorescent protein) could be divided by a different set of splice donor and acceptor. Splice donor and acceptor were selected from intron 9 of mouse albumin gene with sequences for splice donor (SEQ ID NO: 14) and splice acceptor (SEQ ID NO:15). The coding sequence of DsRed was divided into 5' and 3' parts. The 5' portion (SEQ ID NO: 16) has a shorter sequence and 3' (SEQ ID NO: 17) portion has a much longer sequence. The experiment constituted following 4 steps.

Step 1. Constructing Vector

Construct a vector included, from 5' to 3',
1) a pCAG promoter (SEQ ID NO:1);
2) a synthesized 5' DsRed coding sequence (SEQ ID NO: 16);
3) a synthetic shorter version of 5' end of mouse albumin intron 9 including splicing donor site (SEQ ID NO: 14);
4) a synthetic wildtype loxP site (SEQ ID NO: 4);
5) a synthetic shorter version of 3' end of mouse albumin intron 9 including splicing acceptor site (SEQ ID NO: 15);
6) a synthesized 3' coding sequence DsRed (SEQ ID NO: 17);
7) a synthetic poly(A) site (SEQ ID NO: 20).

Components from 1 to 7 were assembled into a carrier vector pSP72 (purchased from Promega) by using standard molecular biology procedures as described in (Sambrook et al., Molecular Cloning: A Laboratory Manual (New York: Cold Spring Harbor Laboratory Press, 1989).

An eukaryotic selection cassette, neomycin resistance gene, was also inserted inside the carrier vector with above components 1-7 such that the insertion of the neomycin resistance gene cassette located outside of the sequence of components 1-7.

The neomycin resistance gene has a PGK-1 promoter (SEQ ID NO: 18).

Step 2. As described as Example 1, step 2.

Step 3. Pick Up Colonies In following Procedures
a) Prepare a ES cell plate by rinsing with 10 ml of PBS.
b) Place the plate under the microscope to select undifferentiated healthy colonies.
c) Pick colonies using a P-20 pipette tips.
d) Carefully pick a colony without breaking up the colony into single cells, and transfer it into a 96-well plate with 0.25% trypsin.
e) Once all 16 colonies have been picked into the wells, incubate the plate in a 37 degree. C. incubator for 5 minutes.
f) Add 100 μl of media to each well. Pipette up and down ~10-15 times using the multichannel pipette to break up the colonies.
g) Transfer the cell suspension to a 96-well gelatinized plate.
h) Change media every day until 80% confluence.
i) Remove the media from the wells and wash with 100 μl PBS.j) Add 15 ul of 0.25% trypsin and incubate at 37 degree. C. for 5 minutes.
k) Add 100 μl of ES media containing fetal bovine serum and Pipette up and down ~10-15 times and mix and combine 16 wells of ES cells.

Step 4. Red Fluorescence Visualization Under Fluorescent Microscope

Ten μl of ES media containing the ES cells was transferred to a glass bottom plate for confocal microscope observation. The red fluorescence was observed and captured by a confocal microscope (FIG. 13). The results demonstrated that DNA sequence coding for other florescent protein can be fairly easy to divide into two parts by insertion of an intron sequence and other exon donor and acceptor can be used as well.

Example 4

Figure 9:
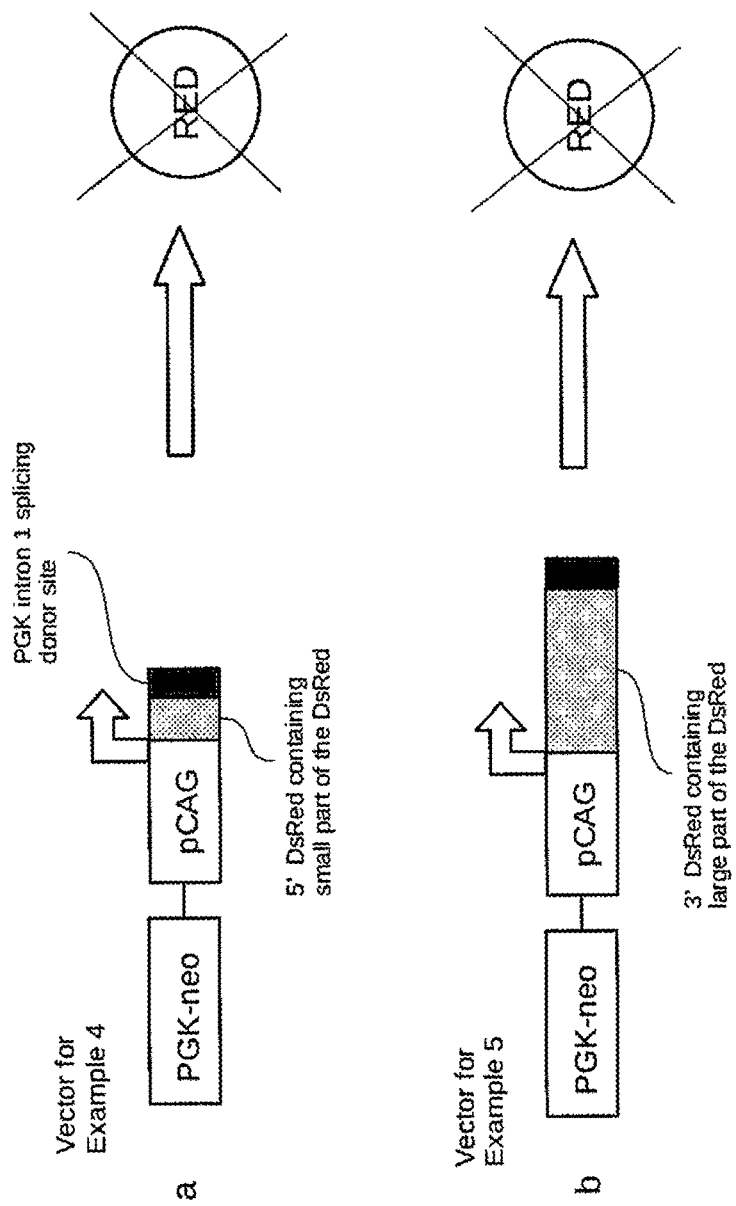
FIG. 9a shows a schematic diagram of the vector for experimental Example 4.
FIG. 9b shows a schematic diagram of the vector for experimental Example 5.

FIG. 9a shows a schematic diagram of the vector, wherein as per design, the 5' part of DeRed or 3' part of DsRed alone should not generate a functional red fluorescent protein. To test if it is true, two constructs were made: construct C1 (as Control 1) and construct C2 (as Control 2).

Figure 10:
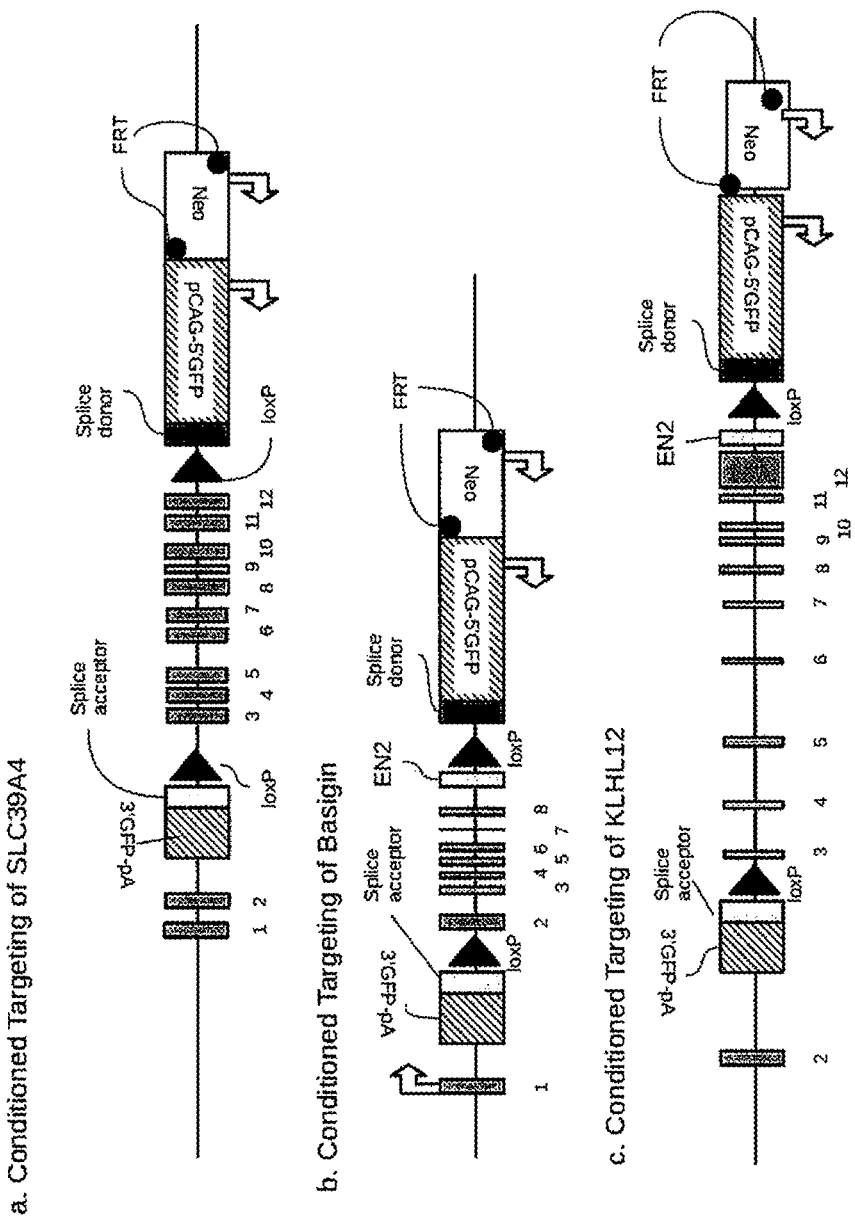
FIG. 10a shows a schematic diagram of the targeted allele by a targeting vector for a mouse SLC39A4 gene.
FIG. 10b shows a schematic diagram of the targeted allele by a targeting vector for a mouse Basigin gene with an addition of an EN2 exon trapping site.
FIG. 10c shows a schematic diagram of the targeted allele of a different mouse gene, KLHL12, with an EN2 exon trapping site.

Construct C1 has only 5' part of DSred, which was inserted directly behind the pCAG promoter. Experiments were conducted in 4 steps (FIG. 10a).

Step 1. Constructing Vector

Construct a vector which included of, from 5' to 3',
1) a pCAG promoter (SEQ ID NO: 1),
2) a synthesized 5' DsRed coding sequence (SEQ ID NO: 16);
3) a synthetic shorter version of 5' end of mouse albumin intron 9 including splicing donor site (SEQ ID NO: 14);

Components from 1 to 3 were assembled into a carrier vector pSP72 (purchased from Promega) by using standard molecular biology procedures as described in (Sambrook et al., Molecular Cloning: A Laboratory Manual (New York: Cold Spring Harbor Laboratory Press, 1989).

An eukaryotic selection cassette, neomycin resistance gene, was also inserted inside the carrier vector with above components 1-3 such that the insertion of the neomycin resistance gene cassette located outside of the sequence of components 1-3.

The rest of steps are the same, or almost the same, as described in steps 2-4 as described by EXAMPLE 3. There was no red fluorescence observed under confocal fluorescent microscope, which proved that 5' DsRed alone will not yield functional red fluorescent protein.

Example 5

FIG. 9b shows a schematic diagram of the vector for experimental Example 5, wherein only the 3' portion sequence of the fluorescent protein was linked to the same promoter as described in Example 1 (FIG. 6).

Construct C2 has only 3' part of DsRed, which was inserted directly behind the pCAG promoter. Experiments were conducted in 4 steps (FIG. 10b).

Step 1. Constructing Vector

Construct a vector which included, from 5' to 3',
1) a pCAG promoter (SEQ ID NO: 1),
2) a synthesized 3' DsRed coding sequence (SEQ ID NO: 17);
3) a poly (A) signal sequence (SEQ ID NO: 20)

Components from 1 to 3 were assembled into a carrier vector pSP72 (purchased from Promega) by using standard molecular biology procedures as described in (Sambrook et al., Molecular Cloning: A Laboratory Manual (New York: Cold Spring Harbor Laboratory Press, 1989).

An eukaryotic selection cassette, neomycin resistance gene, was also inserted inside the carrier vector with above components 1-3 such that the insertion of the neomycin resistance gene cassette located outside of the sequence of components 1-3.

The rest of steps are the same, or almost the same, as described in steps 2-4 as described by EXAMPLE 3. There was no red fluorescence observed under confocal fluorescent microscope, which proved that 3' DsRed alone will not generate functional red fluorescent protein.

Example 6

To test the divided GFP In Vivo, a mouse was created by targeting its SLC39A4 gene.

FIG. 10a shows a schematic diagram of the targeted allele by a targeting vector for a mouse SLC39A4 gene. A Psp72 (Promega) based plasmid vector including two sequences: 5'-CCCATCACTATCAAAGACGACAAGGGCAATCT-CAACCGCTGCATTG-3' (SEQ ID NO: 30) and 5'-CCT-GTTGCCCAGAACAGTGACAGATTCTTGGC-3' (SEQ ID NO: 31), was used to subclone a genomic fragment from a mouse BAC clone RP23-156P23 by using bacterial homologous-based recombination technique (Heermann et al., Microb Cell Fact. 7: 14. (2008) and Angrand et al., Nucleic Acids Res 27, e16 (1999). A 3' GFP cassette including poly (A) signal sequence, 3' GFP, a splice acceptor site, and a loxP site was inserted into the intron 2 of the mouse SLC39A4 gene, and a 5' GFP cassette including a loxP site, a splice donor site, 5' GFP, pCAG (promoter of CAG), a G418 resistance selection cassette (Neo) (SEQ ID NO: 18). was inserted into the sequence downstream of the exon 12. The targeting vector for SLC39A4 gene comprises:
(1) a 5' homology arm (SEQ ID NO: 21);
(2) a synthetic poly(A) site (SEQ ID NO: 32);
(3) a synthesized 3' coding sequence GFP (SEQ ID NO: 11);
(4) a synthetic shorter version of 3' end of mouse phosphoglycerate kinase 1 (PGK-1) intron 1 including splicing acceptor site (SEQ ID NO: 9);
(5) a synthetic wildtype loxP site (SEQ ID NO: 4);
(6) a target sequence of mouse SLC39A4 gene (SEQ ID NO: 22);
(7) a synthetic wildtype loxP site (SEQ ID NO: 4);
(8) a synthetic shorter version of 5' end of mouse kinase 1 (PGK-1) intron 1 including splicing donor site (SEQ ID NO: 8);
(9) a synthesized 5' GFP coding sequence (SEQ ID NO: 10);
(10) a pCAG promoter (SEQ ID NO: 1);
(11) a G418 resistance selection cassette (Neo) (SEQ ID NO: 18).
(12) a 3' homology arm (SEQ ID NO: 23).

Figure 14:
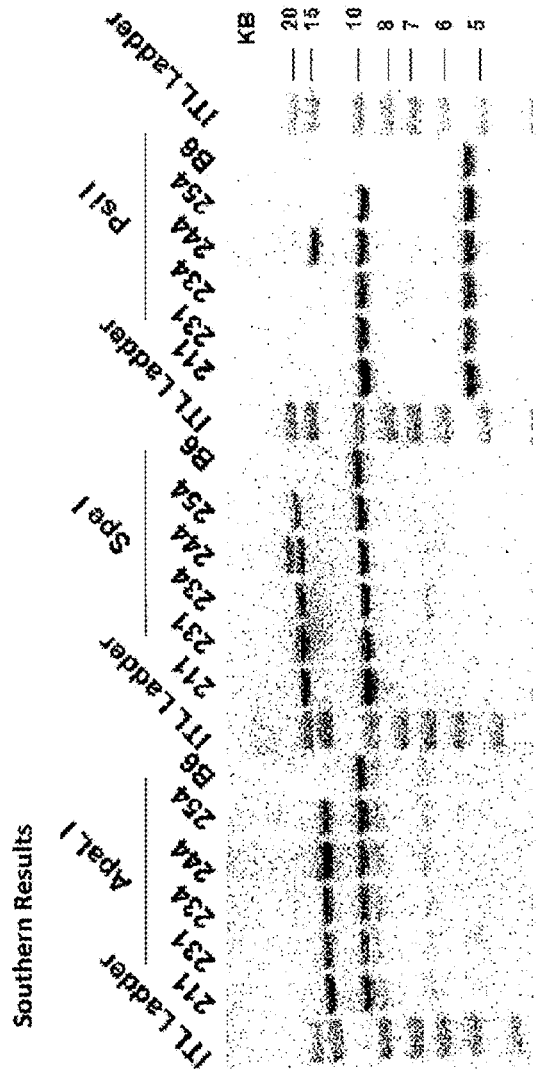
FIG. 14 shows results of southern blot analysis for targeted ES clones of mouse SLC39A4 gene.

The targeting vector was introduced into mouse stem cells by electroporation (Example 1, step 2) After selection of G418, targeted clones were identified by southern blot analysis (Southern et al, Journal of Molecular Biology. 98 (3): 503-517. (1975)) (FIG. 14).

Positive ES clones were injected into mouse blastocysts to generate mouse chimeras. These chimeras were then mated with wildtype mice to generate germline mouse with targeted modifications as described in the book "Gene Targeting: A Practical Approach" (ISBN-13: 978-0199637928. (2000)).

Figure 15:
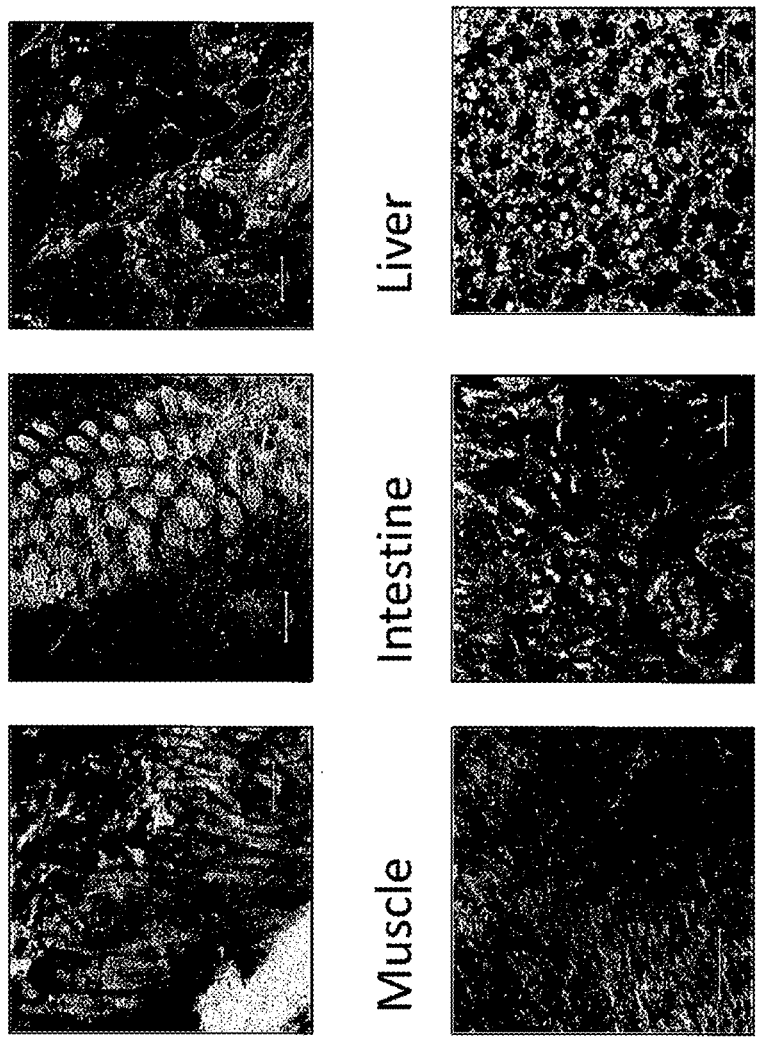
FIG. 15 shows the green fluorescence generated by mating targeted SLC39A4 gene with a Cre recombinase containing mouse.

The germline mouse with target allele was further mated with a Cre recombinase containing mouse (e.g., Sox2Cre (Jackson Laboratory)) to generate target gene deletion mice, wherein GFP was expressed (FIG. 15).

Example 7

To further test the divided GFP In Vivo including an EN2 exon trapping acceptor sequence, a mouse was created by targeting its Basigin gene.

FIG. 10b shows a schematic diagram of the targeted allele by a targeting vector for a mouse Basigin gene. A Psp72 (Promega) based plasmid vector was used to subclone a genomic fragment from a mouse fosmid clone WI1-1405E10 using standard molecular biology procedures (restriction enzyme cutting and ligation) as described in (Sambrook et al., Molecular Cloning: A Laboratory Manual (New York: Cold Spring Harbor Laboratory Press, 1989). Similarly, a 3' GFP cassette including poly (A) signal sequence, 3' GFP, a splice acceptor site, and a loxP site was inserted into the intron 1 of the mouse Basigin gene. And a 5' GFP cassette including a EN2 exon trapping site, loxP site, a splice donor site, 5' GFP, pCAG (promoter of CAG), a G418 resistance selection cassette (Neo) was inserted into the sequence downstream of the exon 8 by using bacterial homologous-based recombination technique (Heermann et al., Microb Cell Fact. 7: 14. (2008) and Angrand et al., Nucleic Acids Res 27, e16 (1999)).

The targeting vector for Basigin gene comprises:
(1) a 5' homology arm (SEQ ID NO: 24);
(2) a synthetic poly(A) site (SEQ ID NO: 20);
(3) a synthesized 3' coding sequence GFP (SEQ ID NO: 13);
(4) a synthetic shorter version of 3' end of mouse phosphoglycerate kinase 1 (PGK-1) intron 1 including splicing acceptor site (SEQ ID NO: 9);
(5) a synthetic wildtype loxP site (SEQ ID NO: 4);
(6) a target sequence of mouse Basigin gene (SEQ ID NO: 25);
(7) a synthetic wildtype loxP site (SEQ ID NO: 4);
(8) a synthetic shorter version of 5' end of mouse phosphoglycerate kinase 1 (PGK-1) intron 1 including splicing donor site (SEQ ID NO: 8);
(9) a synthesized 5' GFP coding sequence (SEQ ID NO: 12);
(10) a pCAG promoter (SEQ ID NO: 1);
(11) a G418 resistance selection cassette (Neo) (SEQ ID NO: 18).
(12) a 3' homology arm (SEQ ID NO: 26).

Figure 16B:
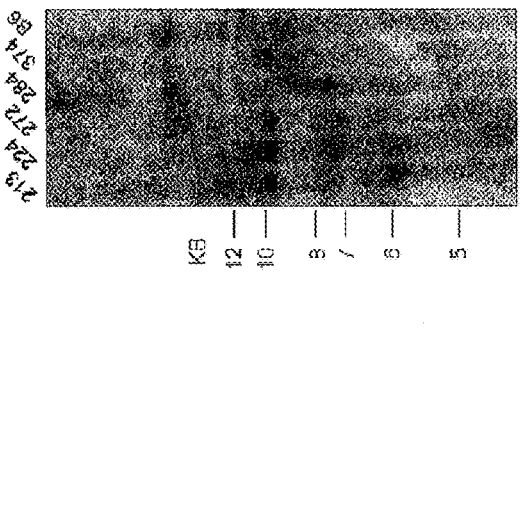

The targeting vector was introduced into mouse stem cells by electroporation (Example 1, step 2) After selection of G418, targeted clones were identified by southern blot analysis (Southern et al, Journal of Molecular Biology. 98 (3): 503-517. (1975)) (FIGS. 16a and 16b).

Positive ES clones were injected into mouse blastocysts to generate mouse chimeras. These chimeras were then mated with wildtype mice to generate germline mouse with targeted modifications as described in the book "Gene Targeting: A Practical Approach" (ISBN-13: 978-0199637928. (2000)).

The germline mouse with target allele was further mated with a Cre recombinase containing mouse (e.g., Sox2Cre (Jackson Laboratory)) to generate target gene deletion mice, wherein GFP was expressed (FIG. 17).

Example 8

To further test the divided GFP In Vivo including an EN2 exon trapping acceptor sequence, a mouse gene KLHL12 was targeted. FIG. 10c shows a schematic diagram of the targeted allele of a different mouse gene, KLHL12, with an EN2 exon trapping site. A mouse fosmid clone WI1-2351K21 was used as starting material similar to as described method in Example 6 and 7. The targeting vector was constructed by inserting a 3' GFP cassette including poly (A) signal sequence, 3' GFP, a splice acceptor site, and a loxP site into the intron 2 of the mouse KLHL12 gene and inserting a 5' GFP cassette including a EN2 exon trapping site, loxP site, a splice donor site, 5' GFP, pCAG (promoter of CAG), a G418 resistance selection cassette (Neo) into the sequence downstream of the exon 12. The targeting vector of mouse KLHL gene includes:

(1) a 5' homology arm (SEQ ID NO: 27);
(2) a synthetic poly(A) site (SEQ ID NO: 20);
(3) a synthesized 3' coding sequence GFP (SEQ ID NO: 13);
(4) a synthetic shorter version of 3' end of mouse phosphoglycerate kinase 1 (PGK-1) intron 1 including splicing acceptor site (SEQ ID NO: 9);
(5) a synthetic wildtype loxP site (SEQ ID NO: 4);
(6) a target sequence of mouse KLHL12 gene (SEQ ID NO: 28);
(7) a synthetic wildtype loxP site (SEQ ID NO: 4);
(8) a synthetic shorter version of 5' end of mouse phosphoglycerate kinase 1 (PGK-1) intron 1 including splicing donor site (SEQ ID NO: 8);
(9) a synthesized 5' GFP coding sequence (SEQ ID NO: 12);
(10) a pCAG promoter (SEQ ID NO: 1);
(11) a G418 resistance selection cassette (Neo) (SEQ ID NO: 18).
(12) a 3' homology arm (SEQ ID NO: 29).

The targeting vector was introduced into mouse stem cells by electroporation (Example 1, step 2) After selection of G418, targeted clones were identified by southern blot analysis (Southern et al, *Journal of Molecular Biology.* 98 (3): 503-517 (1975)) (FIGS. 18a and 18b). Positive ES clones were injected into mouse blastocysts to generate mouse chimeras. These chimeras were then mated with wildtype mice to generate germline mouse with targeted modifications as described in the book "Gene Targeting: A Practical Approach" (ISBN-13: 978-0199637928. (2000)).

Positive ES clones were injected into mouse blastocysts to generate mouse chimeras. These chimeras were then mated with wildtype mice to generate germline mouse with targeted modifications as described in the book "Gene Targeting: A Practical Approach" (ISBN-13: 978-0199637928. (2000)). The targeted mice were mated with mice carrying a Cre recombinase driven by interleukin 17 promoter (Jackson laboratory, stock #016879) green fluorescence was observed in intestine (FIG. 19).

What is claimed is:

1. A recombinant nucleic acid construct comprising in order from upstream to downstream:
   a promoter sequence;
   a nucleic acid sequence encoding a first portion of a reporter protein including an N-terminus, wherein a protein product of the reporter protein is insufficient to provide reporter expression;
   a splice donor site;
   a heterologous nucleic acid sequence;
   a splice acceptor site;
   a nucleic acid sequence encoding a second portion of a reporter protein including a C-terminus; and
   a poly(A) signal sequence.

2. The nucleic acid construct of claim 1, wherein the promoter is a nucleic acid sequence capable of driving gene expression of downstream sequences in eukaryotic cells.

3. The nucleic acid construct of claim 2, wherein the promoter is a polymerase II promoter.

4. The nucleic acid construct of claim 2, wherein the promoter is selected from the group consists of ubiquitous promoter, cell specific promoter, inducible promoter, and constitutive promoter in eukaryotic cells.

5. The nucleic acid construct of claim 4, wherein the promoter is selected from the group consists of the CAG (SEQ ID NO: 1), CAGGS, CMV, hCMV, EF1, PGK, FABP, Lck, CamKII, CD19, Keratin, Albumin, aP2, Insulin, MCK, MyHC, WAP, Col2A, Mx, tet, and Trex promoter.

6. The nucleic acid construct of claim 1, wherein the reporter protein comprises a fluorescent protein, wherein said fluorescent protein is a protein capable of absorption of a higher energy photon and emission of a lower energy photon in eukaryotic cells.

7. The nucleic acid construct of claim 6, wherein fluorescent protein is selected from the group consisting of blue/UV fluorescent proteins, cyan fluorescent proteins, green fluorescent proteins, yellow fluorescent proteins, orange fluorescent proteins, red fluorescent proteins, far-red fluorescent proteins, Near-IR fluorescent proteins, Long strokes shift fluorescent proteins, Photoactivable fluorescent proteins, Photoconvertible fluorescent proteins, and Photoswitchable fluorescent proteins.

8. The nucleic acid construct of claim 7, wherein fluorescent protein is selected from GFP, EGFP, and DsRed.

9. The nucleic acid construct of claim 1, wherein the splice donor site is a DNA sequence at beginning of an intron which can be spliced by splicesome.

10. The nucleic acid construct of claim 9, wherein the first nucleotide of a 5' end of the intron is a G.

11. The nucleic acid construct of claim 1, wherein the splice acceptor site is a DNA sequence at the end of an intron which can be spliced by splicesome.

12. The nucleic acid construct of claim 11, wherein the last nucleotide of a 3' end of the intron is a G.

13. The nucleic acid construct of claim 1, wherein the reporter protein is selected from the group consisting of beta-galactosidase, luciferase, and chloramphenicol acetyltransferase.

14. A nucleic acid construct comprising: a DNA targeting vector comprising, in order, a 5' homology arm; the nucleic acid construct according to claim 1, wherein the heterologous sequence comprises a sequence flanked by two recombinant sites; and a 3' homology arm, wherein the DNA targeting vector further comprises an antibiotic selectable marker gene inserted between the 5' homology arm and 3' homology arm.

15. The nucleic acid construct of claim 14, wherein both of the recombination sites are identical.

16. The nucleic acid construct of claim 14, wherein both of the recombination sites are not identical.

17. The nucleic acid construct of claim 14, wherein one of the recombination sites is a mutant recombination site.

18. The nucleic acid construct of claim 14, wherein at least one recombination site is a wildtype recombination site consists of loxp, frt, rox, Vlox, Slox, attR, attL, attP, attB, or IR/DR sequences.

19. The nucleic acid construct of claim 17, wherein one of the recombination site is selected from the group consisting of lox511, lox5171, lox2272, M2, M7, M11, lox71, lox66, loxN, loxp 5171, F3, F5, F7, FL-IL10A, Vlox2272, Slox2272, VloxM1, SloxM2, VloxM2, SloxM2, Vlox43R, Vlox43L, Slox1R, or Slox1L.

* * * * *